United States Patent
Ashkenazi

(10) Patent No.: US 7,750,118 B2
(45) Date of Patent: Jul. 6, 2010

(54) APO-2 RECEPTOR POLYPEPTIDES

(75) Inventor: Avi J. Ashkenazi, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 446 days.

(21) Appl. No.: 11/245,053

(22) Filed: Oct. 7, 2005

(65) Prior Publication Data

US 2006/0035334 A1 Feb. 16, 2006

Related U.S. Application Data

(60) Division of application No. 10/423,448, filed on Apr. 25, 2003, which is a continuation of application No. 10/288,917, filed on Nov. 6, 2002, now abandoned, which is a continuation of application No. 10/052,798, filed on Nov. 2, 2001, now Pat. No. 7,314,619, which is a division of application No. 09/079,029, filed on May 14, 1998, now Pat. No. 6,342,369.

(60) Provisional application No. 60/046,615, filed on May 15, 1997, provisional application No. 60/074,119, filed on Feb. 9, 1998.

(51) Int. Cl.
C07K 14/435 (2006.01)
C07K 14/705 (2006.01)
A61K 38/17 (2006.01)

(52) U.S. Cl. ........................... 530/350; 514/2

(58) Field of Classification Search ................ None
See application file for complete search history.

(56) References Cited

U.S. PATENT DOCUMENTS

| | | | |
|---|---|---|---|
| 3,691,016 A | 9/1972 | Patel | |
| 3,969,287 A | 7/1976 | Jaworek | |
| 4,179,337 A | 12/1979 | Davis | |
| 4,195,128 A | 3/1980 | Hildebrand | |
| 4,229,537 A | 10/1980 | Hodgins | |
| 4,247,642 A | 1/1981 | Hirohara | |
| 4,301,144 A | 11/1981 | Iwashita | |
| 4,330,440 A | 5/1982 | Ayers | |
| 4,342,566 A | 8/1982 | Theofilopoulos | |
| 4,399,216 A | 8/1983 | Axel | |
| 4,419,446 A | 12/1983 | Howley | |
| 4,496,689 A | 1/1985 | Mitra | |
| 4,601,978 A | 7/1986 | Karin | |
| 4,640,835 A | 2/1987 | Shimizu | |
| 4,670,417 A | 6/1987 | Iwasaki | |
| 4,676,980 A | 6/1987 | Segal | |
| 4,736,866 A | 4/1988 | Leder | |
| 4,791,192 A | 12/1988 | Nakagawa | |
| 4,816,567 A | 3/1989 | Cabilly | |
| 4,855,235 A | 8/1989 | Takahashi | |
| 4,870,009 A | 9/1989 | Evans | |
| 4,965,199 A | 10/1990 | Capon | |
| 5,010,182 A | 4/1991 | Brake | |
| 5,153,118 A | 10/1992 | Wright | |
| 5,158,885 A | 10/1992 | Bradstock | |
| 5,194,596 A | 3/1993 | Tischer | |
| 5,350,836 A | 9/1994 | Kopchick | |
| 5,364,934 A | 11/1994 | Drayna | |
| 5,580,756 A | 12/1996 | Linsley | |
| 5,756,677 A | 5/1998 | Lewis | |
| 5,763,223 A | 6/1998 | Wiley | |
| 5,910,574 A | 6/1999 | Presta et al. | |
| 6,046,048 A | 4/2000 | Askenkazi | |
| 6,072,047 A | 6/2000 | Rauch | |
| 6,252,050 B1 | 6/2001 | Ashkenazi | |
| 6,313,269 B1 | 11/2001 | Deen | |
| 6,342,369 B1 | 1/2002 | Ashkenazi | |
| 6,417,328 B2 | 7/2002 | Alnemri | |
| 6,455,040 B1 | 9/2002 | Wei et al. | |
| 6,455,262 B1 | 9/2002 | Cox | |
| 6,635,743 B1 | 10/2003 | Ebner et al. | |
| 6,642,358 B1 * | 11/2003 | Rauch et al. | ............ 530/350 |
| 6,689,744 B2 | 2/2004 | Gao et al. | |
| 6,743,625 B2 | 6/2004 | Ni | |
| 6,872,568 B1 | 3/2005 | Jian Ni | |
| 7,314,619 B2 | 1/2008 | Adams et al. | |
| 7,528,239 B1 | 5/2009 | Rauch et al. | |
| 2002/0048566 A1 | 4/2002 | El-Deiry | |
| 2002/0048785 A1 | 4/2002 | Holtzman | |
| 2002/0072091 A1 | 6/2002 | Ni | |
| 2002/0098550 A1 | 7/2002 | Ni | |

(Continued)

FOREIGN PATENT DOCUMENTS

DE 266710 4/1989

(Continued)

OTHER PUBLICATIONS

Wells, J.A. (1990). Additivity of mutational effects in proteins. Biochemistry. 29(37):8509-8517.*

(Continued)

Primary Examiner—Christine J Saoud
Assistant Examiner—Jon M Lockard
(74) Attorney, Agent, or Firm—Sidley Austin LLP

(57) ABSTRACT

Novel polypeptides, designated Apo-2, which are capable of modulating apoptosis are provided. Compositions including Apo-2 chimeras, nucleic acid encoding Apo-2, and antibodies to Apo-2 are also provided.

14 Claims, 20 Drawing Sheets

U.S. PATENT DOCUMENTS

| | | |
|---|---|---|
| 2002/0115154 A1 | 8/2002 | Alnemri |
| 2002/0150985 A1 | 10/2002 | Adams et al. |
| 2002/0160446 A1 | 10/2002 | Holtzman |
| 2002/0161195 A1 | 10/2002 | Alnemri |
| 2002/0161196 A1 | 10/2002 | Alnemri |
| 2003/0004313 A1 | 1/2003 | Ashkenazi |
| 2003/0017161 A1 | 1/2003 | Ashkenazi |
| 2003/0133932 A1 | 7/2003 | Zhou |
| 2003/0148455 A1 | 8/2003 | Ashkenazi et al. |
| 2003/0180296 A1 | 9/2003 | Salcedo et al. |
| 2004/0009552 A1 | 1/2004 | Adams |
| 2005/0233958 A1 | 10/2005 | Ni |
| 2005/0282230 A1 | 12/2005 | Ashkenazi |
| 2006/0035334 A1 | 2/2006 | Adams |
| 2006/0073570 A1 | 4/2006 | Adams |
| 2006/0084147 A1 | 4/2006 | Adams |

FOREIGN PATENT DOCUMENTS

| | | |
|---|---|---|
| EP | 036776 | 9/1981 |
| EP | 073657 | 3/1983 |
| EP | 117058 A2 | 8/1984 |
| EP | 0117060 A2 | 8/1984 |
| EP | 125023 A1 | 11/1984 |
| EP | 173494 | 3/1986 |
| EP | 278776 | 8/1988 |
| EP | 307247 | 3/1989 |
| EP | 321196 | 6/1989 |
| EP | 362179 A2 | 4/1990 |
| EP | 417563 | 3/1991 |
| EP | 510691 | 10/1992 |
| EP | 870827 | 10/1998 |
| GB | 2211504 | 7/1989 |
| WO | WO 87/05330 | 9/1987 |
| WO | WO 89/02922 | 4/1989 |
| WO | WO 89/05859 | 6/1989 |
| WO | WO 90/13646 | 11/1990 |
| WO | WO 91/00358 | 1/1991 |
| WO | WO 91/00360 | 1/1991 |
| WO | WO 91/08291 | 6/1991 |
| WO | WO 92/01047 | 1/1992 |
| WO | WO 92/01810 | 2/1992 |
| WO | WO 92/20373 | 11/1992 |
| WO | WO 92/20791 | 11/1992 |
| WO | WO 93/00109 | 1/1993 |
| WO | WO 93/06213 | 4/1993 |
| WO | WO 93/08829 | 5/1993 |
| WO | WO 93/11236 | 6/1993 |
| WO | WO 93/19172 | 9/1993 |
| WO | WO 94/04679 | 3/1994 |
| WO | WO 94/04690 | 3/1994 |
| WO | WO 94/29348 | 12/1994 |
| WO | WO 95/01438 | 1/1995 |
| WO | WO 95/10540 | 4/1995 |
| WO | WO 95/11301 | 4/1995 |
| WO | WO 95/15388 | 6/1995 |
| WO | WO 95/31544 | 11/1995 |
| WO | WO 97/01633 | 1/1997 |
| WO | WO 97/25428 | 7/1997 |
| WO | WO 98/35986 | 8/1998 |
| WO | WO 98/41629 | 9/1998 |
| WO | WO 98/46643 | 10/1998 |
| WO | WO 98/51793 | 11/1998 |
| WO | WO 98/58062 | 12/1998 |
| WO | WO 99/02653 | 1/1999 |
| WO | WO 99/09165 | 2/1999 |
| WO | WO 99/11791 | 3/1999 |
| WO | WO 99/12963 | 3/1999 |
| WO | WO 99/64461 | 12/1999 |
| WO | WO 00/66156 | 11/2000 |
| WO | WO 00/77191 | 12/2001 |
| WO | WO 02/053727 | 7/2002 |
| WO | WO 02/094880 | 11/2002 |
| WO | WO 03/037913 | 5/2003 |
| WO | WO 03/038043 A2 | 5/2003 |

OTHER PUBLICATIONS

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
"BLAST Results A-1-A-47" (GenBank).
"BLAST Results B-1-B-31" (GenBank, -EST).
"BLAST Results C-1-C-36" (Patent).
"BLAST Results D-1-D-40" (Dayhoff -patent).
"BLAST Results E-1-E-25" (Human -pat).
"BLAST Results F-1-F-52" (Dayhoff).
Brodeur et al., "Mouse-Human Myeloma Partners for the Production of Heterohybridomas" Monoclonal Antibody Production Techniques and Applications, New York:Marcel Dekker, Inc. pp. 51-63 (1987).
Brojatsch et al., "CAR1, A TNFR-Related Protein, Is a Cellular Receptor for Cytopathic Avain Leukosis-Sarcoma Viruses and Mediates Apoptosis." Cell. 87:845-855 (1996).
Browning et al., "Lymphotoxin \142, a Novel Member of the TNF Family That Forms a Heteromeric Complex with Lymphotoxin on the Cell Surface" Cell 72:847-856 (1993).
Bruggemann et al., "Designer Mice: The Production of Human Antibody Repertoires in Transgenic Animals" Year in Immunology 7:33-40 (1993).
Bryn et al., "Biological Properties of a CD4 Immunoadhesin" Nature 344:667-670 (Apr. 12, 1990).
Canaani et al., "Regulated Expression of Human Interferon \142\sub1\nor Gene After Transduction into Cultured Mouse and Rabbit Cells" Proc. Natl. Acad. Sci. USA 79:5166-5170 (Sep. 1982).
Capon et al., "Designing CD4 Immunoadhesins for AIDS Therapy" Nature 337(9):525-531 (Feb. 1989).
Carter et al., "Antibody Engineering Using Very Long Template-Assembled Oligonucleotides" Methods: A Companion to Methods in Enzymology 3(3):183-192 (Dec. 1991).
Carter et al., "Humanization of an Anti-p185\supHER2\nor Antibody For Human Cancer Therapy" Proc. Natl. Acad. Sci. USA 89:4285-4289 (May 1992).
Carter et al., "Improved Oligonucleotide Site-Directed Mutagenesis Using M13 Vectors" Nucl. Acids Res. 13(12):4431-4443 (1985).
Cha et al., "Crystal Structure of Trail-DR5 Complex Identifies a Critical Role of the Unique Frame Insertion in Conferring Recognition Specificty" The Journal of Biological Chemistry, JBC Papers in Press vol. 275(40):31171-31177 (Jul. 11, 2000).
Chamow et al., "A Humanized, Bispecific Immunoadhesion-Antibody That Retargets CD3\sup+\nor Effectors to Kill HIV-1-Infected Cells" Journal of Immunology 153:4268-4280 (1994).
Chang et al., "Phenotypic Expression in E. coli of a DNA Sequence Coding for Mouse Dihydrofolate Reductase" Nature 275:617-624 (Oct. 19, 1978).
Chapman, "A Region of the 75 kDa neurotrophin receptor homologous to the death domains of TNFR-I and Fas" B.S. Chapman/FEBS Letters 374:216-220 (1995).
Chaudhary et al., "Death Receptor 5, a New Member of the TNFR Family, and DR4 Induce FADD-Dependent Apoptosis and Activate the NF-\153B Pathway" Immunity 7:821-830 (1997).
Chemotherapy Service Ed., M.C. Perry, Baltimore, MD:Williams & Wilkins (1992).
Holland and Holland, "Isolation and Identification of Yeast Messenger Ribonucleic Acids Coding for Enolase, Glyceraldehyde-3-phosphate Dehydrogenase, and Phosphoglycerate Kinase" Biochemistry 17(23):4900-4907 (1978).
Hoogenboom and Winter, "By-Passing Immunisation: Human Antibodies from Synthetic Repertoires of Germline V\subH\nor Gene Segments Rearranged in Vitro" J. Mol. Biol. 227:381-388 (1992).
Hoogenboom, "Designing and optimizing library selection strategies for generating high-affinity antibodies" Trends in Biotechnology 15(2):62-70 (Feb. 1997).

Hopp et al., "A Short Polypeptide Marker Sequence Useful for Recombinant Protein Identification and Purification" Bio/Technology 6:1204-1210 (1988).

Hsiao and Carbon, "High-frequency Transformation of Yeast by Plasmids Containing the Cloned Yeast Arg4 Gene" Proc. Natl. Acad. Sci. USA 76:3829-3833 (1979).

Hsu et al., "TRADD-TRAF2 and TRADD-FADD interactions define two distinct TNF receptor 1 signal transduction pathways" Cell 84:299-308 (1996).

Hunter et al., "Preparation of Iodine 131 Labelled Human Growth Hormone of High Specific Activity" Nature 194:495-496 (1962).

Hymowitz et al., "Triggering Cell Death: The Crystal Structure of Apo2L/TRAIL in a Complex with Death Receptor 5." Molecular Cell. 4(4):563-571 (1999).

Iliades et al., "Triabodies: single chain Fv fragments without a linker form trivalent trimers" FEBS Letters 409(3):437-441 (Jun. 16, 1997).

Itoh et al., "The Polypeptide Encoded by the cDNA for Human Cell Surface Antigen Fas Can Mediate Apoptosis." Cell. 66:233-243 (1991).

Jakobovits et al., "Analysis of Homozygous Mutant Chimeric Mice: Deletion of the Immunoglobulin Heavy-Chain Joining Region Blocks B-cell Development and Antibody Production" Proc. Natl. Acad. Sci. USA 90:2551-2555 (Mar. 1993).

Jakobovits et al., "Germ-line Transmission and Expression of a Human-Derived Yeast Artificial Chromosome" Nature 362:255-258 (Mar. 18, 1993).

Johnson et al., "Expression and Structure of the Human NGF Receptor" Cell 47:545-554 (1986).

Jones et al., "Replacing the Complementarity-Determining Regions in a Human Antibody with Those From a Mouse." Nature. 321:522-525 (May 29, 1986).

Jones, E., "Proteinase Mutants of Saccharomyces Cerevisiae" Genetics 85(1):23-33 (1977).

Jones, Y., "Cytokine Receptor Complexes Verses Cell Adhesion Interactions—Upping the Affinity" (Abstract No. M11.OA.002 presented at the XVIIIth IUCr.

Congress & General Assembly held in Glasgow, Scotland on Aug. 4-13, 1999.) pp. 133.

Kabat et al. Sequences of Proteins of Immunological Interest (NIH Publn. No. 91-3242), 5th edition.

Keown et al., "Methods for Introducing DNA into Mammalian Cells" Methods in Enzymology 185:527-537 (1990).

Kingsman et al., "Replication in Saccharomyces Cerevisiae of Plasmid pBR313 Carrying DNA from the Yeast trp1 Region" Gene 7:141 (1979).

Kitson et al., "A Death-Domain-Containing Receptor that Mediates Apoptosis" Nature 384:372-375 (1996).

Kohler and Milstein., "Continuous Cultures of Fused Cells Secreting Antibody of Predefined Specificity" Nature. 256:495-497 (1975).

Kohno et al., "A Second Tumor Necrosis Factor Receptor Gene Product Can Shed a Naturally Occuring Tumor Necrosis Factor Inhibitor." Proc. Natl. Acad. Sci. USA 87:8331-8335 (1990).

Koopman et al., "Annexin V for Flow Cytomeric Detection of Phosphatidylserine Expression on B Cells Undergoing Apoptosis" Blood 84:1415-1420 (1994).

Kortt et al., "Single-chain Fv fragments of anti-neuraminidase antibody NC10 containing five- and ten-residue linkers form dimers and with zero-residue linker a trimer" Protein Engineering 10(4):423-433 (Apr. 1997).

Kozak, "An analysis of vertebrate mRNA sequences: intimations of translational control" Journal of Cell Biology 115:887-903 (1991).

Kozbor et al., "A Human Hybrid Myeloma for Production of Human Monoclonal Antibodies" The Journal of Immunology 133(6):3001-3005 (1984).

Krammer et al., "Regulation of Apoptosis in the Immune System" Curr. Op. Immunol. 6:279-289 (1994).

Kyriakis et al, "Sounding the Alarm: Protein Kinase Cascades Activated by Stress and Inflammation" Journal of Biological Chemistry 271:24313-24316 (1996).

Laimins et al., "Osmotic Control of kdp Operon Expression in *Escherichia coli*" Proc. Natl. Acad. Sci. USA 78(1):464-468 (Jan. 1981).

Lasky et al., "DNA sequence analysis of the type-common glycoprotein-D genes of herpes simplex virus types 1 and 2" DNA 3(1):23-29 (1984).

Lesslauer et al., "Bioactivity of recombinant human TNF receptor fragments" J. Cell. Biochem. (abstract only, Supplement 15F; P432) p. 115 (1991).

Lewis et al., "Cloning and Expression of cDNAs for Two Distinct Murine Tumor Necrosis Factor Receptors Demonstrate One Receptor is Species Specific." PNAS USA. 88:2830-2834 (1991).

Li et al., "Targeted Mutation of the DNA Methyltransferase Gene Results in Embryonic Lethality." Cell. 69:915-926 (Jun. 1992).

LIFESEQ Database EST Sequence Reference "1".

LIFESEQ Database EST Sequence Reference "2".

Liu et al., "Dissection of TNF Receptor 1 Effector Functions: JNK Activation is not Linked to Apoptosis While NF-\153\norB\nor Activation Prevents Cell Death" Cell 87:565-576 (1996).

Loetscher et al., "Molecular Cloning and Expression of the Human 55 kd Tumor Necrosis Factor Receptor" Cell 61:351-359 (1990).

Luckow et al., "Trends in the Development of Baculovirus Expression Vectors" Bio/Technology 6:47-55 (1988).

Lusky et al., "Bovine Papilloma Virus Contains an Activator of Gene Expression at the Distal End of the Early Transcription Unit" Molecular & Cellular Biology 3(6):1108-1122 (Jun. 1983).

Mather, J.P., "Establishment and Characterization of Two Distinct Mouse Testicular Epithelial Cell Lines" Biol. Reprod. 23:243-252 (1980).

Maxam et al., "Sequencing End-labeled DNA with Base-Specific Chemical Cleavages" Methods in Enzymology 65:499-560 (1980).

McCafferty et al., "Phage antibodies: filamentous phage displaying antibody variable domains" Nature 348:552-554 (1990).

Mendez et al., "Functional transplant of megabase human immunoglobulin loci recapitulates human antibody response in mice" Nature Genetics 15:146-156 (Feb. 1997).

Messing et al., "A System for Shotgun DNA Sequencing" Nucleic Acids Research 9(2):309-321 (1981).

Miller et al., "An Insect Baculovirus Host-Vector System for High-Level Expression of Foreign Genes" Genetic Engineering, Setlow et al., Plenum Publishing, vol. 8:277-298 (1986).

Milstein and Cuello, "Hybrid Hybridomas and Their Use in Immunohistochemistry" Nature 305:537-540 (Oct. 1983).

Mongkolsapaya et al., "Structure of the TRAIL-DR5 complex reveals mechanisms conferring specificity in apoptotic initiation" Nature Structural Biology 6(11):1048-1053 (Nov. 1999).

Montgomery et al., "Herpes Simplex Virus-1 Entry into Cells Mediated by a Novel Member of the TNF/NGF Receptor Family" Cell 87(3):427-436 (1996).

Moore et al., "Apoptosis in CHO Cell Batch Cultures: Examination by Flow Cytometry" Cytotechnology 17:1-11 (1995).

Morrison et al., "Chimeric Human Antibody Molecules: Mouse Antigen-Binding Domains with Human Constant Region Domains" Proc. Natl. Acad. Sci. USA 81:6851-6855 (1984).

Morrison et al., "Transfer and expression of immunoglobulin genes" Annual Review of Immunology 2:239-256 (1984).

Morrison, S. L., "Transfectomas Provide Novel Chimeric Antibodies" Science 229:1202-1207 (Sep. 20, 1985).

Mulligan et al., "Expression of a Bacterial Gene in Mammalian Cells" Science 209:1422-1427 (Sep. 1980).

Munro, "Uses of chimaeric antibodies" Nature 312:597 (1984).

Munson and Rodbard, "Ligand: A Versatile Computerized Approach for Characterization of Ligand-Binding Systems" Analytical Biochemistry 107:220-239 (1980).

Muzio et al., "FLICE, A Novel FADD-Homologosu ICE/CED-3-like Protease, Is Recruited to the CD95 (Fas/APO-1) Death-Inducing Signaling Complex" Cell 85:817-827 (1996).

Nagata and Golstein, "The Fas Death Factor" Science 267:1449-1456 (1995).

Nagata, S., "Apoptosis by Death Factor." Cell. 88:355-365 (Feb. 1997).

NCBI/GenBank EST; Locus AA223122:(computer printout attached).

NCBI/GenBank EST; Locus AA232440:(computer printout attached).

NCBI/GenBank EST; Locus HS75A7R:(computer printout attached).

Neri et al., "Engineered recombinant antibodies for immunotherapy" Cell Biophysics 27(1):47-61 (Aug. 1995).

Neuberger et al., "Recombinant Antibodies Possessing Novel Effector Functions" Nature 312:604-608 (Dec. 13, 1984).

Nophar et al., "Soluble Forms of Tumor Necrosis Factor Receptors (TNF-Rs). The cDNA for the Type I TNF-R, Cloned Using Amino Acid Sequence Data of its Soluble Form, Encodes Both the Cell Surface and a Soluble Form of the Receptor." EMBO Journal. 9:3269-3278 (1990).

Nygren, H., "Conjugation of Horseradish Peroxidase to Fab Fragments with Different Homobifunctional and Heterobifunctional Cross-Linking Reagents" The Journal of Histochemistry and Cytochemistry 30(5):407-412 (1982).

Olsson and Kaplan, "Human-human hybridomas producing monoclonal antibodies of predefined antigenic specificity" Proc. Natl. Acad. Sci. USA 77(9):5429-5431 (1980).

Osborne et al., "Transcription Control Region Within the Protein-coding Portion of Adenovirus E1A Genes" Molecular & Cellular Biology 4(7):1293-1305 (Jul. 1984).

Paborsky et al., "Mammalian Cell Transient Expression of Tissue Factor for the Production of Antigen" Protein Eng. 3(6):547-553 (1990).

Pain et al., "Preparation of Protein A-Peroxidase Monoconjugate Using a Heterobifunctional Reagent, and its Use in Enzyme Immunoassays" Journal of Immunological Methods 40:219-230 (1981).

Pan et al., "An Antagonist Decoy Receptor and a Death-Domain Containing Receptor for TRAIL." Science. 277:815-818 (Aug. 1997).

Pan et al., "The Receptor for the Cytotoxic Ligand TRAIL." Science. 276:111-113 (Apr. 4, 1997).

Pavlakis et al., "Expression of Two Human Growth Hormone Genes in Monkey Cells Infected by Simian Virus 40 Recombinants" Proc. Natl. Acad. Sci. USA 78(12):7398-7402 (Dec. 1981).

Peetre et al., "A tumor necrosis factor binding protein is present in human biological fluids" European Journal of Haematology 41:414-419 (1988).

Pennica et al., "Human Tumour Necrosis Factor: Precursor Structure, Expression and Homology to Lymphotoxin" Nature 312:724-729 (1984).

Peppel and Beutler, "Chimaeric TNF-Receptor-IgG Molecule Acts as Soluble Inhibitor of TNF Mediated Cytotoxicity" J. Cell. Biochem. (abstract only, Supplement 15F; P439) p. 118 (1991).

Peterson, N., "Recombinant antibodies: alternative strategies for developing and manipulating murine-derived monoclonal antibodies" Laboratory Animal Science 46(1):8-14 (Feb. 1996).

Pitti et al., "Induction of Apoptosis by Apo-2 Ligand, a New Member of the Tumor Necrosis Factor Cytokine Family" Journal of Biological Chemistry 271:12687-12690 (1996).

Pluckthun., "Antibodies From *Escherichia coli*." The Pharmacology of Monoclonal Antibodies: Handbook of Experimental Pharmacology., Rosenberg and Moore, eds., Berlin:Springer-Verlag, Chapter 11, vol. 113:269-315 (1994).

U.S. Patent Interference No. 105,380, "Decision—Motions—Bd.R. 125(a)" with attachments (Paper 95), filed Mar. 9, 2007 (89 pages).

U.S. Patent Interference No. 105,380, "Order—Priority Times—Bd. R. 104(c)" (Paper 96), filed Mar. 9, 2007 (5 pages).

U.S. Patent Interference No. 105,381, "Decision—Motions—Bd.R. 125(a)" with attachments (Paper 101), filed Mar. 26, 2007 (104 pages).

U.S. Patent Interference No. 105,381, "Order—Priority Times—Bd. R. 104(c)" (Paper 102), filed Mar. 29, 2007 (5 pages).

U.S. Patent Interference No. 105,361, "Decision on Motions" (Paper 107), filed Nov. 28, 2007 (28 pages).

U.S. Patent Inteference No. 105,361, "Order—Miscellaneous—Bd. R. 104(a)" (Paper 113), filed Feb. 20, 2008 (4 pages).

U.S. Patent Interference No. 105,361, "Judgment—Request for Adverse—Bd.R. 127(b)" (Paper 114), filed Feb. 20, 2008 (4 pages).

U.S. Patent Interference No. 105,240, "Decision—Motions—Bd.R. 125(a)" (Paper 133), filed Jul. 26, 2007 (73 pages).

U.S. Patent Interference No. 105,240, "Order—Miscellaneous—Bd. R. 104(a)" (Paper 139), filed Oct. 16, 2007 (3 pages).

U.S. Patent Interference No. 105,240, "Judgment—Order to Show Cause—Bd.R. 202(d)" (Paper 141), filed Nov. 20, 2007 (3 pages).

U.S. Patent Interference No. 105,381, "Decision—Order to Show Cause" (Paper 134), filed Jul. 27, 2007 (13 pages).

U.S. Patent Interference No. 105,381, "Judgment—Order to Show Cause" (Paper 135), filed Jul. 27, 2007 (4 pages).

Espevik et al., "Characterization of Binding and Biological Effects of Monoclonal Antibodies against a Human Tumor Necrosis Factor Receptor" J. Exp. Med. 171:415-426 (1990).

Essentials of Pharmacology $2^{nd}$ Edition, Chapter 1: General Principles and Pharmacokinetics p. 1-33 (1996).

Fadeel et al., "Anti-Fas 1gG1 antibodies recognizing the same epitope of Fas/APO-1 mediate different biological effects in vitro" International Immunology, 9(2):201-209 (1996).

Feinstein, E., et al. The Death Domain: A Module Shared by Proteins with Diverse Cellular Functions, TIBS 20:342-344 (1995).

Feldman et al. "TNFα as a Therapeutic Target in Rheumatoid Arthritis" Ciruculatory Shock 43:179-184 (1994).

Frade et al., Nature 383:166 (1996).

Griffiths, et al. "Human anti-self antibodies with high specificity from phage display libraries", The EMBO J., 12:725-734 (1993).

Hess, S., A Novel Function of CD 40: Induction of Cell Death in Transformed Cells, J. Exp. Med. 183:159-167 (1996).

Higgins and Sharo, "CLUSTAL: a package for performing multiple sequence alignment on a microcomputer" Gene. 73(1) 237-244 (1988).

Hofmann & Tschopp, The death domain motif found in Fas (Apo-1) and TNF receptor is present in proteins involved in apoptosis and axonal guidance, FEBS Letters, 371:321-323 (1995).

Hsu, H., The TNF Receptor-1 Associated Protein TRADD Signals Cell Death and Bf-kB Activation, Cell, 81:495-504 (1995).

Huisman et al., "Paclitaxel Triggers Cell Death Primarily via Caspase-independent Routes in the Non-Small Cell Lung Cancer Cell Line NCI-H460," Clinical Cancer Research 8:596-606 (2002).

Itoh and Nagata, "A Novel Protein Domain Required for Apoptosis (Mutational Analysis of Human Fas Antigen" Journal of Biological Chemistry, vol. 268, No. 15, May 25, pp. 10932-10937 (1993).

James, K., "Human Monoclonal Antibody Technology," The Pharmacology of Monoclonal Antibodies: Handbook of Experimental Pharmacology, Rosenberg and Moore, eds., Berlin:Springer-Verlag, Chapter 1, vol. 113:3-22 (1994).

Johnson et al., "Signal Transduction Pathways Regulated by Mitogen-activated/Extracellular Respnse Kinase Kinase Kinase Induce Cell Death" J. Biol. Chem. 271:3229-3237 (1996).

Kabat et al., Attempts to locate residues in complementary-determining regions of antibody combining sites that make contact with antigen, Proc. Nat. Acad. Sci., 73:617-619 (1976).

Kabat et al., Some correlations between specificity and sequence of the first complementarity-determining region segments of human Kappa light chains, PNAS 73: 4471-4473.

Kehoe & Seide, Immunoglobulin structure and function: genetic control of antibody diversity, J. Am. Vet. Med. Assoc. 181(10):1000-1004, (1982).

Kobayashi et al., "Specificity problem; of polyclonal rabbit antibody" J. Clin. Pathol. 41:705-706, 1988.

Lippincott's Illustrated Reviews: Pharmacology $2^{nd}$ Edition, Chapter 2: Pharmacokinetics and Drug Receptors p. 17-26 (1997).

Liu, et al., Mechanism of antigen-driven selection in germinal centres, Nature, 342:929-931 (1989).

Locksley et al., "The TNF and TNF Receptor Superfamilies: Integrating Mammalian Biology" Cell 104:487-501 (Feb. 2001).

Mackay et al., "Lymphotoxin β Receptor Triggering Induces Activation of the Nuclear Factor κB Transcription Factor in Some Cell Types" J. Biol. Chem., 271(40): 24934-24938 (Oct. 4, 1996).

Maini et al., "Targeting TNFα for the therapy of rheumatoid arthritis" Clinical and Experimental Rheumatology 12 (Suppl. 11): 563-566 (1994).

Mapara, et al., APO-1 mediated apoptosis or proliferation in human chronic B lymphocytic leukemia: correlation with bcl-2 oncogene expression, Eur. J. Immunol. 23:702-708.

Mark et al., J. Biol. Chem. 269(14): 10720 (1994).

Morrison, et al., Analysis of receptor clustering on cell surfaces by imaging fluorescent particles, Biophys. J., 67(3):1280-1290 (1994).

Mühlenbeck et al., J. Biol. Chem. 275(41): 32208 (2000).

Naismith & Sprang, "Tumor Necrosis Factor Receptor Superfamily, " J. Inflamm., 47:1-7 (1996).

Nakai and Kanehisa, "A Knowledge Base for Predicting Protein Localization Sites in Eukaryotic Cells" Genomics 14:897-911 (1992).

Novotny et al., Molecular Anatomy of the Antibody Binding Site, J. Biol. Chem., 258:14433-14437 (1983).

Ogasawara et al., Nature 364:806 (1993).

Prakash, V., et al. The Interaction of Vincristine with Calf Brain Tubulin, J. Bio. Chem., 258:3, 1689-1697 (1983).

Reed, Amer. J. Path. 157(5):1415-1430 (2000).

Reed et al., Sci. STKE 2004, re9 (2004).

Rennert, et al., "Surface Lymphotoxin a/B complex is required for development of peripheral lymphoid organs," J. Exp. Med., 184:1999 (1996).

Ross, Elliott M., "Pharmacodynamics: Mechanisms of Drug Action and the Relationship Between Drug Concentration and Effect" Goodman & Gilman's The Pharmacological Basis Of Therapeutics, Ninth Edition, Chapter 2: pp. 29-41 (1996).

Sato, et al., A novel member of the TRAF family of putative signal transducing protein binds to the cytosolic domain of CD40, FEBS Letters 358:113-118 (1995).

Sevier, et al., Monoclonal Antibodies in Clinical Immunology, Clin. Chem., 27:1797-1806 (1981).

Sheehan et al., "Monoclonal Antibodies Specific for Murine p55 and p75 Tumor Necrosis Factor Receptors: Identification of a Novel In Vivo Role for p75" J. Exp. Med. 181:607-617 (1995).

Srivastava, "TRAIL/Apo-2L: Mechanisms and Clinical Applications in Cancer," Neoplasia 3:535-546 (2001).

Stedman's Medical Dictionary, $26^{th}$ Edition, p. 38 (1995).

Tartaglia et al., "The two different receptors for tumor necrosis factor mediate distinct cellular responses" Proc. Natl. Acad. Sci. USA 88:9292-9296 (Oct. 1991).

Notice of Opposition dated May 14, 2008 filed on behalf of Human Genome Sciences, Inc. regarding European Patent No. 0 981 618 (70 pages).

Notice of Opposition dated May 15, 2008 filed on behalf of Amgen Inc. regarding European Patent No. 0 981 618 (25 pages).

U.S. Appl. No. 08/799,861, filed Feb. 13, 1997.
U.S. Appl. No. 08/815,255, filed Mar. 12, 1997.
U.S. Appl. No. 08/820,364, filed Mar. 12, 1997.
U.S. Appl. No. 08/829,536, filed Mar. 28, 1997.
U.S. Appl. No. 08/843,651, filed Apr. 16, 1997.
U.S. Appl. No. 08/843,652, filed Apr. 16, 1997.
U.S. Appl. No. 08/853,684, filed May 9, 1997.
U.S. Appl. No. 08/869,852, filed Jun. 4, 1997.
U.S. Appl. No. 08/883,036, filed Jun. 26, 1997.
U.S. Appl. No. 08/916,625, filed Aug. 22, 1997.
U.S. Appl. No. 09/042,583, filed Mar. 17, 1998.
U.S. Appl. No. 09/565,009, filed May 4, 2000.
U.S. Appl. No. 09/712,726, filed Nov. 14, 2000.
U.S. Appl. No. 60/040,846, filed Mar. 17, 1997.
U.S. Appl. No. 60/041,230, filed Mar. 14, 1997.
U.S. Appl. No. 60/054,021, filed Jul. 29, 1997.
U.S. Appl. No. 60/132,498, filed May 4, 1999.

Adams et al., " Molecular cloning of mouse immunoglobulin heavy chain messenger ribonucleic acids coding for \155, \141, \1471, \1472a, and \1473 chains" Biochemistry 19:2711-2719 (1980).

Amakawa et al., "The Hodgkin Disease Antigen CD30 is Crucial for Antigen-Induced Death of Developing T Cells" Symposium on Programmed Cell Death (Abstract No. 10), Cold Spring Harbor Laboratory (1995).

Aplin and Wriston, "Preparation, Properties, and Applications of Carbohydrate Conjugates of Proteins and Lipids" CRC Crit. Rev. Biochem. 10(4):259-306 (1981).

Askenazi and Chamow, "Immunoadhesins: An Alternative to Human Monoclonal Antibodies" Methods: A Companion to Methods in Enzymology 8:104-115 (1995).

Ashkenazi et al., "Protection Against Endotoxic Shock by a Tumor Necrosis Factore Receptor Immunoadhesin" Proc. Natl. Acad. Sci. 88:10535-10539 (1991).

Autologous Bone Marrow Transplantation: Proceedings of the Third International Sympsium, Dicke et al., University of Texas M.D. Anderson Hospital (1987).

Baldwin, A., "The NF-\153\norB\nor and I\153\nor Proteins: New Discoveries and Insights" Ann. Rev. Immunol. 14:649-683 (1996).

Banerji et al., "A Lymphocyte-specific Cellular Enhancer Is Located Downstream of the Joining Region in Immunoglobulin Heavy Chain Genes" Cell 33:729-740 (Jul. 1983).

Banner et al., "Crystal Structure of the Soluble Human 55 kd TNF Receptor-Human TNF\142 Complex: Implications for TNF Receptor Activation" Cell 73:431-445 (1993).

Barr and Tomei, "Apoptosis and Its Role in Human Disease" Bio/Technology 12:487-493 (1994).

Bianchi et al., "Transformation of the yeast Kluyveromyces lactis by New Vectors Derived from the 1.6\155m Circular Plasmid pKD1" Curr. Genet. 12:185-192 (1987).

Bodemer et al., "TRAMP, A Novel Apoptosis-Mediating Receptor with Sequence Homology to Tumor Necrosis Factor Receptor 1 and Fas(Apo-1/CD95)." Immunity. 6:79-88 (1997).

Boerner et al., "Production of Antigen-Specific Human Monoclonal Antibodies From In Vitro-Primed Human Splenocytes" The Journal of Immunology 147(1):86-95 (Jul. 1991).

Boldin et al., "Involvement of MACH, a Novel MORT1/FADD-Interacting Protease, in Fas/APO-1- and TNF Receptor-Induced Cell Death" Cell 85:803-815 (1996).

Boldin et al., "Self-Association of the "Death Domains" of the p55 Tumor Necrosis Factor (TNF) Receptor and Fas/APO1 Prompts Signaling for TNF and Fas/APO1 Effects" Journal of Biological Chemistry 270:387-391 (1995).

Boulianne et al., "Production of functional chimaeric mouse/human antibody" Nature 312:643-646 (Dec. 13, 1984).

Bradley, "Production and Analysis of Chimaeric Mice" Teratocarcinomas and Embryonic Stem Cells: A Practical Approach, E. J. Robertson, ed., IRL, Oxford, Chapter 5, pp. 113-151 (1987).

Brockhaus et al., "Identification of Two Types of Tumor Necrosis Factor Receptors on Human Cell Lines by Monoclonal Antibodies." Proc. Natl. Acad. Sci. USA 87:3127-3131 (1990).

"BLAST Results A-1-A-47" (GenBank), (1998).
"BLAST Results B-1-B-31" (GenBank, -EST), (1998).
"BLAST Results C-1-C-36" (Patent), (1998).
"BLAST Results D-1-D-40" (Dayhoff -patent), (1998).
"BLAST Results E-1-E-25" (Human -pat), (1998).
"BLAST Results F-1-F-52" (Dayhoff), (1998).

Brodeur et al., "Mouse-Human Myeloma Partners for the Production of Heterohybridomas" Monoclonal Antibody Production Techniques and Applications, New York:Marcel Dekker, Inc. pp. 51-63 (1987).

Brojatsch et al., "CAR1, A TNFR-Related Protein, Is a Cellular Receptor for Cytopathic Avian Leukosis-Sarcoma Viruses and Mediates Apoptosis." Cell. 87:845-855 (1996).

Browning et al., "Lymphotoxin \142, a Novel Member of the TNF Family That Forms a Heteromeric Complex with Lymphotoxin on the Cell Surface" Cell 72:847-856 (1993).

Bruggermann et al., "Designer Mice: The Production of Human Antibody Repertories in Transgenic Animals" Year in Immunology 7:33-40 (1993).

Byrn et al., "Biological Properties of a CD4 Immunoadhesin" Nature 344:667-670 (Apr. 12, 1990).

Canaani et al., "Regulated Expression of Human Interferon \142\sub1\nor Gene After Transduction into Cultured Mouse and Rabbit Cells" Proc. Natl. Acad. Sci. USA 79:5166-5170 (Sep. 1982).

Capon et al., "Designing CD4 Immunoadhesins for AIDS Therapy" Nature 337(9):525-531 (Feb. 1989).

Carter et al., "Antibody Engineering Using Very Long Template-Assembled Oligonucleotides" Methods: A Companion to Methods in Enzymology 3(3):183-192 (Dec. 1991).

Carter et al., "Humanization of an Anti-p185\supHER2\nor Antiody For Human Cancer Therapy" Proc. Natl. Acad. Sci. USA 89:4285-4289 (May 1992).

Carter et al., "Improved Oligonucleotide Site-Directed Mutagenesis Using M13 Vectors" Nucl. Acids Res. 13(12):4431-4443 (1985).

Cha et al., "Crystal Structure of TRAIL-DR5 Complex Identifies a Critical Role of the Unique Frame Insertion in Conferring Recognition Specificity" The Journal of Biological Chemistry, JBC Papers in Press vol. 275(40):31171-31177 (Jul. 11, 2000).

Chamow et al., "A Humanized, Bispecific Immunoadhesin-Antibody That Retargets CD3\sup+\nor Effectors to Kill HIV-1-Infected Cells" Journal of Immunology 153:4268-4280 (1994).

Chang et al., "Phenotypic Expression in *E. coli* of a DNA Sequence Coding for Mouse Dihydrofolate Reductase" Nature 275:617-624 (Oct. 19, 1978).

Chapman, "A Region of the 75 kDa neurotrophin receptor homologous to the death domains of TNFR-I and Fas" B.S. Chapman/FEBS Letters 374:216-220 (1995).

Chaudhary et al., "Death Receptor 5, a New Member of the TNFR Family, and DR4 Induce FADD-Dependent Apoptosis and Activate the NF-\153B Pathway" Immunity 7:821-830 (1997).

Chemotherapy Service Ed., M.C. Perry, Baltimore, MD:Williams & Wilkins (1992).

Chinnaiyan and Dixit, "The Cell-Death Machine" Current Biology 6:555-562 (1996).

Chinnaiyan et al., "FADD, a novel death domain-containing protein, interacts with the death domain of Fas and initiates apoptosis" Cell 81:505-512 (1995).

Chinnaiyan et al., "FADD/MORT1 Is a Common Mediator of CD95 (Fas/APO-1) and Tumor Necrosis Factor Receptor-induced Apoptosis" Journal of Biological Chemistry 271:4961-4965 (1996).

Chinnaiyan et al., "Interaction of CED-4 with CED-3 and CED-9: A Molecular Framework for Cell Death" Science 275:1122-1126 (1997).

Chinnaiyan et al., "Signal Transduction by DR3, A Death Domain-Containing Receptor Related to TNFR-1 and CD95." Science. 274:990-992 (1996).

Chothia and Lesk, "Canonical Structures for the Hypervariable Regions of Immunoglobulins" J. Mol. Biol 196:901-917 (1987).

Chothia, "The Nature of the Accessible and Buried Surfaces in Proteins" Journal Mol. Biol. 105:1-14 (1976).

Chuntharapai and Kim, "Generation of Monoclonal Antibodies to Chemokine Receptors" Methods in Enzymology 288:15-27 (1997).

Chuntharapai et al., "The induction and blocking of apoptosis by anti Apo2 monoclonal antibodies" FASEB Journal (Annual Meeting of the Professional Research Scientists for Experimental Biology) 13(4):A518 (1999).

Cleveland and Ihle, "Contenders in FasL/TNF Death Signaling" Cell 81:479-482 (1995).

Cohen, "Programmed Cell Death in the Immune System" Advances in Immunol. 50:55-85 (1991).

Cole et al., "The EBV-Hybridoma Technique and Its Application to Human Lung Cancer" Monoclonal Antibodies and Cancer Therapy, New York:Alan R. Liss, Inc. pp. 77-96 (1985).

Creighton,, "Protein Biosynthesis" Proteins: Structures and Molecular Principles, San Francisco:W.H. Freeman & Co. pp. 79-86 (1983).

Darzynkiewicz et al., "Assays of Cell Viability: Discrimination of Cells Dying by Apoptosis" Methods in Cell Biol. 41:15-38 (1994).

David and Reisfeld., "Protein Iodination with Solid State Lactoperoxidase." Biochemistry 13(5):1014-1021 (1974).

de Boer et al., "The tac Promoter: A functional Hybrid Derived From the trp and lac Promoters" Proc. Natl. Acad. Sci. USA 80:21-25 (1983).

Dealtry et al., "DNA Fragmentation and Cytotoxicity Caused by Tumor Necrosis Factor is Enhanced by Interferon-\147" European Journal of Immunology 17:689-693 (1987).

Degli-Esposti et al., "Cloning and Characterization of TRAIL-R3, a Novel Member of the Emerging TRAIL Receptor Family" Journal of Experimental Medicine 186(7):1165-1170 (1997).

Depicker et al., "Nopaline Synthase: Transcript Mapping and DNA Sequence" J. Mol. Appl. Gen. 1:561-573 (1982).

Dieffenbach et al., PCR Primer: A Laboratory Manual, Cold Spring Harbor Laboratory Press pp. 1-16;133-142 (1995).

Dolby et al., "Cloning and partial nucleotide sequence of human immunoglobulin\155 chain cDNA from B cells and mouse-human hybridomas" Proc. Natl. Acad. Sci. USA 77(10):6027-6031 (1980).

Duskin et al., "Relationship of the Structure and Biological Activity of the Natural Homologues of Tunicamycin" Journal of Biological Chemistry 257:3105-3109 (1982).

Eck and Sprang, "The structure of tumor necrosis factor-\141 at 2.6 A resolution" Journal of Biological Chemistry 264(29):17595-17605 (1989).

Eck et al., "The Structure of Human Lymphotoxin (Tumor Necrosis Factor-\142) at 1.9-A Resolution" J. Bio. Chem. 267:2119-2122 (1992).

Edge et al., "Deglycosylation of glycoproteins by trifluoromethanesulfonic acid" Analytical Biochemistry 118:131-137 (1981).

Ellis, S., "Recognition of HLA-B27 and Related Antigen by a Monoclonal Antibody" Human Immunology 5:49-59 (1982).

Emery et al., "Osteoprotegerin Is a Receptor for the Cytotoxic Ligand Trail" Journal of Interferon and Cytokine Research (Abstract No. 2.17 from the 7th Intl. Tumor Necrosis Factor Congress May 17-21) 18(5):A-47 (May 1998).

Enari et al., "Involvement of an ICE-like protease in Fas-mediated Apoptosis" Nature 375:78-81 (1995).

Evan et al., "Isolation of Monoclonal Antibodies Specific for Human c-myc Proto-Oncogene Product" Molecular & Cellular Biology 5:3610-3616 (1985).

Fadok et al., "Exposure of Phosphatidylserine on the Surface of Apoptotic Lymphocytes Triggers Specific Recognition and Removal by Macrophages" J. Immunol. 148:2207-2216 (1992).

Falkner and Zachau, "Expression of mouse immunoglobulin genes in monkey cells" Nature 298:286-288 (1982).

Field et al., "Purification of a RAS-Responsive Adenylyl Cyclase Complex from Saccharomyces cerevisiae by Use of an Epitope Addition Method" Molecular & Cellular Biology 8:2159-2165 (1988).

Fiers et al., "Complete Nucleotide Sequence of SV40 DNA" Nature 273:113-120 (May 11, 1978).

Fishwild et al., "High-Avidity Human IgG\153 Monoclonal Antibodies From a Novel Strain of Minilocus Transgenic Mice" Nature Biotechnology. 14(7):845-851 (Jul. 1996).

Fleer et al., "Stable Multicopy Vectors for High-Level Secretion of Recombinant Human Serum Albumin by Kluyveromyces Yeasts" Bio/Technology 9:968-975 (1991).

Fraser and Evan, "A License to Kill" Cell 85:781-784 (1996).

Gelb et al., "Pycnodysostosis: Refined Linkage and Radiation Hybrid Analyses Reduce the Critical Region to 2 cM at 1q21 and Map Two Candidate Genes" Human Genet. 98:141-144 (1996).

Gething and Sambrook, "Cell-surface Expression of Influenza Haemagglutinin from a Cloned DNA the RNA Gene" Nature 293:620-625 (Oct. 22, 1981).

Ghetie et al., "Homodimerization of tumor-reactive monoclonal antibodies markedly increases their ability to induce growth arrest or apoptosis of tumor cells" Proc. Natl. Acad. Sci. USA 94(14):7509-7514 (Jul. 8, 1997).

Glassy, M., "Production methods for generating human monoclonal antibodies" Human Antibodies & Hybridomas 4(4):154-165 (Oct. 1993).

Goding, "Production of Monoclonal Antibodies" Monoclonal Antibodies: Principles and Practice, Academic Press, pp. 59-103 (1986).

Goeddel et al., "Direct Expression in *Escherichia coli* of a DNA Sequence Coding for Human Growth Hormone" Nature 281:544-548 (Oct. 18, 1979).

Goeddel et al., "Synthesis of Human Fibroblast Interferon by *E. coli*" Nucleic Acids Research 8(18):4057-4074 (1980).

Goodwin et al., "Molecular Cloning and Expression of the Type 1 and Type 2 Murine Receptors for Tumor Necrosis Factor." Mol. Cell. Bio. 11:3020-3026 (1991).

Gorman et al., "The Rous Sarcoma Virus Long Terminal Repeat is a Strong Promoter When Introduced into a Variety of Eukaryotic Cells by DNA-Mediated Transfection" Proc. Natl. Acad. Sci. USA 79:6777-6781 (Nov. 1982).

Gough et al., "Molecular cloning of seven mouse immunoglobulin \153 chain messenger ribonucleic acids" Biochemistry 19:2702-2710 (1980).

Graham and van der Eb, "A New Technique for the Assay of Infectivity of Human Adenovirus 5 DNA" Virology 52:456-467 (1973).

Graham et al., "Characteristics of a Human Cell Line Transformed by DNA from Human Adenovirus Type 5" J. Gen. Virol. 36:59-72 (1977).

Gray et al., "Expression of Human Immune Interferon cDNA in *E. coli* and Monkey Cells" Nature 295:503-508 (Feb. 11, 1982).

Greenaway et al., "Human Cytomegalovirus DNA: BamHI, EcoRI and PstI Restriction Endonuclease Cleavage Maps" Gene 18:355-360 (1982).

Gruss and Dower, "Tower Necrosis Factor Ligand Superfamily: Involvement in the Pathology of Malignant Lymphomas" Blood 85:3378-3404 (1995).

Hale et al., "Demonstration of In Vitro and In Vivo Efficacy of Two Biologically Active Human Soluble TNF Receptors Expressed in *E. coli*." J. Cell. Biochem. (abstract only, suppl. 15F; p. 424) pp. 113 (1991).

Handbook of Monoclonal Antibodies, Ferrone et al. eds., Park Ridge, NJ:Noyes Publications, pp. 302-359 and Chapter 22 (1985).

Hess et al., "Cooperation of Glycolytic Enzymes" Advances in Enzyme Regulation, George Weber, New York:Pergamon Press vol. 7:149-167 (1968).

Hitzeman et al., "Isolation and Characterization of the Yeast 3-Phosphoglycerokinase Gene (PGK) by an Immunological Screening Technique" Journal of Biological Chemistry 255(24):12073-12080 (Dec. 25, 1980).

Hohmann et al., "Two different cell types have different major receptors for human tumor necrosis factor (TNF\141\nor)" Journal of Biological Chemistry 264(25):14927-14934 (1989).

Holland and Holland, "Isolation and Identification of Yeast Messenger Ribonucleic Acids Coding for Enolase, Glyceraldehyde-3-phosphate Dehydrogenase, and Phosphoglycerate Kinase" Biochemistry 17(23):4900-4907 (1978).

Hoogenboom and Winter, "By-Passing Immunisation: Human Antibodies from Synthetic Repertoires of Germline V\subH\nor Gene Segments Rearranged in Vitro" J. Mol. Biol. 227:381-388 (1992).

Hoogenboom, "Designing and optimizing library selection strategies for generating high-affinity antibodies" Trends in Biotechnology 15(2):62-70 (Feb. 1997).

Hopp et al., "A Short Polypeptide Marker Sequence Useful for Recombinant Protein Identification and Purification" Bio/Technology 6:1204-1210 (1988).

Hsiao and Carbon, "High-frequency Transformation of Yeast by Plasmids Containing the Cloned Yeast Arg4 Gene" Proc. Natl. Acad. Sci. USA 76:3829-3833 (1979).

Hsu et al., "TRADD-TRAF2 and TRADD-FADD interactions define two distinct TNF receptor 1 signal transduction pathways" Cell 84:299-308 (1996).

Hunter et al., "Preparation of Iodine 131 Labelled Human Growth Hormone of High Specific Activity" Nature 194:495-496 (1962).

Hymowitz et al., "Triggering Cell Death: The Crystal Structure of Apo2L/TRAIL in a Complex with Death Receptor 5." Molecular Cell. 4(4):563-571 (1999).

Iliades et al., "Triabodies: single chain Fv fragments without a linker form trivalent trimers" FEBS Letters 409(3):437-441 (Jun. 16, 1997).

Itoh et al., "The Polypeptide Encoded by the cDNA for Human Cell Surface Antigen Fas Can Mediate Apoptosis." Cell. 66:233-243 (1991).

Jakobovits et al., "Analysis of Homozygous Mutant Chimeric Mice: Deletion of the Immunoglobulin Heavy-Chain Joining Region Blocks B-cell Development and Antibody Production" Proc. Natl. Acad. Sci. USA 90:2551-2555 (Mar. 1993).

Jakobovits et al., "Germ-line Tranmission and Expression of a Human-Derived Yeast Artificial Chromosome" Nature 362:255-258 (Mar. 18, 1993).

Johnson et al., "Expression and Structure of the Human NGF Receptor" Cell 47:545-554 (1986).

Jones et al., "Replacing the Complementarity-Determining Regions in a Human Antibody with Those From a Mouse." Nature. 321:522-525 (May 29, 1986).

Jone, E., "Proteinase Mutants of Saccharomyces Cerevisiae" Genetics 85(1):23-33 (1977).

Jones, Y., "Cytokine Receptor Complexes Verses Cell Adhesion Interactions—Upping the Affinity" (Abstract No. M11.OA.002 presented at the XVIIIth IUCr, 1999.

Congress & General Assembly held in Glasgow, Scotland on Aug. 4-13, 1999.) pp. 133.

Kabat et al. Sequences of Proteins of Immunological Interest (NIH Publn. No. 91-3242), 5th edition, 1992.

Keown et al., "Methods for Introducing DNA into Mammalian Cells" Methods in Enzymology 185:527-537 (1990).

Kingsman et al., "Replication in Saccharomyces Cerevisiae of Plasmid pBR313 Carrying DNA from the Yeast trp1 Region" Gene 7:141 (1979).

Kitson et al., "A Death-Domain-Containing Receptor that Mediates Apoptosis" Nature 384:372-375 (1996).

Kohler and Milstein., "Continuous Cultures of Fused Cells Secreting Antibody of Predefined Specificity" Nature. 256:495-497 (1975).

Kohno et al., "A Second Tumor Necrosis Factor Receptor Gene Product Can Shed a Naturally Occurring Tumor Necrosis Factor Inhibitor." Proc. Natl. Acad. Sci. USA 87:8331-8335 (1990).

Koopman et al., "Annexin V for Flow Cytometric Detection of Phosphatidylserine Expression on B Cells Undergoing Apoptosis" Blood 84:1415-1420 (1994).

Kortt et al., "Single-chain Fv fragments of anti-neuraminidase antibody NC10 containing five- and ten-residue linkers form dimers and with zero-residue linker a trimer" Protein Engineering 10(4):423-433 (Apr. 1997).

Kozak, "An analysis of vertebrate mRNA sequences: intimations of translational control" Journal of Cell Biology 115:887-903 (1991).

Kozbor et al., "A Human Hybrid Myeloma for Production of Human Monoclonal Antibodies" The Journal of Immunology 133(6):3001-3005 (1984).

Krammer et al., "Regulation of Apoptosis in the Immune System" Curr. Op. Immunol. 6:279-289 (1994).

Kyriakis et al, "Sounding the Alarm: Protein Kinase Cascades Activated by Stress and Inflammation" Journal of Biological Chemistry 271:24313-24316 (1996).

Laimins et al., "Osmotic Control of kdp Operon Expression in *Escherichia coli*" Proc. Natl. Acad. Sci. USA 78(1):464-468 (Jan. 1981).

Lasky et al., "DNA sequence analysis of the type-common glycoprotein-D genes of herpes simplex virus types 1 and 2" DNA 3(1):23-29 (1984).

Lesslauer et al., "Bioactivity of recombinant human TNF receptor fragments" J. Cell. Biochem. (abstract only, Supplement 15F; P432) p. 115 (1991).

Lewis et al., "Cloning and Expression of cDNAs for Two Distinct Murine Tumor Necrosis Factor Receptors Demonstrate One Receptor is Species Specific." PNAS USA. 88:2830-2834 (1991).

Li et al., "Targeted Mutation of the DNA Methyltransferase Gene Results in Embryonic Lethality." Cell. 69:915-926 (Jun. 1992).

LIFESEQ Database EST Sequence Reference "1", 1998.

LIFESEQ Database EST Sequence Reference "2", 1998.

Liu et al., "Dissection of TNF Receptor 1 Effector Functions: JNK Activation is not Linked to Apoptosis While NF-\153\norB\nor Activation Prevents Cell Death" Cell 87:565-576 (1996).

Loetscher et al., "Molecular Cloning and Expression of the Human 55 kd Tumor Necrosis Factor Receptor" Cell 61:351-359 (1990).

Luckow et al., "Trends in the Development of Baculovirus Expression Vectors" Bio/Technology 6:47-55 (1988).

Lusky et al., "Bovine Papilloma Virus Contains an Activator of Gene Expression at the Distal End of the Early Transcription Unit" Molecular & Cellular Biology 3(6):1108-1122 (Jun. 1983).

Lutz-Freyermuth et al., "Quantitative Determination That One of Two Potential RNA-binding Domains of the A Protein Component if the U1 Small Nuclear Ribonucleoprotein Complex Binds with High Affinity to Stem-loop II of U1 RNA" Proc. Natl. Acad. Sci. USA 87:6393-6397 (1990).

MacFarlane et al., "Identification and Molecular Cloning of Two Novel Receptors for the Cytotoxic Ligand TRAIL" Journal of Biological Chemistry 272(41):25417-25420 (1997).

MacKay et al., "Differential Responses of Fibroblasts from Wild-Type and TNF-R55-Deficient Mice to Mouse and Human TNF-\141\nor Activation" J. Immunol. 153:5274-5284 (1994).

Maeda et al., "Production of Human \141-interferon in Silkworm Using a Baculovirus Vector" Nature 315:592-594 (Jun. 13, 1985).

Mage et al., "Preparation of Fab and F(ab')\sub2\nor Fragments from Monoclonal Antibodies" Monoclonal Antibody Production Techniques and Applications, New York:Marcel Dekker, Inc. pp. 79-97 (1987).

Mallett et al., "Characterization of the MRC OX40 Antigen of Activated CD4 Positive T Lymphocytes—a Molecule Related to Nerve Growth Factor Receptor" EMBO Journal 9:1063-1068 (1990).

Mammalian Cell Biotechnology: A Practical Approach, M. Butler, ed., IRL Press (1991).

Mansour et al., "Disruption of the Proto-oncogene int-2 in Mouse Embryo-derived Stem Cells: a General Strategy for Targeting Mutations to Non-selectable Genes" Nature 336:348-352 (1988).

Mantei et al., "Rabbit\142-globin mRNA Production in Mouse L Cells Transformed with Cloned Rabbit\142-globin Chromosomal DNA" Nature 281:40-46 (Sep. 6, 1979).

Marks et al., "By-Passing Immunization: Human Antibodies From V-Libraries Displayed On Phage" J. Mol. Biol. 222:581-597 (1991).

Marsters et al., "A Novel Receptor for Apo2L/TRAIL Contains a Truncated Death Domain" Current Biology 7:1003-1006 (1997).

Marsters et al., "Activation of Apoptosis by Apo-2 Ligand is Independent of FADD but Blocked by CrmA." Current Biology. 6(6):750-752 (1996).

Marsters et al., "Apo-3, A New Member of the Tumor Necrosis Factor Receptor Family, Contains a Death Domain and Activates Apoptosis and NF-\153B." Curr. Biol. 6(12):1669-1676 (1996).

Marsters et al., "Herpesvirus Entry Mediator, A Member of the Tumor Necrosis Factor Receptor (TNFR) Family, Interacts with Members of the TNFR-Associated Factor Family and Activated the Transcription Factors NF-\153\norB and AP-1." J. Bio. Chem. 272(22):14029-14032 (1997).

Marsters et al., "Interferon \147\nor Signals Via a High-Affinity Multisubunit Receptor Complex That Contains Two Types of Polypeptide Chain" Proc. Natl. Acad. Sci. USA 92:5401-5405 (1995).

Martin et al., "Cell-free Reconstitution of Fas-, UV Radiation- and Ceramide-induced Apoptosis" EMBO Journal 14(21):5191-5200 (1995).

Martin et al., "GAP Domains Responsible for Ras p21-Dependent Inhibition of Muscarinic Atrial K\sup+\nor Channel Currents" Science 255:192-194 (1992).

Mather et al., "Culture of Testicular Cells in Hormone-Supplemented Serum-Free Medium" Annals N.Y. Acad. Sci. 383:44-68 (1982).

Mather, J.P., "Establishment and Characterization of Two Distinct Mouse Testicular Epithelial Cell Lines" Biol. Reprod. 23:243-252 (1980).

Maxam et al., "Sequencing End-labeled DNA with Base-Specific Chemical Cleavages" Methods in Enzymology 65:499-560 (1980).

McCafferty et al., "Phage antibodies: filamentous phage displaying antibody variable domains" Nature 348:552-554 (1990).

Mendez et al., "Functional transplant of megabase human immunoglobulin loci recapitulates human antibody response in mice" Nature Genetics 15:146-156 (Feb. 1997).

Messing et al., "A System for Shotgun DNA Sequencing" Nucleic Acids Research 9(2):309-321 (1981).

Miller et al., "An Insect Baculovirus Host-Vector System for High-Level Expression of Foreign Genes" Genetic Engineering, Setlow et al., Plenum Publishing vol. 8:277-298 (1986).

Milstein and Cuello, "Hybrid Hybridomas and Their Use in Immunohistochemistry" Nature 305:537-540 (Oct. 1983).

Mongkolsapaya et al., "Structure of the TRAIL-DR5 complex reveals mechanisms conferring specificity in apoptotic initiation" Nature Structural Biology 6(11):1048-1053 (Nov. 1999).

Montgomery et al., "Herpes Simplex Virus-1 Entry into Cells Mediated by a Novel Member of the TNF/NGF Receptor Family" Cell 87(3):427-436 (1996).

Moore et al., "Apoptosis in CHO Cell Batch Cultures: Examination by Flow Cytometry" Cytotechnology 17:1-11 (1995).

Morrison et al., "Chimeric Human Antibody Molecules: Mouse Antigen-Binding Domains with Human Constant Region Domains" Proc. Natl. Acad. Sci. USA 81:6851-6855 (1984).

Morrison et al., "Transfer and expression of immunoglobulin genes" Annual Review of Immunology 2:239-256 (1984).

Morrison, S. L., "Transfectomas Provide Novel Chimeric Antibodies" Science 229:1202-1207 (Sep. 20, 1985).

Mulligan et al., "Expression of a Bacterial Gene in Mammalian Cells" Science 209:1422-1427 (Sep. 1980).

Munro, "Uses of chimaeric antibodies" Nature 312:597 (1984).

Munson and Rodbard, "LIGAND: A Versatile Computerized Approach for Characterization of Ligand-Binding Systems" Analytical Biochemistry 107:220-239 (1980).

Muzio et al., "FLICE, A Novel FADD-Homologous ICE/CED-3-like Protease, Is Recruited to the CD95 (Fas/APO-1) Death-Inducing Signaling Complex" Cell 85:817-827 (1996).

Nagata and Golstein, "The Fas Death Factor" Science 267:1449-1456 (1995).

Nagata, S., "Apoptosis by Death Factor." Cell. 88:355-365 (Feb. 1997).

NCBI/GenBank EST; Locus AA223122:(computer printout attached), 1998.

NCBI/GenBank EST; Locus AA232440:(computer printout attached), 1998.

NCBI/GenBank EST; Locus HS75A7R:(computer printout attached), 1998.

Neri et al., "Engineering recombinant antibodies for immunotherapy" Cell Biophysics 27(1):47-61 (Aug. 1995).

Neuberger et al., "Recombinant Antibodies Possessing Novel Effector Functions" Nature 312:604-608 (Dec. 13, 1984).

Nophar et al., "Soluble Forms of Tumor Necrosis Factor Receptors (TNF-Rs). The cDNA for the Type I TNF-R, cloned Using Amino Acid Sequence Data of its Soluble Form, Encodes Both the Cell Surface and a Soluble Form of the Receptor." EMBO Journal. 9:3269-3278 (1990).

Nygren, H., "Conjugation of Horseradish Peroxidase to Fab Fragments with Different Homobifunctional and Heterobifunctional Cross-Linking Reagents" The Journal of Histochemistry and Cytochemistry 30(5):407-412 (1982).

Olsson and Kaplan, "Human-human hybridomas producing monoclonal antibodies of predefined antigenic specificity" Proc. Natl. Acad. Sci. USA 77(9):5429-5431 (1980).

Osborne et al., "Transcription Control Region Within the Protein-coding Portion of Adenovirus E1A Genes" Molecular & Cellular Biology 4(7):1293-1305 (Jul. 1984).

Paborsky et al., "Mammalian Cell Transient Expression of Tissue Factor for the Production of Antigen" Protein Eng. 3(6):547-553 (1990).

Pain et al., "Preparation of Protein A-Peroxidase Monoconjugate Using a Heterobifunctional Reagent, and its Use in Enzyme Immunoassays" Journal of Immunological Methods 40:219-230 (1981).

Pan et al., "An Antagonist Decoy Receptor and a Death-Domain Containing Receptor for TRAIL." Science 277:815-818 (Aug. 1997).

Pan et al., "The Receptor for the Cytotoxic Ligand TRAIL." Science. 276:111-113 (Apr. 4, 1997).

Pavlakis et al., "Expression of Two Human Growth Hormone Genes in Monkey Cells Infected by Simian Virus 40 Recombinants" Proc. Natl. Acad. Sci. USA 78(12):7398-7402 (Dec. 1981).

Peetre et al., "A tumor necrosis factor binding protein is present in human biological fluids" European Journal of Haematology 41:414-419 (1988).

Pennica et al., "Human Tumour Necrosis Factor: Precursor Structure, Expression and Homology to Lymphotoxin" Nature 312:724-729 (1984).

Peppel and Beutler, "Chimeric TNF-Receptor-IgG Molecule Acts as Soluble Inhibitor of TNF Mediated Cytotoxicity" J. Cell. Biochem. (abstract only, Supplement 15F; P439) p. 118 (1991).

Peterson, N., "Recombinant antibodies: alternative strategies for developing and manipulating murine-derived monoclonal antibodies" Laboratory Animal Science 46(1):8-14 (Feb. 1996).

Pitti et al., "Induction of Apoptosis by Apo-2 Ligand, a New Member of the Tumor Necrosis Factor Cytokine Family" Journal of Biological Chemistry 271:12687-12690 (1996).

Pluckthun., "Antibodies From *Escherichia coli*." The Pharmacology of Monoclonal Antibodies: Handbook of Experimental Pharmacology., Rosenberg and Moore, eds., Berlin:Springer-Verlag, Chapter 11, vol. 113:269-315 (1994).

Presta et al., "Humanization of an Antibody Directed Against IgE" J. Immunol. 151(5):2623-2632 (Sep. 1, 1993).
Presta, L., "Antibody Engineering" Curr. Op. Struct. Biol. 2:593-596 (1992).
Rabidezeh et al., "Induction of Apoptosis by the Low-Affinity NGF Receptor" Science 261:345-348 (1993).
Radeke et al., "Gene Transfer and Molecular Cloning of the Rat Nerve Growth Factor Receptor." Nature. 325:593-597 (1987).
Raff, "Social Controls on Cell Survival and Cell Death" Nature 356:397-400 (1992).
Raven et al., "Cloning and Functional Analysis of a Novel Protein Which Binds To The p55 TNF Receptor Death Domain" Euro. Cytokine Network (abstract No. 82) 7:210 (Apr.-Jun. 1996).
Raven et al., "Cloning and Functional Analysis of a Novel Protein Which Binds to the p55 TNF Receptor Death Domain" Programmed Cell Death Meeting (abstract only) pp. 127 (Sep. 20-24, 1995).
Ray et al., "Viral Inhibition of Inflammation: Cowpox Virus Encodes an Inhibitor of the Interleukin-1\142\nor Converting Enzyme" Cell 69:597-604 (May 15, 1992).
Remington's Pharmaceutical Sciences, Oslo et al., eds., 16th edition, Mack Publishing Co. (1980).
Reyes et al, "Expression of Human \142\nor-interferon cDNA Under the Control of a Thymidine Kinase Promoter from Herpes Simlex Virus" Nature 297:598-601 (Jun. 17, 1982).
Rice and Baltimore, "Regulated expression of an immunoglobulin \ 153 gene introduced into a mouse lymphoid cell line" Proc. Natl. Acad. Sci. USA 79:7862-7865 (1982).
Riechmann et al., "Reshaping Human Antibodies for Therapy" Nature 332:323-327 (Mar. 24, 1988).
Rothe et al., "A novel family of putative signal transducers associated with the cytoplasmic domain of the 75 kDA tumor necrosis factor receptor" Cell 78:681-692 (1994).
Sachs et al., "Control of Programmed Cell Death in Normal and Leukemic Cells: New Implications for Therapy" Blood 82:15-21 (1993).
Sambrook et al. Molecular Cloning: A Laboratory Manual, Second edition, New York:Cold Spring Harbor Laboratory Press (1989).
Schall et al., "Molecular Cloning and Expression of a Receptor for Human Tumor Necrosis Factor" Cell 61:361-370 (1990).
Schmid et al., "DNA Fragmentation: Manisfestation of Target Cell Destruct. Mediated by Cytotoxic T-cell Lines, Lymphotoxin-Secreting Helper T-cell Clones, and Cell-Free Lymphotoxin-Containing Supernatant." PNAS USA 83:1881-1885 (1986).
Schneider et al., "Characterization of Two Receptors for TRAIL." FEBS Letters. 416:329-334 (1997).
Screaton et al., "TRICK2, A New Alternatively Spliced Receptor that Transduces the Cytotoxic Signal From TRAIL." Current Biology. 7:693-696 (1997).
Seckinger et al., "Purification and biologic characterization of a specific tumor necrosis factor \141 Inhibitor" Journal of Biological Chemistry 264:11966-11973 (1989).
Sharon et al., "Expression of a V\subH\norC\sub\153\nor chimaeric protein in mouse myeloma cells" Nature 309:364-367 (1984).
Shaw et al., "A General Method for the Transfer of Cloned Genes to Plant Cells" Gene 23:315-330 (1983).
Sheridan et al., "Control of TRAIL-Induced Apoptosis by a Family of Signaling and Decoy Receptors" Science 277:818-821 (1997).
Shopes, "A Genetically Engineered Human IgG Mutant With Enhanced Cytolytic Activity." Journal of Immunology. 148(9):2918-2922 (1992).
Siebenlist et al., "E. coli RNA Polymerase Interacts Homologously with Two Different Promoters" Cell 20:269-281 (Jun. 1980).
Simonet et al., "Osteoprotegerin: A Novel Secreted Protein Involved in the Regulation of Bone Density" Cell 89:309-319 (1997).
Sims et al., "A Humanized CD18 Antibody Can Block Function Without Cell Destruction" The Journal of Immunology 151(4):2296-2308 (Aug. 1993).
Skinner et al., "Use of the Glu-Glu-Phe C-Terminal Epitope for Rapid Purification of the Catalytic Domain of Normal and Mutant ras GTPase-activating Proteins." J. Bio. Chem. 266:14163-14166 (1991).

Smith et al., "A Receptor for Tumor Necrosis Factor Defines an Unusual Family of Cellular and Viral Proteins" Science 248:1019-1023 (1990).
Smith et al., "Cardica Glycoside-Specific Antibodies in the Treatment of Digitalis Intoxication" Antibodies in Human Diagnosis and Therapy pp. 365-389 (1977).
Smith et al., "T2 Open Reading Frame From the Shope Fibroma Virus Encodes a Soluble Form of the TNF Receptor." Biochem. & Biophys. Res. Comm. 176:335-342 (1991).
Smith et al., "The TNF receptor superfamily of cellular and viral proteins: activation, costimulation, and death" Cell 76:959-962 (1994).
Soderlind et al., "Phage display technology in antibody engineering: design of phagemid vectors and in vitro maturation systems" Immunological Reviews 130:109-124 (Dec. 1992).
Sojar and Bahl, "A Chemical Method for the Deglycosylation of Proteins" Archives of Biochemistry & Biophysics 259:52-57 (1987).
Sojar et al., "A Chemical Method for the Deglycosylation of Proteins" Archives of Biochemistry & Biophysics 259(1):52-57 (1987).
Southern et al., "Transformation of Mammalian Cells to Antibiotic Resistance with a Bacterial Gene Under Control of the SV40 Early Region Promoter" J. Molec. Appl. Genet. 1:327-341 (1982).
Stamenkovic et al., "A B-Lymphocyte Activation Molecule Related to the Nerve Growth Factor Receptor and Induced by Cytokines in Carcinomas." EMBO Journal. 8(5):1403-1410 (1989).
Steinitz et al., "EB virus-induced B lymphocyte cell lines producing specific antibody" Nature 269(5627):420-422 (Sep. 29, 1977).
Steller, H., "Mechanisms and Genes of Cellular Suicide" Science 267:1445-1449 (1995).
Stevenson et al., "A Chimeric Antibody With Dual Fc Regions (bisFabFc) Prepared by Manipulations at the IgG Hinge." Anti-Cancer Drug Design. 3(4):219-230 (1989).
Stinchcomb et al., "Isolation and Characterisation of a Yeast Chromosomal Replicator" Nature 282:39 (Nov. 1, 1979).
Suda et al., "Molecular Cloning and Expression of the Fas Ligand, a Novel Member of the Tumor Necrosis Factor Family" Cell 75:1169-1178 (1993).
Sugden et al., "A Vector that Replicates as a Plasmid and Can Be Efficiently Selected in B-Lymphoblasts Transformed by Epstein-Barr Virus" Molecular & Cellular Biology 5:410-413 (1985).
Suresh et al., "Bispecific Monoclonal Antibodies from Hybrid Hybridomas" Methods in Enzymology 121:210-228 (1986).
Suva et al., "A parathyroid hormone-related protein implicated in malignant hypercalcemia: cloning and expression" Science 237(4817):893-896 (Aug. 1987).
Suva, L.J. et al., "A Parathyroid Hormone-Related Protein Implicated in Malignant Hypercalcemia: Cloning and Expression" Science 237:893-896 (1987).
Takao et al., "Novel DNA Polymorphism in the Mouse Tumor Necrosis Factor Receptors Type 1 and Type 2" Immunogenetics 37:199-203 (1993).
Tartaglia et al., "A novel domain within the 55 kd TNF receptor signals cell death" Cell 74(5):845-853 (1993).
Tewari and Dixit, "Fas- and Tumor Necrosis Factor-induced Apoptosis Is Inhibited by the Poxvirus crmA Gene Product" Journal of Biological Chemistry 270:3255-3260 (1995).
Tewari and Dixit, "Recent Advances in Tumor Necrosis Factor and CD40 Signaling" Curr. Op. Genet. Develop. 6:39-44 (1996).
Tewari et al., "Yama/CPP32\142\nor, a Mammalian Homolog of CED-3, Is a CrmA-Inhibitable Protease That Cleaves the Death Substrate Poly(ADP-Ribose) Polymerase" Cell 81:801-809 (1995).
Thomas and Capecchi, "Site-Directed Mutagenesis by Gene Targeting in Mouse Embryo-Derived Stem Cells." Cell. 51:503-512 (Nov. 1987).
Thomas, P., "Hybridization of Denatured RNA and Small DNA Fragments Transferred to Nitrocellulose" Proc. Natl. Acad. Sci. USA 77(9):5201-5205 (Sep. 1980).
Thompson, "Apoptosis in the Pathogenesis and Treatment of Disease" Science 267:1456-1462 (1995).
Thotakura and Bahl, "Enzymatic Deglycosylation of Glycoproteins" Meth. Enzymol. 138:350-359 (1987).
Tissue Culture, Kruse and Patterson, eds., New York:Academic Press (1973).

Traunecker et al., "Bispecific Single Chain Molecules (Janusins) Target Cytotoxic Lymphocytes on HIV Infected Cells" EMBO Journal 10(12):3655-3659 (1991).
Traunecker et al., "Highly Efficient Neutralization of HIV with Recombinant CD4-immunoglobulin Molecules" Nature 339:68-70 (1989).
Tschumper and Carbon, "Sequence of a Yeast DNA Fragment Containing a Chromosomal Replicator and the TRP1 Gene" Gene 10:157-166 (1980).
Upton et al., "Myxoma Virus Expresses a Secreted Protein with Homology to the Tumor Necrosis Factor Receptor Gene Family that Contributes to Viral Virulence." Virology. 184:370-382 (1991).
Upton et al., "Tumorigenic Poxviruses: Genomic Organization and DNA Sequence of the Telomeric Region of the Shope Fibroma Virus Genome." Virology. 160:20-30 (1987).
Urlaub and Chasin, "Isolation of Chinese Hamster Cell Mutants Deficient in Dihydrofolate Reductase Activity" Proc. Natl. Acad. Sci. USA 77(7):4216 (Jul. 1980).
Van den Berg et al., "Kluyveromyces as a Host for Heterologous Gene Expression: Expression and Secretion of Prochymosin" Bio/Technology 8:135 (1990).
Van Solingen et al., "Fusion of Yeast Spheroplastes" J. Bact. 130:946-947 (1977).
Vaughan et al., "Human Antibodies With Sub-nanomolar Affinities Isolated From a Large Non-immunized Phage Display Library" Nature Biotechnology 14:309-314 (1996).
Verhoeyen et al., "Reshaping Human Antibodies: Grafting an Antilysozyme Activity" Science 239:1534-1536 (Mar. 25, 1988).
Verma et al., "Rel/NF-\153\norB\nor/I\153\norB\nor Family: Intimate Tales of Association and Dissociation" Genes Develop. 9:2723-2735 (1995).
von Bulow and Bram, "NF-AT Activation Induced by a CAML-Interacting Member of the Tumor Necrosis Factor Receptor Superfamily" Science 278:138-141 (1997).
Vukicevic et al., "Induction of nephrongenic mesenchyme by osteogenic protein 1 (bone morphogenetic protein 7)" Proc. Natl. Acad. Sci. 93:9021-9026 (1996).
Walczak et al., "TRAIL-R2: A Novel Apoptosis-Mediating Receptor for TRAIL." EMBO Journal. 16(17):5386-5397 (1997).
Watanabe-Fukunaga et al., "Lymphoproliferation Disorder in Mice Explained by Defects in Fas Antigen that Mediates Apoptosis" Nature 356:314-317 (1992).
Welcher et al., "Nerve growth factor binding domain of the nerve growth factor receptor" Proc. Natl. Acad. Sci. USA 88:159-163 (1991).
Wells et al., "Cassette Mutagenesis: An Efficient Method for Generation of Multiple Mutations at Defined Sites" Gene. 34(2-3):315-323 (1985)..
Wells, J. et al., "Importance of Hydrogen-Bond Formation in Stabilizing the Transition State of Subtilisin" Philos. Trans. Royal Soc. London Ser. A 317:415-423 (1986).
Wiley et al., "Identification and Characterization of a New Member of the TNF Family that Induces Apoptosis" Immunity 3:673-682 (1995).
Winter et al., "Making antibodies by phage display technology" Annual Review of Immunology 12:433-455 (1994).
Wolff et al., "Monoclonal antibody homodimers: enhanced antitumor activity in nude mice" Cancer Research 53(11):2560-2565 (1993).
Wong et al., "TRANCE Is a Novel Ligand of the Tumor Necrosis Factor Receptor Family That Activates c-Jun N-terminal Kinase in T Cells." J. Bio. Chem. 272(40):25190-25194 (Oct. 3, 1997).
Wu et al., "Killer/DR5 is a DNA Damage-Inducible p53-Regulated Death Receptor Gene." Nature Genetics. 17:141-143 (1997).
Yan and Chao, "Disruption of Cysteine-rich repeats of the p75 nerve growth factor receptor leads to loss of ligand binding" Journal of Biological Chemistry 266:12099-12104 (1991).
Yaniv, M., "Enhancing Elements for Activation of Eukaryotic Promoters" Nature 297(6):17-18 (May 1982).
Yonehara et al., "A Cell-Killing Monoclonal Antibody (Anti-Fas) to a Cell Surface Antigen Co-Downregulated with the Receptor of Tumor Necrosis Factor." Journal of Experimental Medicine 169:1747-1756 (1989).

Zheng et al., "Induction of Apoptosis in Mature T Cells by Tumor Necrosis Factor" Nature 377:348-351 (1995).
Zola, H., "Using Monoclonal Antibodies: Soluble Antigens" Monoclonal Antibodies: A Manual of Techniques, CRC Press, Chapter 6, pp. 147-158 (1987).
Zoller and Smith, "Oligonucleotide-Directed Mutagenesis Using M13-Derived Vectors: An Efficient and General Procedure for the Production of Point Mutations in Any Fragment of DNA" Nucl. Acids Res. 10(20):6487-6500 (1982).
Zoller, M. & Smith, M., "Oligonucleotide-directed mutagenesis using M13-derived vectors: an efficient and general procedures for the production of point mutations in any fragment of DNA" Nucl. Acids Res. 10:6487-6500 (1982).
U.S. Appl. No. 08/857,216, filed May 15, 1997, Ashkenazi, Avi.
U.S. Appl. No. 09/020,746, filed Jan. 16, 1996, Ashkenazi, Avi.
U.S. Appl. No. 09/079,029, filed May 14, 1998, Adams et al.
U.S. Appl. No. 09/096,637, filed Jun. 12, 1998, Ashkenazi, Avi.
U.S. Appl. No. 09/396,710, filed Sep. 15, 1999, Avi Ashkenazi.
U.S. Appl. No. 09/828,739, filed Apr. 9, 2001, Ashkenazi, Avi.
U.S. Appl. No. 10/005,842, filed Dec. 7, 2001, Jian Ni et al.
U.S. Appl. No. 10/052,798, filed Nov. 2, 2001, Adams, Camellia.
U.S. Appl. No. 10/288,917, filed Nov. 6, 2002, Adams, Camellia.
U.S. Appl. No. 10/423,448, filed Apr. 25, 2003, Adams, Camellia.
U.S. Appl. No. 10/627,429, filed Jul. 25, 2003, Adams, Camellia.
U.S. Appl. No. 10/648,825, filed Aug. 27, 2003, Jian Ni et al.
U.S. Appl. No. 11/297,319, filed Dec. 9, 2005, Adams, Camellia.
U.S. Appl. No. 11/455,062, filed Jun. 15, 2006, Ashkenazi, Avi.
U.S. Appl. No. 11/297,326, filed Dec. 9, 2005, Adams, Camellia.
U.S. Appl. No. 11/483,978, filed Jul. 11, 2006, Adams, Camellia.
U.S. Appl. No. 60/046,615, filed May 15, 1997, Ashkenazi, Avi.
U.S. Appl. No. 60/072,481, filed Jan. 26, 1988, Chuntharapai et al.
U.S. Appl. No. 60/074,119, filed Feb. 9, 1998, Ashkenazi, Avi.
U.S. Appl. No. 60/089,253, filed Jun. 12, 1998, Ashkenazi, Avi.
U.S. Appl. No. 60/133,238, filed May 7, 1999, Jian Ni et al.
U.S. Appl. No. 60/148,939, filed Aug. 13, 1999, Jian Ni et al.
U.S. Appl. No. 60/413,747, filed Sep. 27, 2002, Jian Ni et al.
U.S. Appl. No. 60/406,307, filed Aug. 28, 2002, Jian Ni et al.
Alderson et al., "Fas Transduces Activation Signals in Normal T lymphocytes", J. Exp. Med., 178:2231-2235 (1993).
Alderson et al., "Regulation of apoptosis and T cell activation by Fax-specific mAb" International Immunology, 6(11): 1799-1806 (1994).
Altschul et al., "Basic Local Alignment Search Tool" J. Mol. Biol. 215, 403-410 (1990).
Armitage et al., Nature 357:80 (1992).
Ashkenazi, et al., "Induction of Apoptosis by APO-2 Ligand, a New Member of the Tumor Necrosis Factor Cytokine Family", European Cytokine Network 7:159(1996).
Basic Pharmacology 4$^{th}$ Edition, Chapter 1: General Pharmacology p. 1-32 (1996).
Beg, et al., An Essential Role for NF-kB in Preventing TNF-a-Induced Cell Death, Science 274:782-784 (1996).
Bennett et al., J. Biol. Chem. 269(19): 14211 (1994).
Brutlag et al., "Improved sensitivity of biological sequence database searches" CABIOS vol. 6 No. 3. pp. 237-245 (1990).
Caron, et al., "Engineered Humanized Dimeric Forms of IgG are More Effective Antibodies", Journal of Experimental Medicine 176:1191-1195 (Oct. 1992).
Carter et al., Neuron 18: 187-190 (1997).
Casaccia-Bonnefil et al., Nature 383: 716 (1996).
Chu, G., Cellular Responses to Cisplatin, J. Bio. Chem. 269:2, 787-790 (1994).
Chuntharapai et al., J. Immunol. 166:4891 (2001).
Cifone, et al., "Apoptotic Signaling through CD95 (Fas/Apo-1) Activates an Acidic Sphingomyeliase" J. Exp. Med., 177:1547-1552 (1993).
Clewley and Arnold, "Megalign: The Multiple Alignment Module of LASERGENE" From: Methods in Molecular Biology, vol. 70: Sequence Data Analysis Guidebook, pp. 119-129 (1997).
Curtiss and Witzum, "A novel method for generating region-specific monoclonal antibodies to modified proteins. Application to the identification of human glucosylated low density lipoproteins", J. Clin. Invest. 72(4):1427-1438 (1983).

De Benedette, et al., "Role of 4-1BB ligand in costimulation", J. Exp. Med., 181:985 (1995).
Devereux et al., "A comprehensive set of sequence analysis programs for the VAX" Nucleic Acids Research vol. 12 No. 1:387-395 (1984).
Doctor et al., Cell Death and Differentiation 10:621-633 (2003).
Edelman, Gerald, M. "Antibody Structure and Molecular Immunology," Nobel Lecture, Dec. 12, 1972.
Eischen, et al., Comparison of Apoptosis in Wild-Type and Fas-resistance Cells: Chemotherapy-Induced Apoptosis is Not Dependant on Fas/Fas Ligand Interactions, Blood 90:935-943 (Aug. 1997).
Emery et al., "Osteoprotegerin Is a Receptor for the Cytotoxic Ligand TRAIL" J. Biol. Chem. 273:14363-14367 (1998).
Engelmann et al., "Antibodies to a Soluble Form of a Tumor Necrosis Factor (TNF) Receptor Have TNF-like Activity" J. of Biol. Chem. 265(24):14497-14504 (1990).
Espevik et al., "Characterization of Binding and Biological Effects of Monoclonal Antibodies against a Human Tumor Necrosis Factor Receptor" J. Exp. Med. 171:415-426 (1990).
Essentials of Pharmacology $2^{nd}$ Edition, Chapter 1: General Principles and Pharmacokinetics p. 1-33 (1996).
Fadeel et al., "Anti-Fas IgG1 antibodies recognizing the same epitope of Fas/APO-1 mediate different biological effects in vitro" International Immunology, 9(2):201-209 (1996).
Feinstein, E., et al., The Death Domain: A Module Shared by Proteins with Diverse Cellular Functions, TIBS 20:342-344 (1995).
Feldman et al., "TNFα as a Therapeutic Target in Rheumatoid Arthritis" Circulatory Shock 43:179-184 (1994).
Frade et al., Nature 383:166 (1996).
Griffiths, et al. "Human anti-self antibodies with high specificity from phage display libraries", The EMBO J., 12:725-734 (1993).
Hess, S., A Novel Function of CD 40: Induction of Cell Death in Transformed Cells, J. Exp. Med. 183:159-167 (1996).
Higgins and Sharp, "Clustal: a package for performing multiple sequence alignment on a microcomputer" Gene. 73(1) 237-244 (1988).
Hofmann & Tschopp, The death domain motif found in Fas (Apo-1) and TNF receptor is present in proteins involved in apoptosis and axonal guidance, FEBS Letters, 371:321-323 (1995).
Hsu, H., The TNF Receptor-1 Associated Protein TRADD Signals Cell Death and NF-kB Activation, Cell, 81:495-504 (1995).
Huisman et al., "Paclitaxel Triggers Cell Death Primarily via Caspase-independent Routes in the Non-Small Cell Lung Cancer Cell Line NCI-H460," Clinical Cancer Research 8:596-606 (2002).
Itoh and Nagata, "A Novel Protein Domain Required for Apoptosis (Mutational Analysis of Human Fas Antigen" Journal of Biological Chemistry, vol. 268, No. 15, May 25, pp. 10932-10937 (1993).
James, K., "Human Monoclonal Antibody Technology," The Pharmacology of Monoclonal Antibodies: Handbook of Experimental Pharmacology, Rosenberg and Moore, eds., Berlin:Springer-Verlag, Chapter 1, vol. 113:3-22 (1994).
Johnson et al., "Signal Transduction Pathways Regulated by Mitogen-activated/Extracellular Respnse Kinase Kinase Kinase Induce Cell Death" J. Biol. Chem. 271:3229-3237 (1996).
Kabat et al., Attempts to locate residues in complementarity-determining regions of antibody combining sites that make contact with antigen, Proc. Nat. Acad. Sci., 73:617-619 (1976).
Kabat et al., Some correlations between specificity and sequence of the first complementarity-determining region segments of human Kappa light chains, PNAS 73: 4471-4473, 1976.
Kehoe & Seide, Immunoglobulin structure and function: genetic control of antibody diversity, J. Am. Vet. Med. Assoc. 181(10):1000-1004, (1982).
Kobayashi et al., "Specificity problem of polyclonal rabbit antibody" J. Clin. Pathol. 41:705-706, 1988.
Lippincott's Illustrated Reviews: Pharmacology $2^{nd}$ Edition, Chapter 2: Pharmacokinetics and Drug Receptors p. 17-26 (1997).
Liu, et al., Mechanism of antigen-driven selection in germinal centres, Nature, 342:929-931 (1989).
Locksley et al., "The TNF and TNF Receptor Superfamilies: Integrating Mammalian Biology" Cell 104:487-501 (Feb. 2001).

Mackay et al., "Lymphotoxin β Receptor Triggering Induced Activation of the Nuclear Factor κB Transcription Factor in Some Cell Types" J. Biol. Chem., 271(40): 24934-24938 (Oct. 4, 1996).
Maini et al., "Targeting TNFα for the therapy of rheumatoid arthritis" Clinical and Experimental Rheumatology 12 (Suppl. 11): 563-566 (1994).
Mapara, et al., APO-1 mediated apoptosis or proliferation in human chronic B lymphocytic leukemia: correlation with bcl-2 oncogene expression, Eur. J. Immunol. 23:702-708, 1993.
Mark et al., J. Biol. Chem. 269(14): 10720 (1994).
Morrison, et al., Analysis of receptor clustering on cell surfaces by imaging fluorescent particles, Biophys. J., 67(3):1280-1290 (1994).
Mühlenbeck et al., J. Biol. Chem. 275(41): 32208 (2000).
Naismith & Sprang, "Tumor Necrosis Factor Receptor Superfamily," J. Inflamm., 47:1-7 (1996).
Nakai and Kanehisa, "A Knowledge Base for Predicting Protein Localization Sites in Eukaryotic Cells" Genomics 14:897-911 (1992).
Novotny et al., Molecular Anatomy of the Antibody Binding Site, J. Biol. Chem., 258:14433-14437 (1983).
Ogasawara et al., Nature 364:806 (1993).
Prakash, V., et al. The Interaction of Vincristine wit Calf Brain Tubulin, J. Bio. Chem., 258:3, 1689-1697 (1983).
Reed, Amer. J. Path. 157(5):1415-1430 (2000).
Reed et al., Sci. STKE 2004, re9 (2004).
Rennert, et al., "Surface Lymphotoxin a/B complex is required for development of peripheral lymphoid organs," J. Exp. Med., 184:1999 (1996).
Ross, Elliott M., "Pharmacodynamics: Mechanisms of Drug Action and the Relationship Between Drug Concentration and Effect" Goodman & Gilman's The Pharmacological Basis Of Therapeutics, Ninth Edition, Chapter 2: pp. 29-41 (1996).
Sato, et al., A novel member of the TRAF family of putative signal transducing protein binds to the cytosolic domain of CD40, FEBS Letters 358:113-118 (1995).
Sevier, et al., Monoclonal Antibodies in Clinical Immunology, Clin. Chem., 27:1797-1806 (1981).
Sheehan et al., "Monoclonal Antibodies Specific for Murine p55 and p75 Tumor Necrosis Factor Receptors: Identification of a Novel In Vivo Role for p75" J. Exp. Med. 181:607-617 (1995).
Srivastava, "TRAIL/Apo-2l: Mechanisms and Clinical Applications in Cancer," Neoplasia 3:535-546 (2001).
Stedman's Medical Dictionary, $26^{th}$ Edition, p. 38 (1995).
Tartaglia et al., "The two different receptors for tumor necrosis factor mediate distinct cellular responses" Proc. Natl. Acad. Sci. USA 88:9292-9296 (Oct. 1991).
Tartaglia and Goeddel, "Tumor Necrosis Factor Receptor Signaling" Journal of Biological Chemistry vol. 267, No. 7, Issue of Mar. 5, pp. 4304-4307 (1992).
Trauth et al., "Monoclonal Antibody-Mediated Tumor Regression by Induction of Apoptosis" Science 245:300-305 (1989).
Tsubata, T., B-cell apoptosis induced by antigen receptor crosslinking is blocked by a T-cell, Nature 364:645-648 (1993).
Uckun et al., J. Biol. Chem. 266(26):17478 (1991).
Van Antwerp, D., et al., Suppression of TNF-a-Induced Apoptosis by NF-kB, Science 274:787-789 (1996).
Wallach et al., TIBS 20:342 (1995).
Wang, et al., TNF-and Cancer Therapy-Induced Apoptosis: Potentiation by Inhibition of NF-kB, Science 274:784-787 (1996).
Ware, C., Apoptosis mediated by TNF-related cytokine and receptor familes, J. Cell Biochem. 60:47 (1996).
Ware, C. et al., "Tumor Necrosis Factor-Related Ligands and Receptors" The Cytokine Handbook, $3^{rd}$ ed., pp. 549-592 (1998).
Yagita et al., "TRAIL and its receptors as targets for cancer therapy," Cancer Sci. 95:777-783 (2004).
Yelton & Scharff, "Monoclonal Antibodies", Am. Sci., 68:510-516 (1980).
Adams et al., "Adams Motions List," Oct. 20, 2005—Interference 105,361.
Ni et al., "Ni List of Intended Motions," Oct. 20, 2005—Interference 105,361.
Ni et al., "Ni Clarification of List of Intended Motions," Oct. 21, 2005—Interference 105,361.

Stipulation and Order of Dismissal with Prejudice; Case No. 07-526-SLR-MPT, Oct. 21, 2009.
Form AO 120 re: Stipulation and Order of Dismissal with Prejudice; Case No. 07-526-SLR-MPT, Oct. 21, 2009.
Stipulation and Order of Dismissal with Prejudice; Case No. 09-389-SLR-MPT, Oct. 21, 2009.
Form AO 120 re: Stipulation and Order of Dismissal with Prejudice; Case No. 09-389-SLR-MPT, Oct. 21, 2009.
Dismissal Order; Appeal from *Human Genome Sciences* v. *Genentech*, 2009-1182; Case No. 08-CV-166, Oct. 20, 2009.

* cited by examiner

```
  1 CCCACGCGTC CGCATAAATC AGCACGCGGC CGGAGAACCC CGCAATCTCT GGCCCCACAA AATACACCGA CGATGCCCGA TCTACTTTAA GGGCTGAAAC
    GGGTGCGCAG GCGTATTTAG TCGTGCGCCG GCCTCTTGGG GCGTTAGAGA CCGGGGTGTT TTATGTGGCT GCTACGGGCT AGATGAAATT CCCGACTTTG

101 CCACGGGCCT GAGAGACTAT AAGAGCCGTTC CCTACCGCCA TGGAACAACG GGACAGAAC GCCCCGGCCG CTTCGGGGGC CCGGAAAAGG CACGGCCCAG
    GGTGCCCGGA CTCTCTGATA TTCTCGGCAAG GGATGGCGGT ACCTTGTTGC CCCTGTCTTG CGGGGCCGGC GAAGCCCCCG GGCCTTTTCC GTGCCGGGTC
  1                                                                                    M  etGluGlnAr gGlyGlnAsn AlaProAlaA laSerGlyAl aArgLysArg HisGlyProGly

201 GACCCAGGGA GGGCGGGGGA GCCAGGCCTG CCCCAAGACC CTTGTGCTCG TTGTCGCCGC GGTCCCTGCTG TTGGTCTCAG CTGAGTCTGC
    CTGGGTCCCT CCGCGCCCCT CGGTCCGGAC GGGGTTCTGG GAACACGAGC AACACGGGCG CCAGGACGAC AACCAGAGTC GACTCAGACG
 22                      ProArgGl uAlaArgGly AlaArgProG lyLeuArgVa lProLysThr LeuValLeuV alValAlaAl aLeuValSerA laGluSerAla

301 TCTGATCACC CAACAAGACC TAGCTCCCCA GCAGAGAGCG GCCCCACAAC AAAAGAGGTC CAGCCCCTCA GAGGATTGT GTCCACCTGG ACACCATATC
    AGACTAGTGG GTTGTTCTGG ATCGAGGGGT CGTCTCTCGC CGGGGTGTTG TTTTCTCCAG GTCGGGAGT CTCCCTAACA CAGGTGGACC TGTGGTATAG
 55  LeuIleThr GlnGlnAspL euAlaProGl nArgArgAla AlaProGlnG lnLysArgSe rSerProSer GluGlyLeuC ysProProGl yHisHisIle

401 TCAGAAGACG GTAGAGATTG CATCTCCCTG AAATATGGAC AGGACTATAG CACTCACTGG AATGACCTCC TTTTCTGCTT GCGCTGCACC AGGTGTGATT
    AGTCTTCTGC CATCTCTAAC GTAGAGGACG TTTATACCTG TCCTGATATC GTGAGTGACC TTACTGGAGG AAAAGACGAA CGCGACGTGG TCCACACTAA
 88  SerGluAspD sIleSerCys lyArgAspCy sIleSerCys LysTyrGlyS lnAspTyrSe rThrHisTrp AsnAspLeuL euPheCysLe uArgCysThr ArgCysAspSer

501 CAGGTGAAGT GGAGCTAAGT CCCTGCACCA CGACCAGAAA CACAGTGTGT CAGTGCGAAG AAGGCACCTT CCGGGAAGAA GATTCCTCTG AGATGTGCCG
    GTCCACTTCA CCTCGATTCA GGGACGTGGT GCTGGTCTTT GTGTCACACA GTCACGCTTC TTCCGTGGAA GGCCCTTCTT CTAAGAGGAC TCTACACGGC
122   GlyGluVa lGluLeuSer ProCysThrT hrThrArgAs nThrValCys GlnCysGluG luGlyThrPh eArgGluGlu AspSerSerG luMetCysArg

601 GAAGTGCCGC ACAGGGTGTC CCAGAGGGAT GGTCAAGGTC CCAGTTCCAG GGTCTCCCTA CCACTAACAT GTGGGACCTC ACTGTAGCTT ACACAGGTGT CATCATCATA
    CTTCACGGCG TGTCCCACAG GGTCTCCCTA CCAGAGGGAT GGTCAAGGTC CCAGTTCCAG GGTCAAGGTC GACCCTGGAG TGACATTCGAA TGTGTCCACA AGAATCAGG TTCTTAGTCC ACACAGGTGT GTAGTAGTAT
155  LysCysArg ThrGlyCysP roArgGlyMe tValLysVal GlyAspCysT hrProTrpSe rAspIleGlu CysValHisL ysGluSerGl yIleIleIle

701 GGAGTCACAG TTGCAGCCGT AGTCTTTGATT GTGGCTGTGT TTGTTTGCAA GTCTTTACTG TGGAAGAAAG TCCTTCCTTA CCTGAAAGGC ATCTGCTCAG
    CCTCAGTGTC AACGTCGGCA TCAGAACTAA CACCGACACA AACAAACGTT CAGAAATGAC ACCTTCTTTC AGGAAGGAAT GGACTTTCCG TAGACGAGTC
188  GlyValThrV alAlaAlaVa lValLeuIle ValAlaValP heValCysLy sSerLeuLeu TrpLysLysV alLeuProTy rLeuLysGly IleCysSerGly
```

*FIG._1A*

```
801  GTGGTGGTGG GGACCCTGAG CGTGTGGACA GAAGCTCACA ACGACCTGGC CGTGAGGACA ATGTCCTCAA TGAGATCGTG AGTATCTTGC AGCCCACCCA
     CACCACCACC CCTGGGACTC GCACACCTGT CTTCGAGTGT TGCTGGACCG CACTCCTGT TACAGGAGTT ACTCTAGCAC TCATAGAACG TCGGGTGGGT
222  GlyGlyGl yAspProGlu ArgValAspA rgSerSerGl nArgProGly AlaGluAspA snValLeuAs nGluIleVal SerIleLeuG lnProThrGln

901  GGTCCCTGAG CAGGAAATGG AAGTTCCAGA GCCAGCAGAG CCAACAGGTG TCAACATGTT GTCCCCCGGG GAGTCAGAGC ATCTGCTGGA ACCGGCAGAA
     CCAGGGACTC GTCCTTTACC TTCAGGTCT CGGTCGTCTC GGTTGTCCAC AGTTGTACAA CAGGGGGCCC CTCAGTCTCG TAGACGACCT TGGCCGTCTT
255  ValProGlu GlnGluMetG luValGlnGl uProAlaGlu ProThrGlyV alAsnMetLe uSerProGly GluSerGluH isLeuLeuGl uProAlaGlu

1001 GCTGAAAGGT CTCAGAGGAG GAGGCTGCTG GTTCCAGCAA ATGAAGGTGA TCCCACTGAG ACTCTGAGAC AGTGCTTTGA TGACTTTGCA GACTGGTGTC
     CGACTTTCCA GAGTCCTCCC CTCCGACGAC CAAGGTCGTT TACTTCCACT AGGGTGACTC TGAGACTCTG TCACGAAACT ACTGAAACGT CTGAACCACG
288  AlaGluArgS erGlnArgAr gArgLeuLeu ValProAlaA snGluGlyAs pProThrGlu ThrLeuArgG lnCysPheAs pAspPheAla AspLeuValPro

1101 CCTTTGACTC CTGGGAGCCG CTCATGAGGA AGTTGGGCCT GAGATAAAGG TGGCTAAAGC ACACCCTGCT ACTCCGTGCC GGCCACAGGG ACACCTTGTA
     GGAACTGAG GACCCTCGGC GAGTACTCCT TCAACCCGGA GTACCTGTTA CTCTATTTCC ACCGATTCG TGTGGGACGA CGGGTGTCCC TGTGGAACAT
322  PheAspSe rTrpGluPro LeuMetArgL ysLeuGlyLe uMetAspAsn GluIleLysV alAlaLysAl aGluAlaAla GlyHisArgA spThrLeuTyr

1201 CACGATGCTG ATAAAGTGGG TCAACAAAAC CGGGCGAGAT GCCTCTGTCC ACACCCTGCT GGATGCCTTG GAGAGACGCTG GAGAGAGACT TGCCAAGCAG
     GTGCTACGAC TATTTCACCC AGTTGTTTTG GCCCGCTCTA CGGAGACAGG TGTGGGACGA CCTACGGAAC CTCTGCGACC CTCTCTCTGA ACGGTTCGTC
355  ThrMetLeu IleLysTrpV alAsnLysTh rGlyArgAsp AlaSerValH isThrLeuLe uAspAlaLeu GluThrLeuG lyGluArgLe uAlaLysGln

1301 AAGATTGAGG ACCACTTGTT GAGCTCTGGA AAGTTCATGT ATCTAGAAGG TAATGCAGAC TCTGCCTTGT CCTAAGTGTG ATTCTCTTCA GGAAGTGAGA
     TTCTAACTCC TGGTGAACAA CTCGAGACCT TTCAAGTACA TAGATCTTCC ATTACGTCTG AGACGGAACA GGATTCCACA TAAGAGAAGT CCTTCACTCT
388  LysIleGluA spHisLeuLe uSerSerGly LysPheMetT yrLeuGluGl yAsnAlaAsp SerAlaXaaS erOC*

1401 CCTTCCCTGG TTTACCTTTT TTCTGGAAAA AGCCCAACTG GACTCCAGTC CTGAGGTTCAG ACTAGGAAAG TGCCACAATT GTCACATGAC CGGTACTGGA AGAAACTCTC
     GGAAGGGACC AAATGGAAAA AAGACCTTTT TCGGGTTGAC CTGAGGTCAG CTGAGGTCAG TGATCCTTTC ACGGTGTTAA CAGTGTACTG GCCATGACCT TCTTTGAGAG

1501 CCATCCAACA TCACCCAGTG GATGGAACAT CCTGTAACTT TTCACTGCAC TTGGCATTAT TTTTATAAGC TGAATGTGAT AATAAGGACA CTATGGAAAT
     GGTAGGTTGT AGTGGGTCAC CTACCTTGTA GGACATTGAA AAGTGACGTG AACCGTAATA AAAATATTCG ACTTACACTA TTATTCCTGT GATACCTTTA
```

FIG._1B

```
1601 GTCTGGATCA TTCCGTTTGT GCGTACTTTG AGATTGGTT TGGGATGTCA TATCCTAATG TAAATGTTTT ATTTATTTAT
     CAGACCTAGT AAGGCAAACA CGCATGAAAC TCTAAACCAA ACCCTACAGT ACAAAAGTG TCGTGAAAAA ATAGGATTAC ATTACGAAA TAAATAAATA

1701 TTGGGCTACA TTGTAAGATC CATCTACAAA AAAAAAAAAA AAAAAAAAAG GGGGGCCGG ACTCTAGAGT CGCCGGCCGC GCCATGGCC
     AACCCGATGT AACATTCTAG GTAGATGTTT TTTTTTTTTT TTTTTTTTTC CCCGGCCGGC TGAGATCTCA GCTGGACGTC TTCGAACCGG CGGTACCGG
```

FIG._1C

```
  1 MEQRGQNAPAASGARKRHGPGPREARGARPGLRVPKTLVLVVAAVLLLVSAESALITQQD
 61 LAPQQRAAPQQKRSSPSEGLCPPGHHISEDGRDCISCKYGQDYSTHWNDLLFCLRCTRCD
121 SGEVELSPCTTRNTVCQCEEGTFREEDSPEMCRKCRTGCPRGMVKVGDCTPWSDIECVH
181 KESGIIIGVTVAAVVLIVAVFVCKSLLWKKVLPYLKGICSGGGDPERVDRSSQRPGAED
241 NVLNEIVSILQPTQVPEQEMEVQEPAEPTGVNMLSPGESEHLLEPAEAERSQRRRLLVPA
301 NEGDPTETLRQCFDDFADLVPFDSWEPLMRKLGLMDNEIKVAKAEAAGHRDTLYTMLIKW
361 VNKTGRDASVHTLLDALETLGERLAKQKIEDLLSSGKFMYLEGNADSALS
```

FIG._2A

```
Apo2       FADLVPFDSWEPLMRKLGLMDNEIKVAKAEAA--GHRDTL
DR4        FANIVPFDSWDQLMRQLDLTKNEIDVKRAGTA--GPGDAL
Apo3/DR3   VMDAVPARRWKEFVRTLGLREAEIEAVEIGR--FRDQQ
TNFR1      VVENVPPLRWKEFVRRIGLSDHEIDRLELQNGR-CLREAQ
Fas/Apo1   IAGVMTLSQVEKGFVRKNGVNEAKIDEIKNDNVQDTAEQKV

Apo2       YTMLIKWVNKTGRD-ASVHTLLDALETLGERLAKQKIED
DR4        YAMLMKWVNKTGRN-ASIRTLLDALERMEERHAKEIQD
Apo3/DR3   YEMLKRWRQQQP--AGLGAVYALERMGLDGCVEDLRS
TNFR1      YSMLATWRRRTPRREATLELGRVLRDMLGCLEDIEE
Fas/Apo1   -QLLRNWHQLHGKKEAY-DTLIKDLKKANLCTLAEKIQT
```

FIG._2B

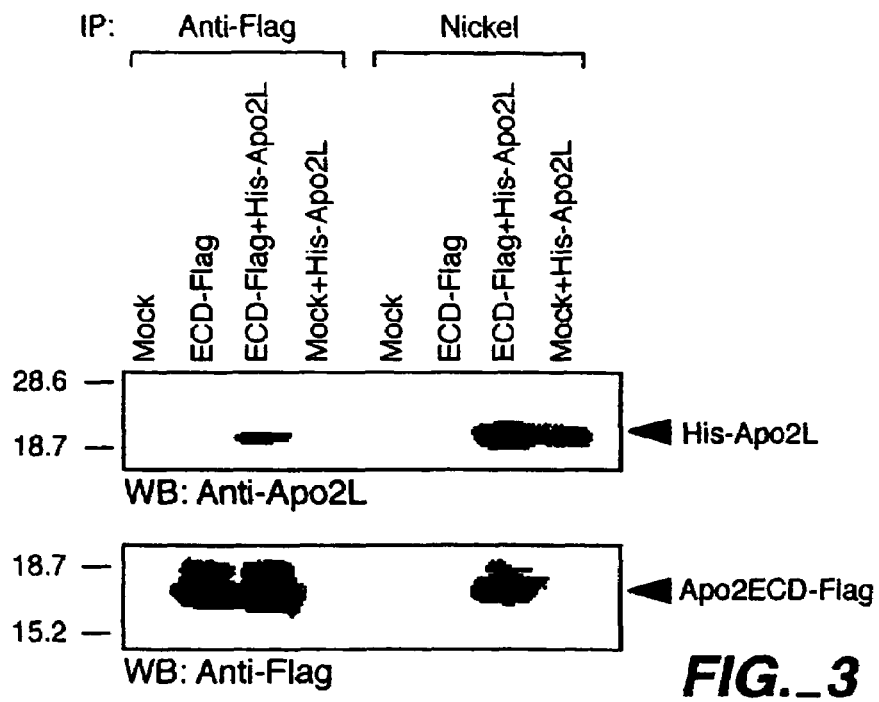
FIG._3
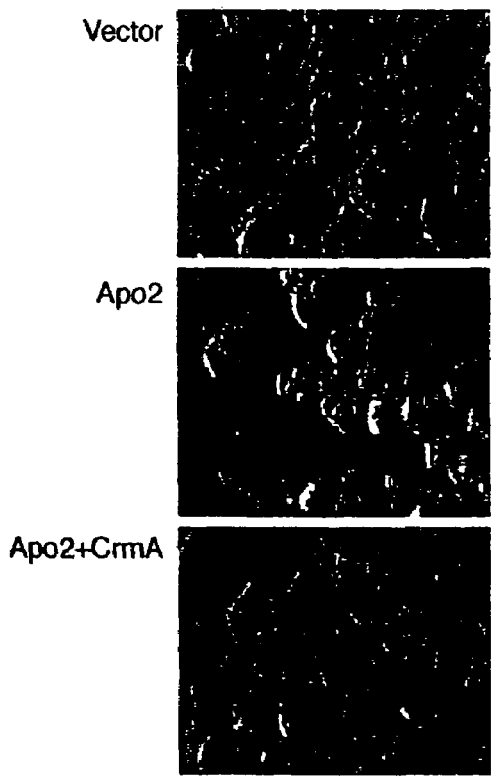
FIG._4A
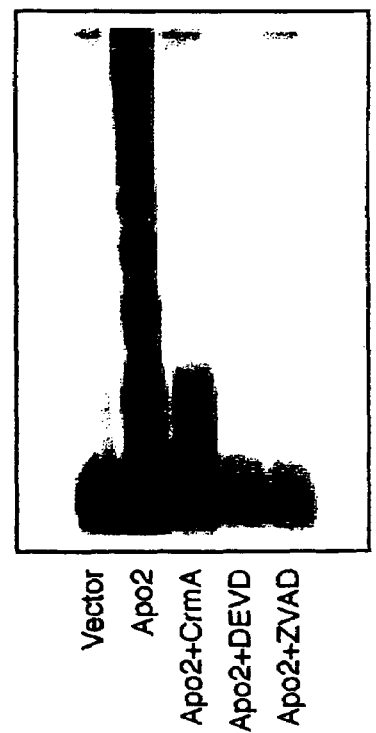
FIG._4B

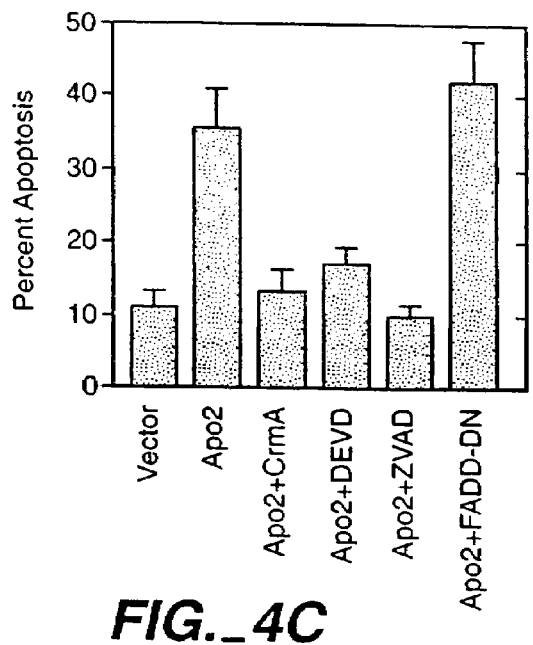
FIG._4C
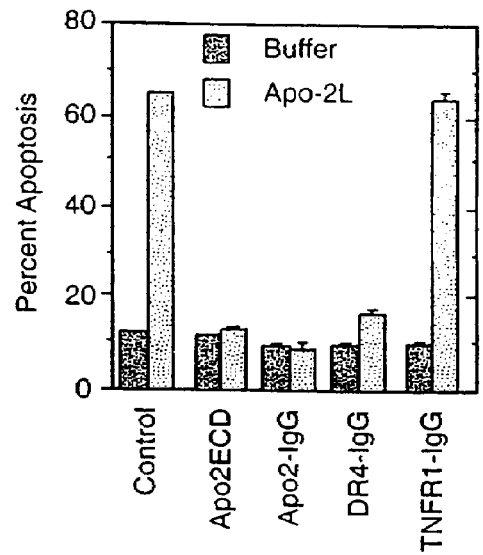
FIG._4D
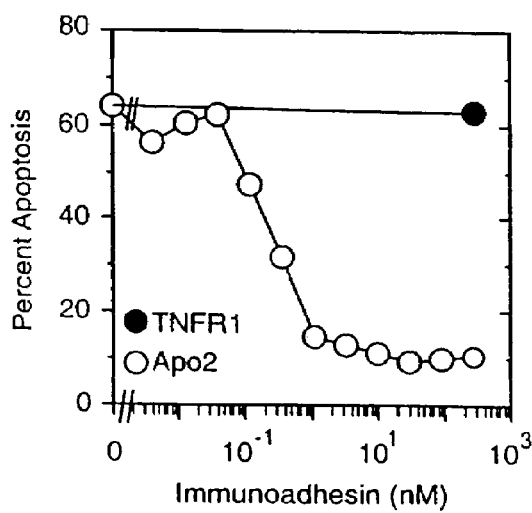
FIG._4E
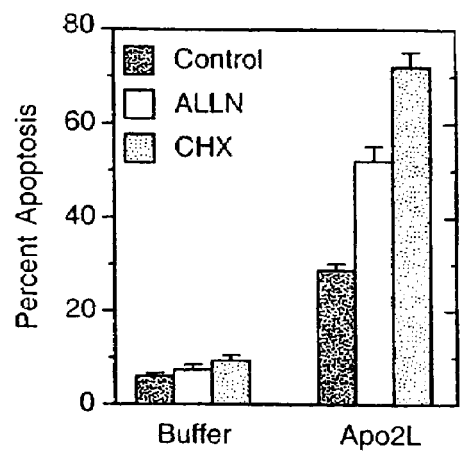
FIG._5C

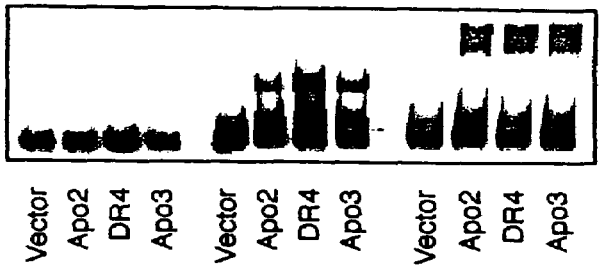
FIG._5A
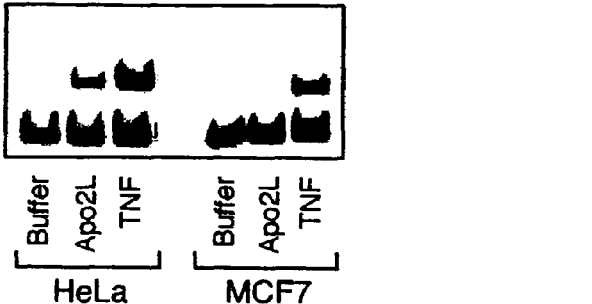
FIG._5B
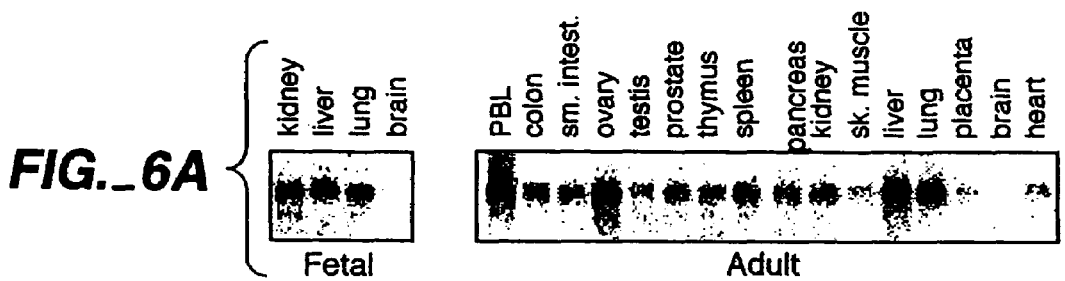
FIG._6A
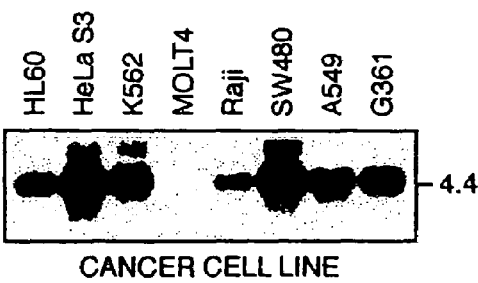
FIG._6B

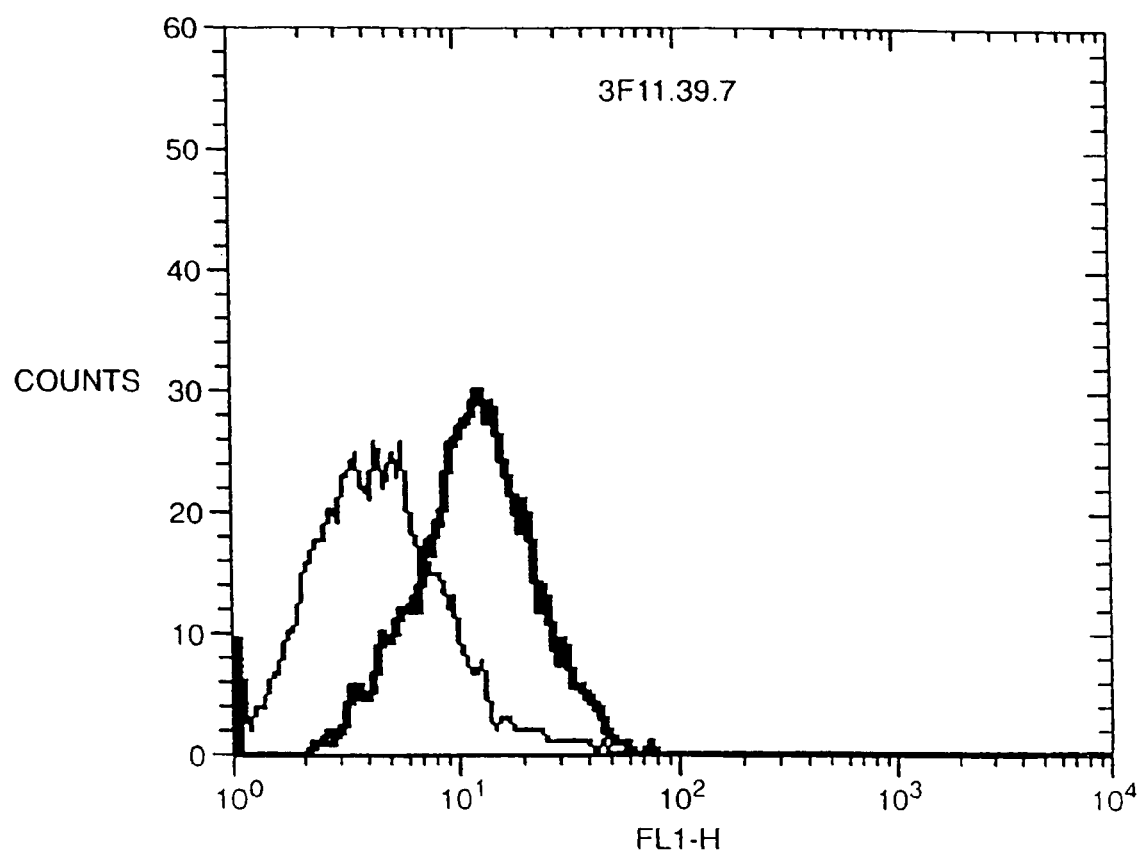
FIG._7

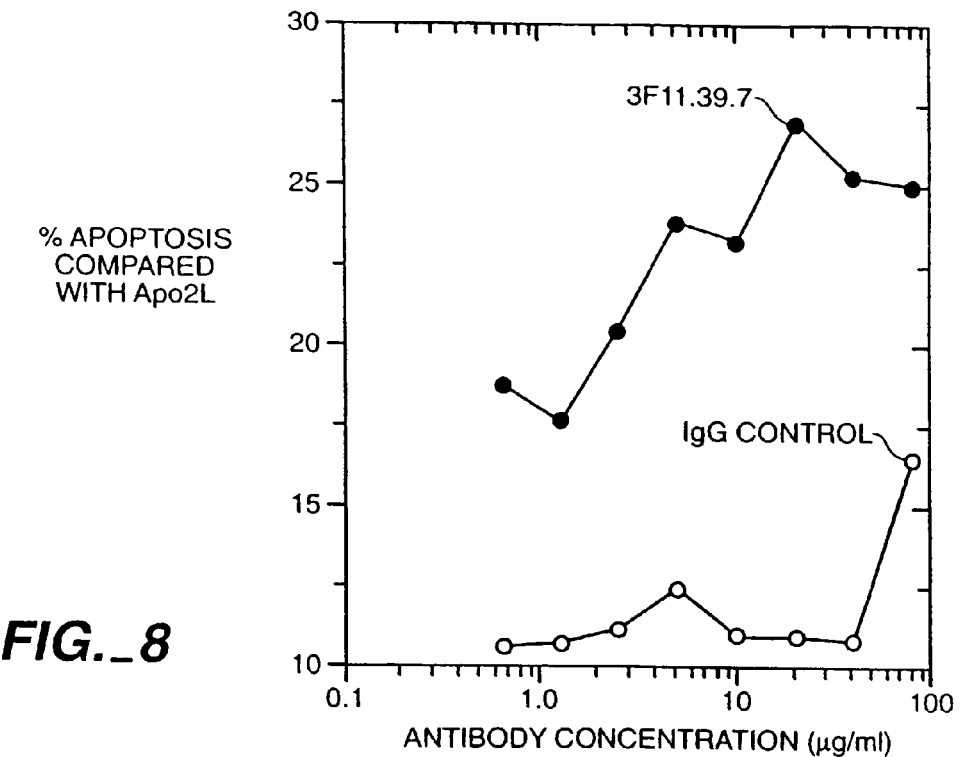
FIG._8
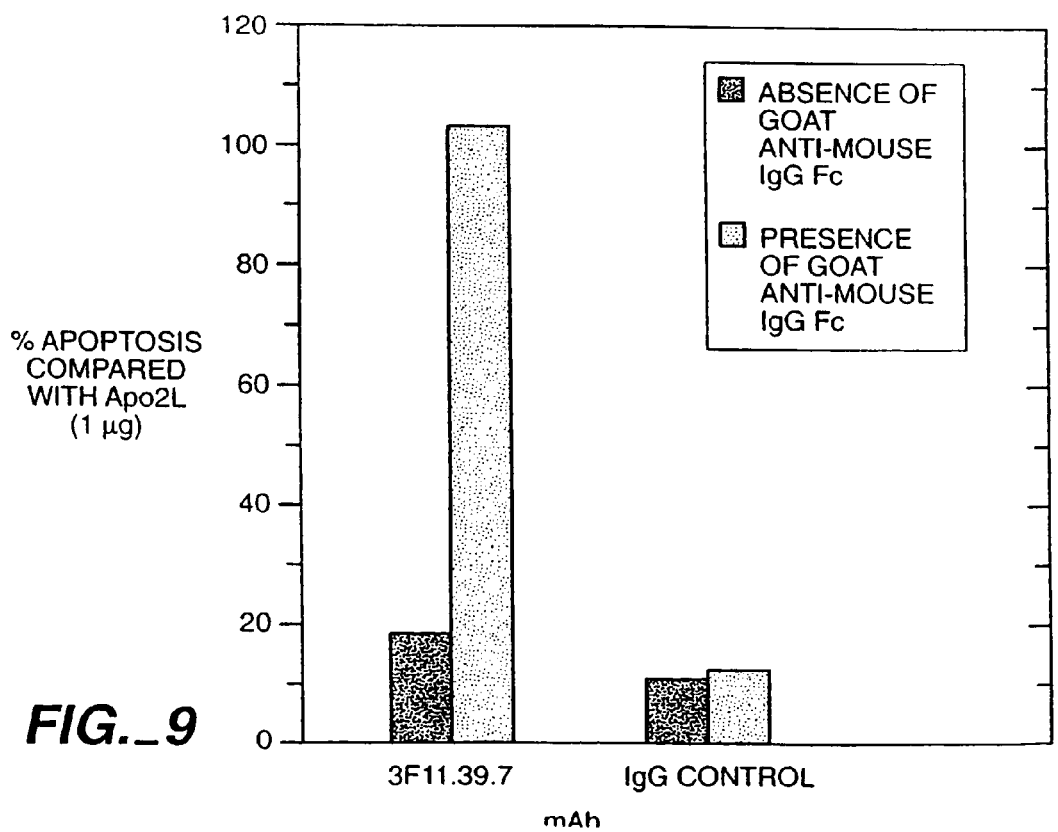
FIG._9

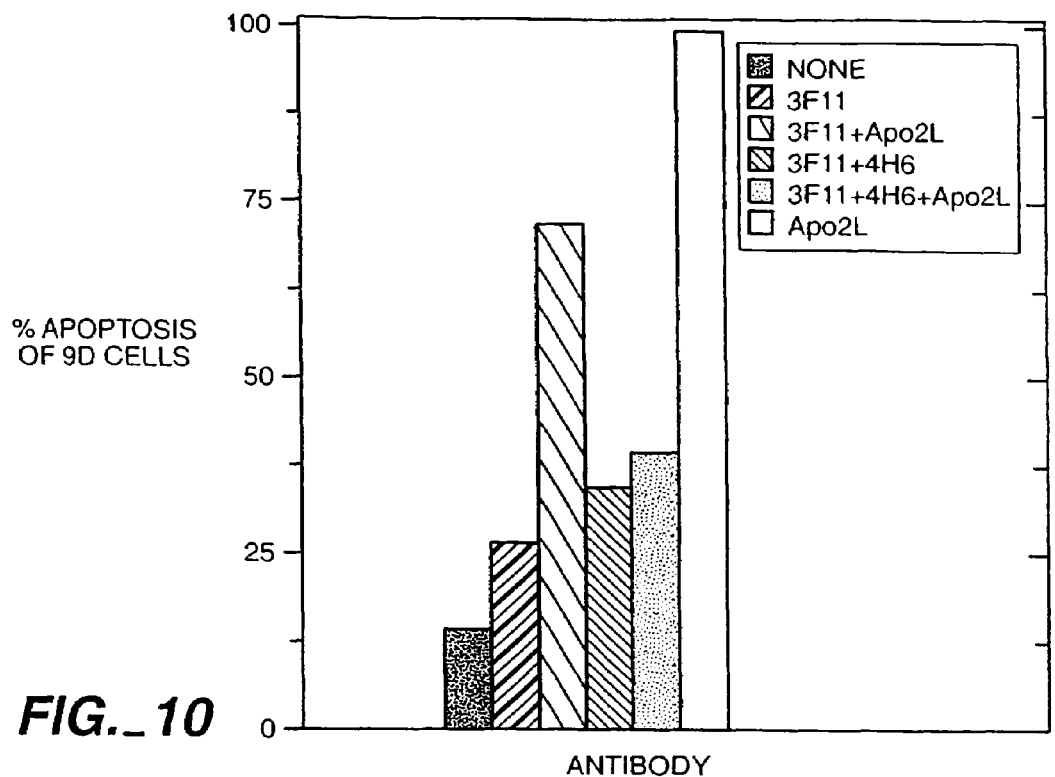
FIG._10
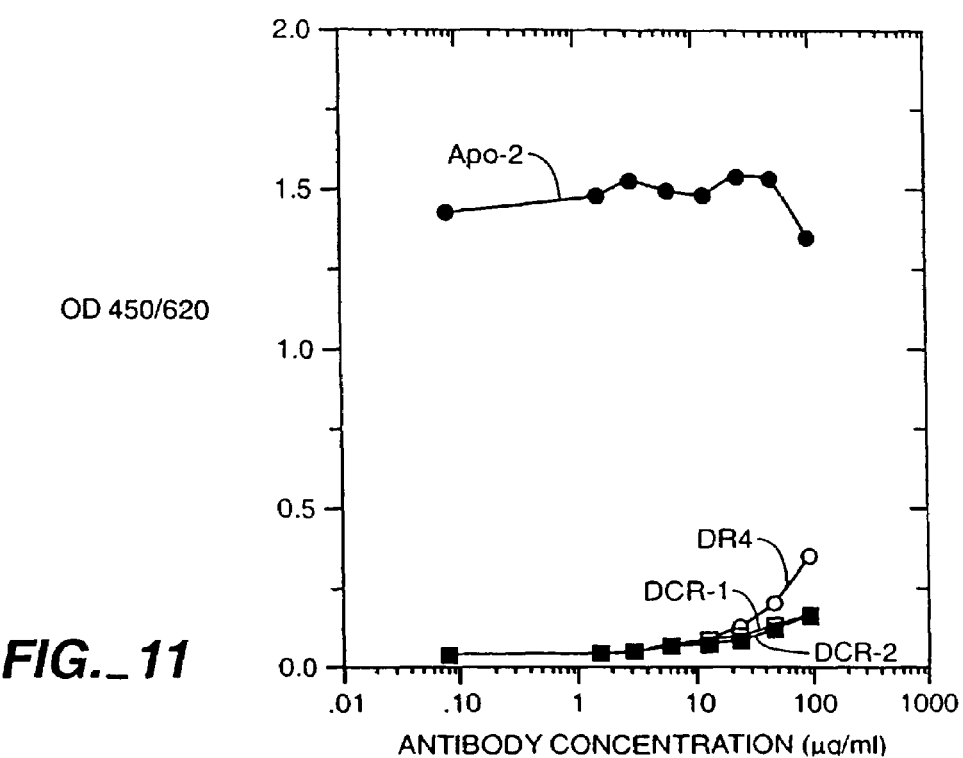
FIG._11

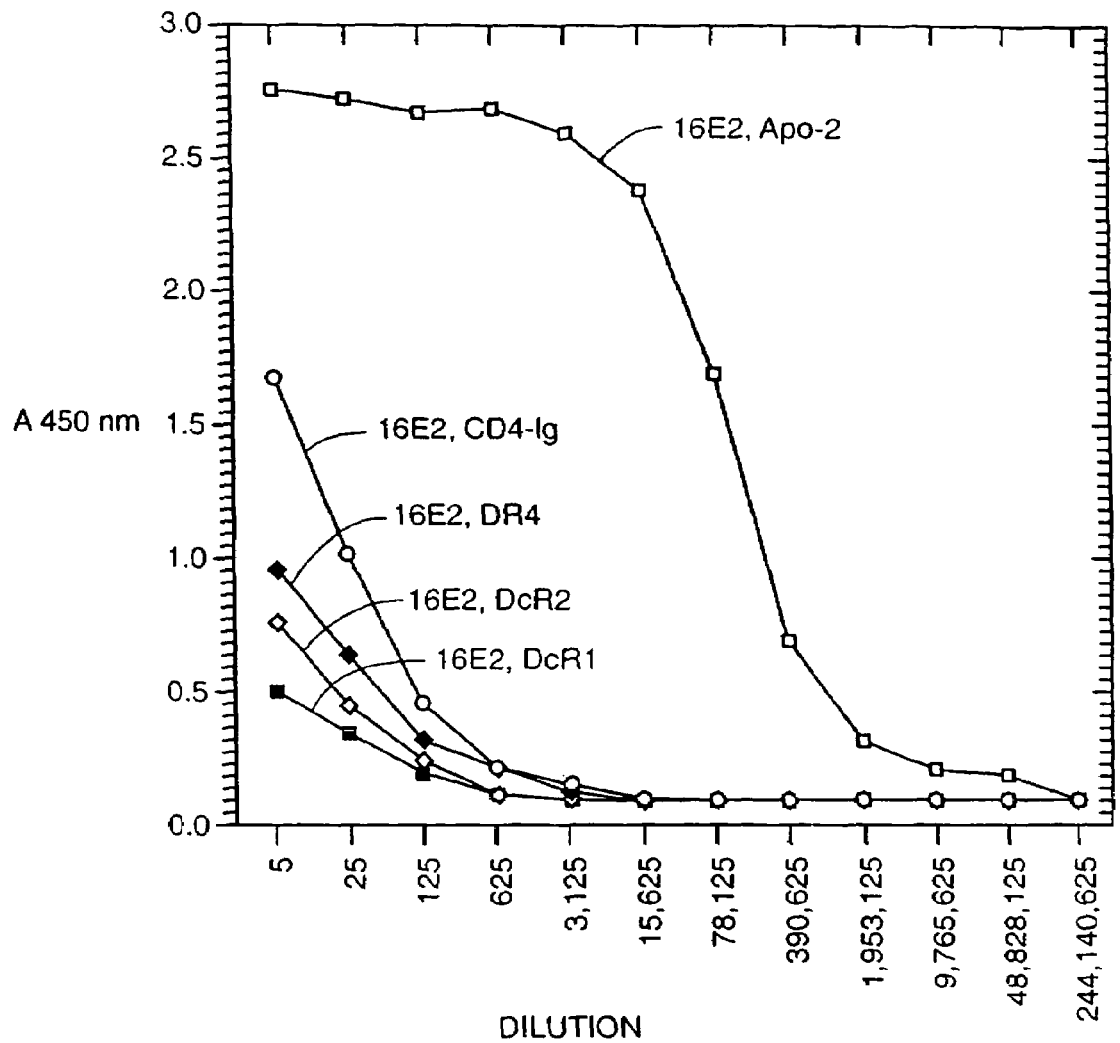
FIG._12A

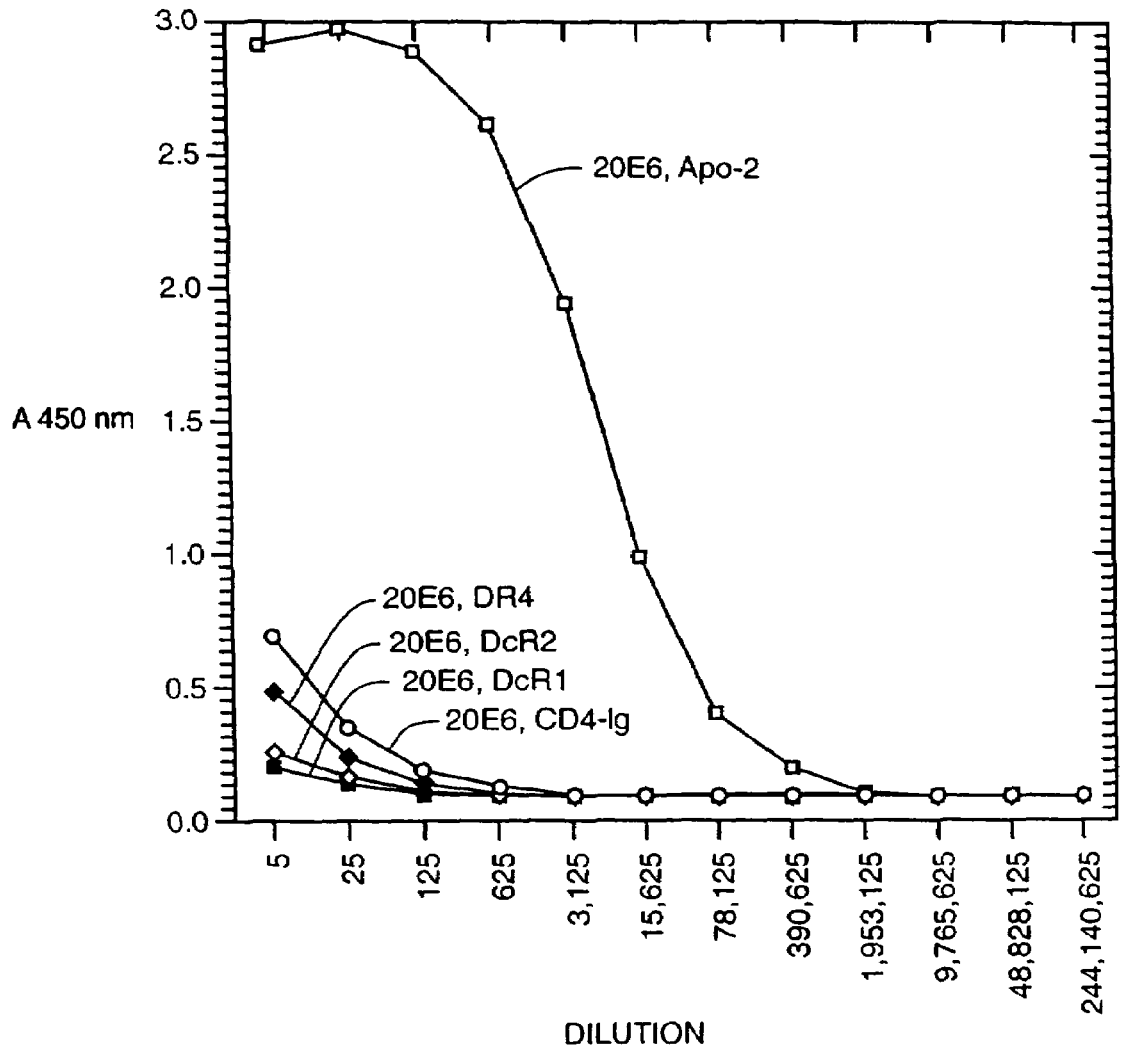
FIG._12B

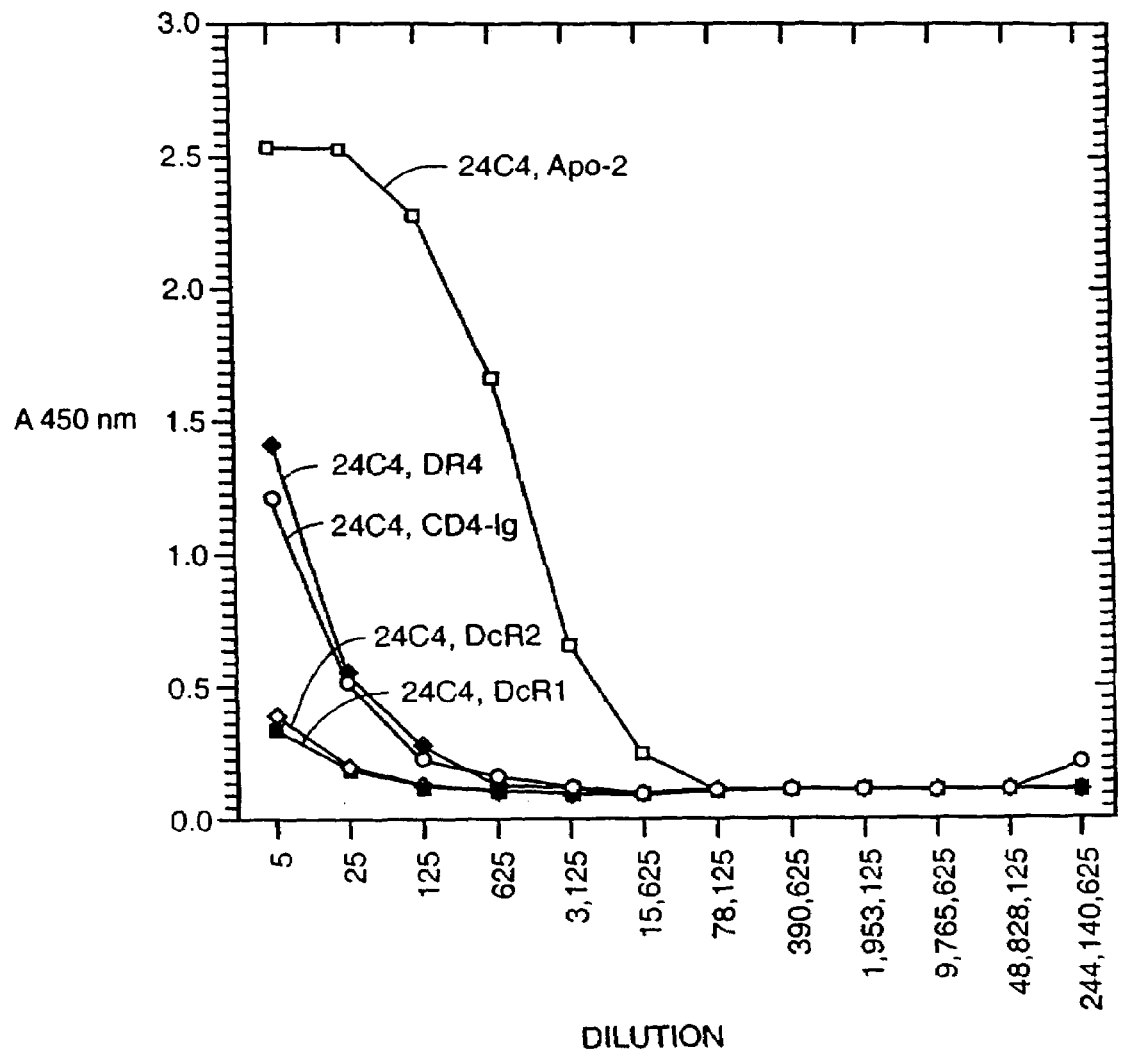
FIG._12C

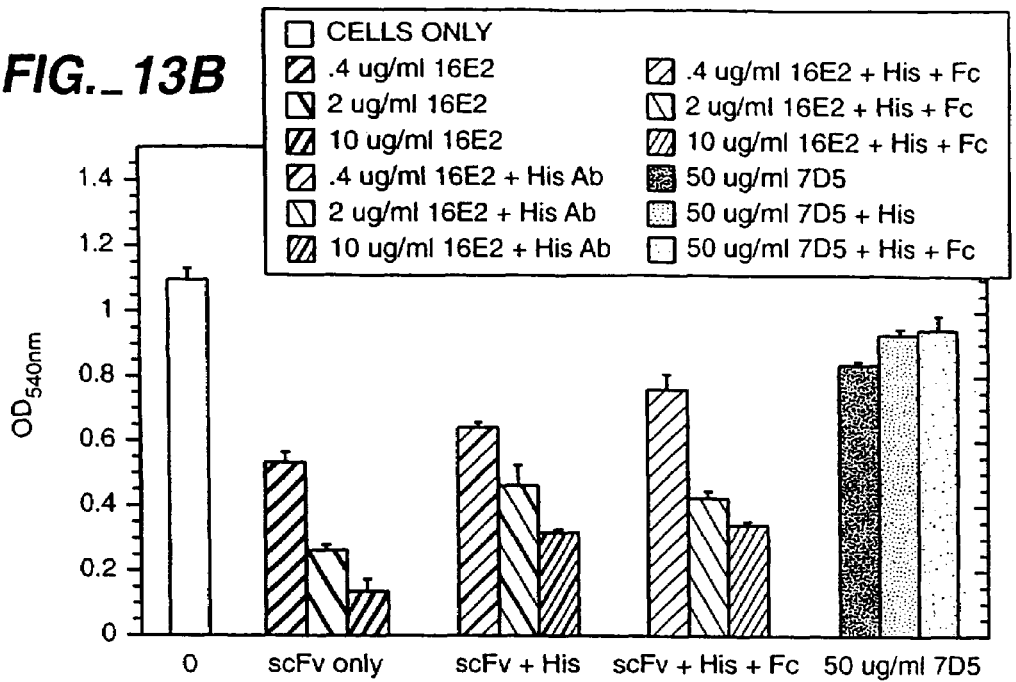
FIG._13B
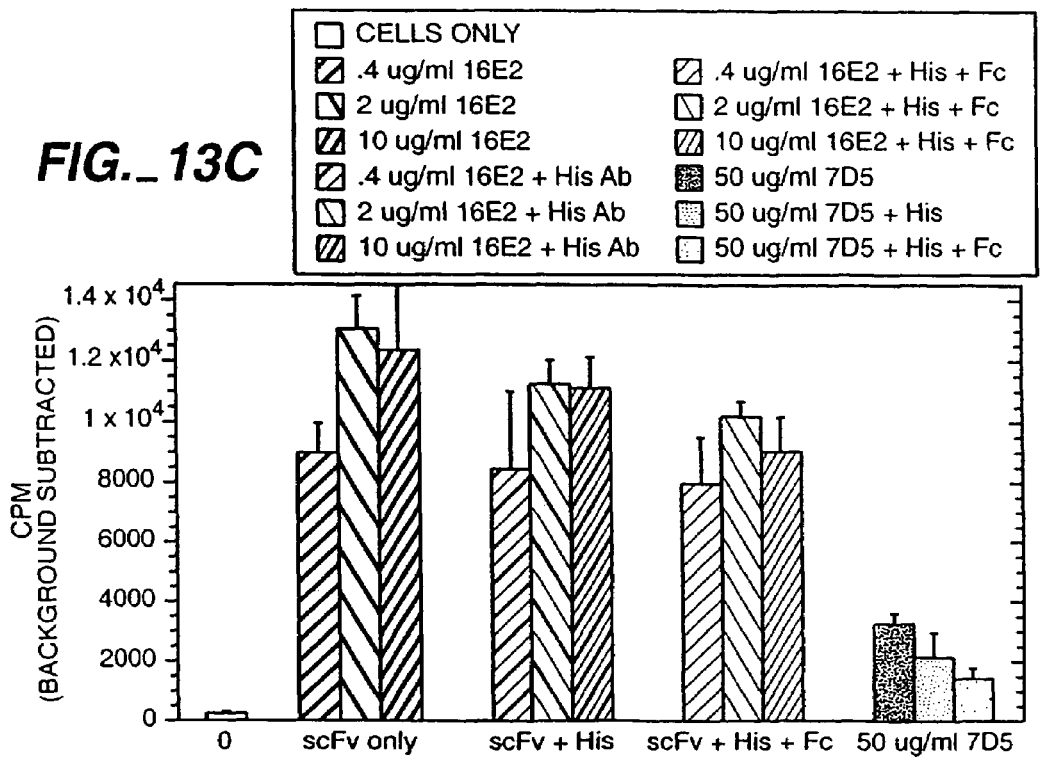
FIG._13C

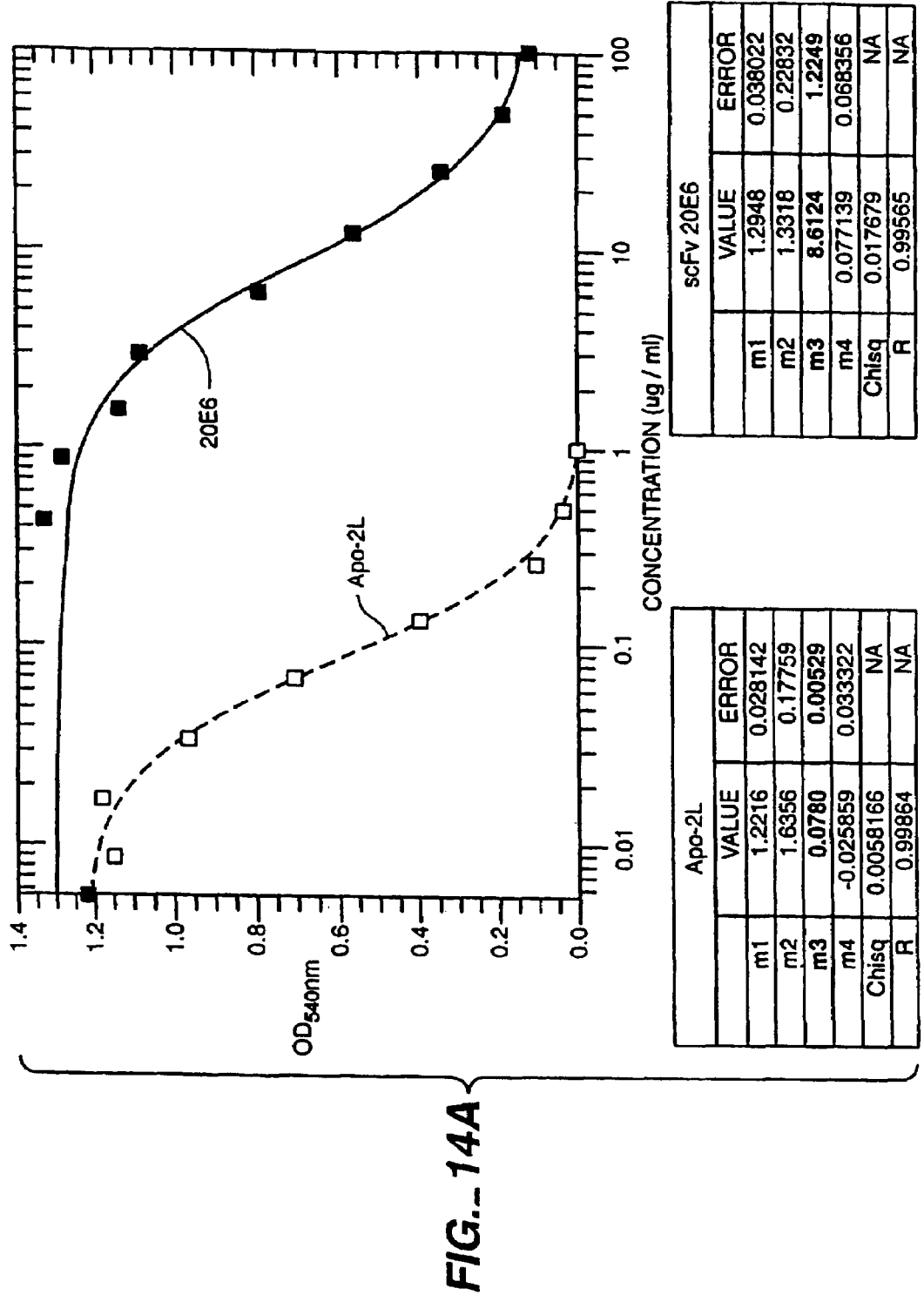
FIG._14A

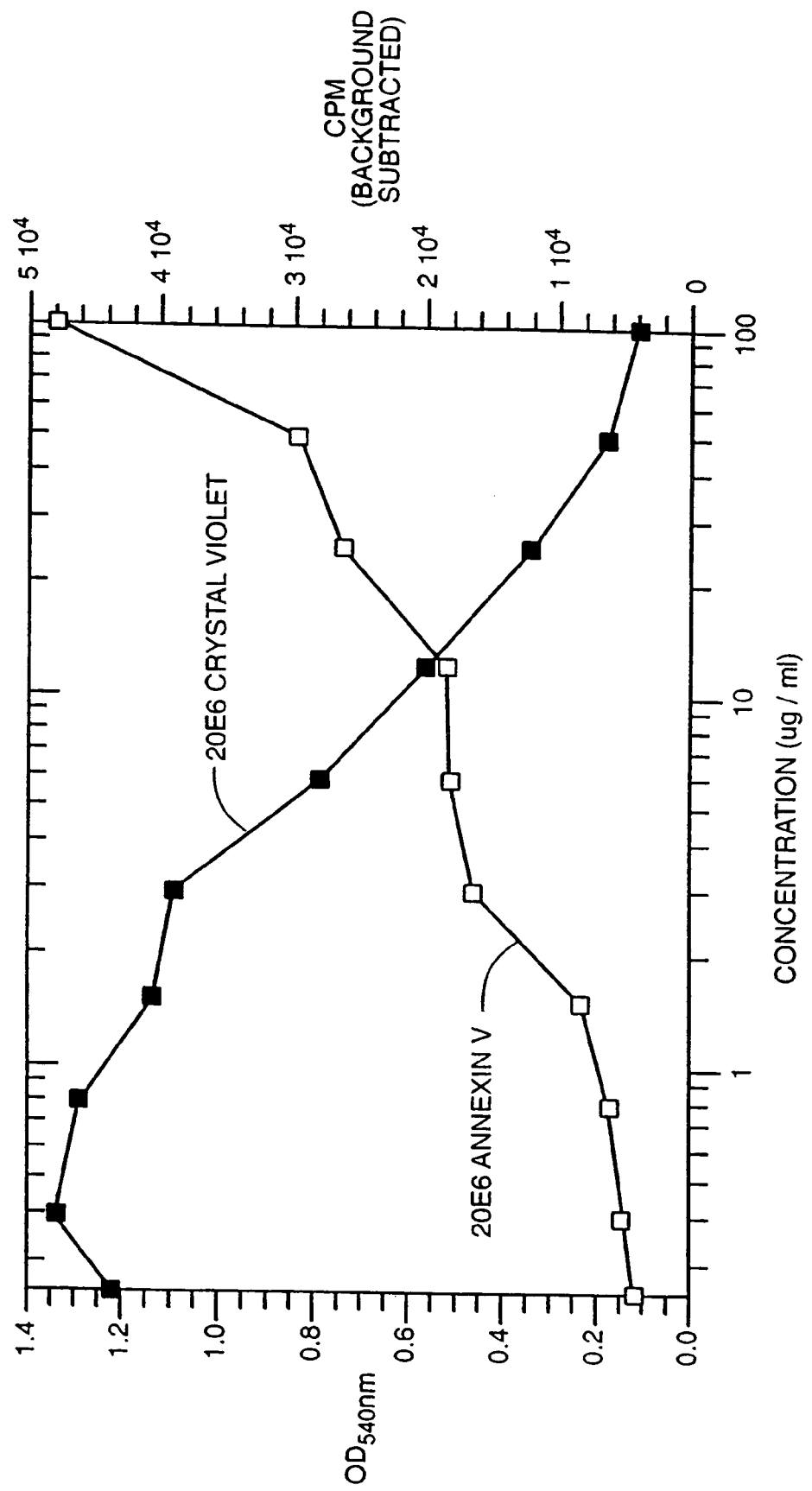
FIG._14B

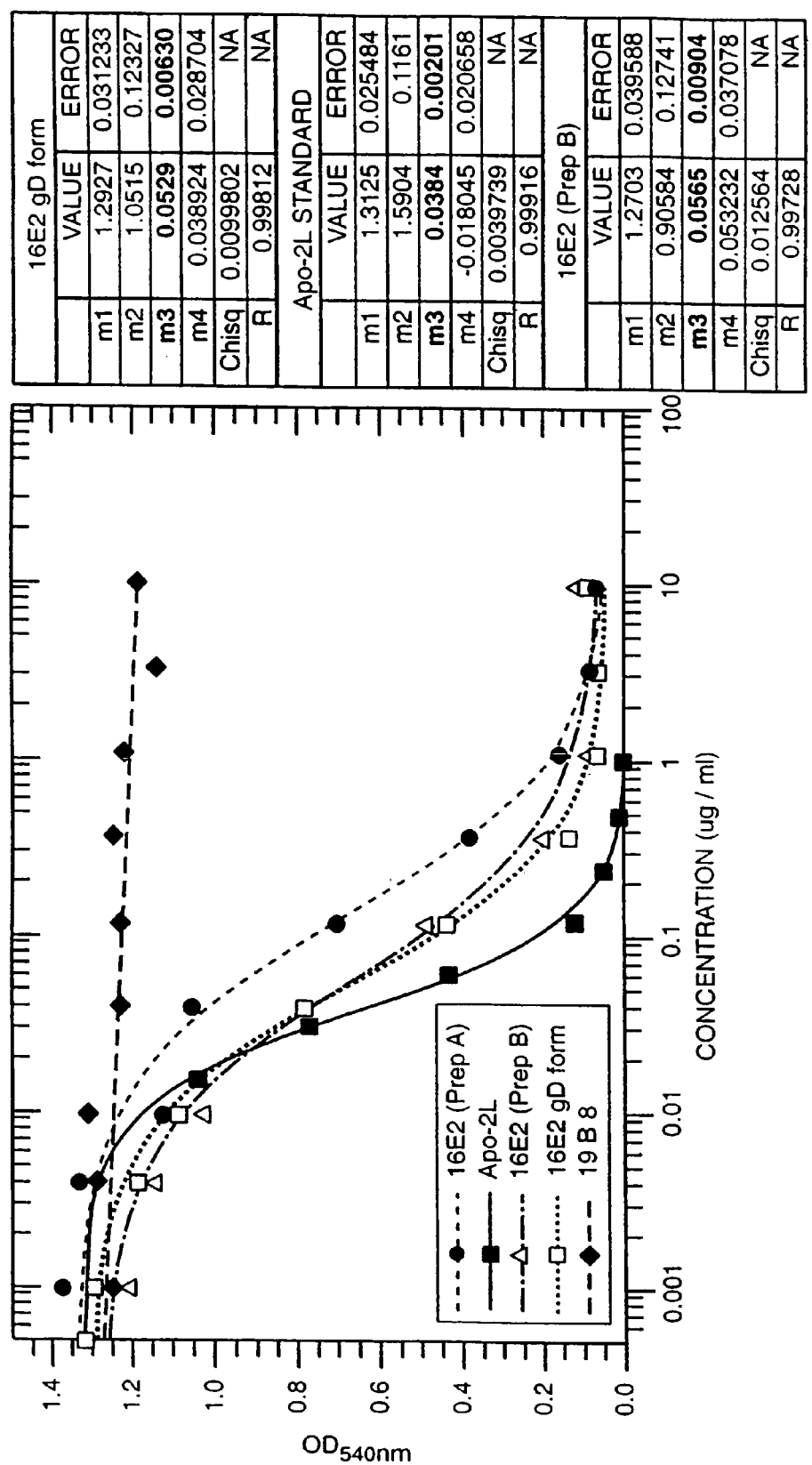
FIG._14C

ATGACCATGA TTACGCCAAG CTTTGGAGCC TTTTTTTTGG AGATTTTCAA 50
CGTGAAAAAA TTATTATTCG CAATTCCTTT AGTTGTTCCT TTCTATGCGG 100
CCCAGCCGGC CATGGCCGAG GTGCAGCTGG TGCAGTCTGG GGGAGGTGTG 150
GAACGGCCGG GGGGGTCCCT GAGACTCTCC TGTGCAGCCT CTGGATTCAC 200
CTTTGATGAT TATGGCATGA GCTGGGTCCG CCAAGCTCCA GGGAAGGGGC 250
TGGAGTGGGT CTCTGGTATT AATTGGAATG GTGGTAGCAC AGGATATGCA 300
GACTCTGTGA AGGGCCGAGT CACCATCTCC AGAGACAACG CCAAGAACTC 350
CCTGTATCTG CAAATGAACA GCCTGAGAGC CGAGGACACG GCCGTATATT 400
ACTGTGCGAA AATCCTGGGT GCCGGACGGG GCTGGTACTT CGATCTCTGG 450
GGGAAGGGGA CCACGGTCAC CGTCTCGAGT GGTGGAGGCG GTTCAGGCGG 500
AGGTGGCAGC GGCGGTGGCG GATCGTCTGA GCTGACTCAG GACCCTGCTG 550
TGTCTGTGGC CTTGGACAGA CAGTCAGGA TCACATGCCA AGGAGACAGC 600
CTCAGAAGCT ATTATGCAAG CTGGTACCAG CAGAAGCCAG GACAGGCCCC 650
TGTACTTGTC ATCTATGGTA AAACAACCG GCCCTCAGGG ATCCCAGACC 700
GATTCTCTGG CTCCAGCTCA GGAAACACAG CTTCCTTGAC CATCACTGGG 750
GCTCAGGCGG AAGATGAGGC TGACTATTAC TGTAACTCCC GGGACAGCAG 800
TGGTAACCAT GTGGTATTCG GCGGAGGGAC CAAGCTGACC GTCCTAGGTG 850
CGGCCGCACA TCATCATCAC CATCACGGGG CCGCAGAACA AAAACTCATC 900
TCAGAAGAGG ATCTGAATGG GGCCGCATAG 930

FIG._15A

ATGACCATGA TTACGCCAAG CTTTGGAGCC TTTTTTTTGG AGATTTTCAA 50
CGTGAAAAAA TTATTATTCG CAATTCCTTT AGTTGTTCCT TTCTATGCGG 100
CCCAGCCGGC CATGGCCGGG GTGCAGCTGG TGGAGTCTGG GGGAGGCTTG 150
GTCCAGCCTG GGGGGTCCCT GAGACTCTCC TGTGCAGCCT CTGGATTCAC 200
CTTTAGTAGC TATTGGATGA GCTGGGTCCG CCAGGCTCCA GGGAAGGGGC 250
TGGAGTGGGT GGCCAACATA AAGCAAGATG GAAGTGAGAA ATACTATGTG 300
GACTCTGTGA AGGGCCGATT CACCATCTCC AGAGACAACG CCAAGAACTC 350
ACTGTATCTG CAAATGAACA GCCTGAGAGC CGAGGACACG GCTGTGTATT 400
ACTGTGCGAG AGATCTTTTA AAGGTCAAGG CAGCTCGTC TGGGTGGTTC 450
GACCCCTGGG GGAGAGGGAC CACGGTCACC GTCTCGAGT GTGGAGGCGG 500
TTCAGGCGGA GGTGGTAGCG GCGGTGGCGG ATCGTCTGAG CTGACTCAGG 550
ACCCTGCTGT GTCTGTGGCC TTGGACAGA CAGTCAGGAT CACATGCCAA 600
GGAGACAGCC TCAGAAGCTA TTATGCAAGC TGGTACCAGC AGAAGCCAGG 650
ACAGGCCCCT GTACTTGTCA TCTATGGTAA AACAACCGG CCCTCAGGGA 700
TCCCAGACCG ATTCTCTGGC TCCAGCTCAG GAAACACAGC TTCCTTGACC 750
ATCACTGGGG CTCAGGCGGA AGATGAGGCT GACTATTACT GTAACTCCCG 800
GGACAGCAGT GGTAACCATG TGGTATTCGG CGGAGGGACC AAGCTGACCG 850
TCCTAGGTGC GGCCGCACAT CATCATCACC ATCACGGGGC CGCAGAACAA 900
AAACTCATCT CAGAAGAGGA TCTGAATGGG GCCGCATAG 939

FIG._15B

```
ATGACCATGA TTACGCCAAG CTTTGGAGCC TTTTTTTTGG AGATTTTCAA 50
CGTGAAAAAA TTATTATTCG CAATTCCTTT AGTTGTTCCT TTCTATGCGG 100
CCCAGCCGGC CATGGCCCAG GTGCAGCTGG TGCAGTCTGG GGGAGGCGTG 150
GTCCAGCCTG GCGGTCCCT GAGACTCTCC TGTGCAGCTT CTGGGTTCAT 200
TTTCAGTAGT TATGGGATGC ACTGGGTCCG CCAGGCTCCA GGCAAGGGGC 250
TGGAGTGGGT GGCAGGTATT TTTTATGATG GAGGTAATAA ATACTATGCA 300
GACTCCGTGA AGGGCCGATT CACCATCTCC AGAGACAATT CCAAGAACAC 350
GCTGTATCTG CAAATGAACA GCCTGAGAGC TGAGGACACG GCTGTGTATT 400
ACTGTGCGAG AGATAGGGGC TACTACTACA TGGACGTCTG GGGCAAAGGG 450
ACCACGGTCA CCGTCTCCTC AGGTGGAGGC GGTTCAGGCG GAGGTGGCTC 500
TGGCGGTGGC GGATCGCAGT CTGTGTTGAC GCAGCCGCCC TCAGTGTCTG 550
GGCCCCAGG ACAGAGGGTC ACCATCTCCT GCACTGGGAG AAGCTCCAAC 600
ATCGGGCAG GTCATGATGT ACACTGGTAC CAGCAACTTC CAGGAACAGC 650
CCCCAAACTC CTCATCTATG ATGACAGCAA TCGGCCCTCA GGGGTCCCTG 700
ACCGATTCTC TGGCTCCAGG TCTGGCACCT CAGCCTCCCT GGCCATCACT 750
GGGCTCCAGG CTGAAGATGA GGCTGATTAT TACTGCCAGT CCTATGACAG 800
CAGCCTGAGG GGTTCGGTAT TCGGCGGAGG GACCAAGGTC ACTGTCCTAG 850
GTGCGGCCGC ACATCATCAT CACCATCACG GGGCCGCAGA ACAAAAACTC 900
ATCTCAGAAG AGGATCTGAA TGGGGCCGCA TAG 933
```

FIG._15C

```
                    signal                                                          Heavy chain
Apo-2.16E2.his    1 MTMITPSFGAFFLEIFNVKLLFAIPLVVPFYAAQPAMAEVQLVQSGGGV
Apo-2.20E6.his    1 MTMITPSFGAFFLEIFNVKLLFAIPLVVPFYAAQPAMAGVQLVESGGGL
Apo-2.24C4.his    1 MTMITPSFGAFFLEIFNVKLLFAIPLVVPFYAAQPAMAQVQLVQSGGGV CDR1                          CDR2
Apo-2.16E2.his   51 ERPGGSLRLSCAASGFTFDDYGMSWVRQAPGKGLEWVSGINWNGGSTGYA
Apo-2.20E6.his   51 VQPGGSLRLSCAASGFTFSSYWMSWVRQAPGKGLEWVANIKQDGSEKYYV
Apo-2.24C4.his   51 VQPGRSLRLSCAASGFIFSSYGMHWVRQAPGKGLEWVAGIFYDGGNKYYA CDR3
Apo-2.16E2.his  101 DSVKGRVTISRDNAKNSLYLQMNSLRAEDTAVYYCAKIL----GAGRGWY
Apo-2.20E6.his  101 DSVKGRFTISRDNAKNSLYLQMNSLRAEDTAVYYCARDLLRVKGSSSGW-
Apo-2.24C4.his  101 DSVKGRFTISRDNSKNTLYLQMNSLRAEDTAVYYCARD------RGYY Light chain
Apo-2.16E2.his  147 F-DLWGKGTTVTVSSGGGGSGGGGSGGGGS-SELTQDPAVSVALGQTVRI
Apo-2.20E6.his  150 F-DPWGRGTTVTVSSGGGGSGGGGSGGGGS-SELTQDPAVSVALGQTVRI
Apo-2.24C4.his  143 YMDVWGKGTTVTVSSGGGGSGGGGSGGGGSGGGGSQSVLTQPPSVSGAPGQRVTI CDR1                       CDR2
Apo-2.16E2.his  195 TCQGDSLR---SYYASWYQQKPGQAPVLVIYGKNNRPSGIPDRFSGSSSG
Apo-2.20E6.his  198 TCQGDSLR---SYYASWYQQKPGQAPVLVIYGKNNRPSGIPDRFSGSSSG
Apo-2.24C4.his  193 SCTGRSSNIGAGHDVHWYQQLPGTAPKLLIYDDSNRPSGVPDRFSGSRSG CDR3
Apo-2.16E2.his  242 NTASLTITGAQAEDEADYYCNSRDSSGNHVVFGGGTKLTVLGAAAHHHHHH
Apo-2.20E6.his  245 NTASLTITGAQAEDEADYYCNSRDSSGNHVVFGGGTKLTVLGAAAHHHHHH
Apo-2.24C4.his  243 TSASLAITGLQAEDEADYYCQSYDSSLRGSVFGGGTKVTVLGAAAHHHHHH Apo-2.16E2.his  292 HGAAEQKLISEEDLNGAA
Apo-2.20E6.his  295 HGAAEQKLISEEDLNGAA
Apo-2.24C4.his  293 HGAAEQKLISEEDLNGAA
```

FIG._16

APO-2 RECEPTOR POLYPEPTIDES

RELATED APPLICATIONS

This application is a divisional application of U.S. Ser. No. 10/423,448 filed Apr. 25, 2003, currently pending, which is a continuation of U.S. Ser. No. 10/288,917 filed Nov. 6, 2002, now abandoned, which is a continuation of U.S. Ser. No. 10/052,798 filed Nov. 2, 2001, now issued as U.S. Pat. No. 7,314,619, which is a divisional of application of U.S. Ser. No. 09/079,029 filed May 14, 1998, now issued as U.S. Pat. No. 6,342,369, claiming priority under Section 119(e) to provisional application No. 60/046,615 filed May 15, 1997, now lapsed, and provisional application No. 60/074,119 filed Feb. 9, 1998, now lapsed, the contents of all of which are hereby incorporated by reference.

FIELD OF THE INVENTION

The present invention relates generally to the identification, isolation, and recombinant production of novel polypeptides, designated herein as Apo-2, and to anti-Apo-2 antibodies.

BACKGROUND OF THE INVENTION

Apoptosis or "Programmed Cell Death"

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" [see, e.g., Barr et al., *Bio/Technology*, 12:487-493 (1994); Steller et al., *Science*, 267:1445-1449 (1995)]. Apoptotic cell death naturally occurs in many physiological processes, including embryonic development and clonal selection in the immune system [Itoh et al., *Cell*, 66:233-243 (1991)]. Decreased levels of apoptotic cell death have been associated with a variety of pathological conditions, including cancer, lupus, and herpes virus infection [Thompson, *Science*, 267:1456-1462 (1995)]. Increased levels of apoptotic cell death may be associated with a variety of other pathological conditions, including AIDS, Alzheimer's disease, Parkinson's disease, amyotrophic lateral sclerosis, multiple sclerosis, retinitis pigmentosa, cerebellar degeneration, aplastic anemia, myocardial infarction, stroke, reperfusion injury, and toxin-induced liver disease [see, Thompson, supra].

Apoptotic cell death is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A variety of extrinsic and intrinsic signals are believed to trigger or induce such morphological and biochemical cellular changes [Raff, *Nature*, 356:397-400 (1992); Steller, supra; Sachs et al., *Blood*, 82:15 (1993)]. For instance, they can be triggered by hormonal stimuli, such as glucocorticoid hormones for immature thymocytes, as well as withdrawal of certain growth factors [Watanabe-Fukunaga et al., *Nature*, 356:314-317 (1992)]. Also, some identified oncogenes such as myc, rel, and E1A, and tumor suppressors, like p53, have been reported to have a role in inducing apoptosis. Certain chemotherapy drugs and some forms of radiation have likewise been observed to have apoptosis-inducing activity [Thompson, supra].

TNF Family of Cytokines

Various molecules, such as tumor necrosis factor-α ("TNF-α"), tumor necrosis factor-β ("TNF-β" or "lymphotoxin"), CD30 ligand, CD27 ligand, CD40 ligand, OX-40 ligand, 4-1BB ligand, Apo-1 ligand (also referred to as Fas ligand or CD95 ligand), and Apo-2 ligand (also referred to as TRAIL) have been identified as members of the tumor necrosis factor ("TNF") family of cytokines [See, e.g., Gruss and Dower, *Blood*, 85:3378-3404 (1995); Wiley et al., *Immunity*, 3:673-682 (1995); Pitti et al., *J. Biol. Chem.*, 271:12687-12690 (1996); WO 97/01633 published Jan. 16, 1997]. Among these molecules, TNF-α, TNF-β, CD30 ligand, 4-1BB ligand, Apo-1 ligand, and Apo-2 ligand (TRAIL) have been reported to be involved in apoptotic cell death. Both TNF-α and TNF-β have been reported to induce apoptotic death in susceptible tumor cells [Schmid et al., *Proc. Natl. Acad. Sci.*, 83:1881 (1986); Dealtry et al., *Eur. J. Immunol.*, 17:689 (1987)]. Zheng et al. have reported that TNF-α is involved in post-stimulation apoptosis of CD8-positive T cells [Zheng et al., *Nature*, 377:348-351 (1995)]. Other investigators have reported that CD30 ligand may be involved in deletion of self-reactive T cells in the thymus [Amakawa et al., Cold Spring Harbor Laboratory Symposium on Programmed Cell Death, Abstr. No. 10, (1995)].

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery [Krammer et al., *Curr. Op. Immunol.*, 6:279-289 (1994); Nagata et al., *Science*, 267:1449-1456 (1995)]. Apo-1 ligand is also reported to induce post-stimulation apoptosis in CD4-positive T lymphocytes and in B lymphocytes, and may be involved in the elimination of activated lymphocytes when their function is no longer needed [Krammer et al., supra; Nagata et al., supra]. Agonist mouse monoclonal antibodies specifically binding to the Apo-1 receptor have been reported to exhibit cell killing activity that is comparable to or similar to that of TNF-α [Yonehara et al., *J. Exp. Med.*, 169:1747-1756 (1989)].

TNF Family of Receptors

Induction of various cellular responses mediated by such TNF family cytokines is believed to be initiated by their binding to specific cell receptors. Two distinct TNF receptors of approximately 55-kDa (TNFR1) and 75-kDa (TNFR2) have been identified [Hohman et al., *J. Biol. Chem.*, 264:14927-14934 (1989); Brockhaus et al., *Proc. Natl. Acad. Sci.*, 87:3127-3131 (1990); EP 417,563, published Mar. 20, 1991] and human and mouse cDNAs corresponding to both receptor types have been isolated and characterized [Loetscher et al., *Cell*, 61:351 (1990); Schall et al., *Cell*, 61:361 (1990); Smith et al., *Science*, 248:1019-1023 (1990); Lewis et al., *Proc. Natl. Acad. Sci.*, 88:2830-2834 (1991); Goodwin et al., *Mol. Cell. Biol.*, 11:3020-3026 (1991)]. Extensive polymorphisms have been associated with both TNF receptor genes [see, e.g., Takao et al., *Immunogenetics*, 37:199-203 (1993)]. Both TNFRs share the typical structure of cell surface receptors including extracellular, transmembrane and intracellular regions. The extracellular portions of both receptors are found naturally also as soluble TNF-binding proteins [Nophar, Y. et al., *EMBO J.*, 9:3269 (1990); and Kohno, T. et al., *Proc. Natl. Acad. Sci. U.S.A.*, 87:8331 (1990)]. The cloning of recombinant soluble TNF receptors was reported by Hale et al. [*J. Cell. Biochem. Supplement* 15F, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the $NH_2$-terminus. Each CRD is about 40 amino acids long and contains 4 to 6 cysteine residues at positions which are well conserved [Schall et al., supra; Loetscher et al., supra; Smith et al., supra; Nophar et al., supra; Kohno et al., supra]. In TNFR1, the approximate boundaries of the four CRDs are as follows: CRD1-amino acids 14 to about 53; CRD2-amino acids from about 54 to about 97; CRD3-amino acids from about 98 to about 138; CRD4-amino acids from about 139 to about 167. In TNFR2, CRD1 includes amino acids 17 to about 54; CRD2-amino acids from about 55 to about 97; CRD3-amino acids from about 98 to about 140; and CRD4-amino acids from about 141 to about 179 [Banner et al., Cell, 73:431-435 (1993)]. The potential role of the CRDs in ligand binding is also described by Banner et al., supra.

A similar repetitive pattern of CRDs exists in several other cell-surface proteins, including the p75 nerve growth factor receptor (NGFR) [Johnson et al., Cell, 47:545 (1986); Radeke et al., Nature, 325:593 (1987)], the B cell antigen CD40 [Stamenkovic et al., EMBO J., 8:1403 (1989)], the T cell antigen OX40 [Mallet et al., EMBO J., 9:1063 (1990)] and the Fas antigen [Yonehara et al., supra and Itoh et al., supra]. CRDs are also found in the soluble TNFR (sTNFR)-like T2 proteins of the Shope and myxoma poxviruses [Upton et al., Virology, 160:20-29 (1987); Smith et al., Biochem. Biophys. Res. Commun., 176:335 (1991); Upton et al., Virology, 184:370 (1991)]. Optimal alignment of these sequences indicates that the positions of the cysteine residues are well conserved. These receptors are sometimes collectively referred to as members of the TNF/NGF receptor superfamily. Recent studies on p75NGFR showed that the deletion of CRD1 [Welcher, A. A. et al., Proc. Natl. Acad. Sci. USA, 88:159-163 (1991)] or a 5-amino acid insertion in this domain [Yan, H. and Chao, M. V., J. Biol. Chem., 266:12099-12104 (1991)] had little or no effect on NGF binding [Yan, H. and Chao, M. V., supra]. p75 NGFR contains a proline-rich stretch of about 60 amino acids, between its CRD4 and transmembrane region, which is not involved in NGF binding [Peetre, C. et al., Eur. J. Hematol., 41:414-419 (1988); Seckinger, P. et al., J. Biol. Chem., 264:11966-11973 (1989); Yan, H. and Chao, M. V., supra]. A similar proline-rich region is found in TNFR2 but not in TNFR1.

Itoh et al. disclose that the Apo-1 receptor can signal an apoptotic cell death similar to that signaled by the 55-kDa TNFR1 [Itoh et al., supra]. Expression of the Apo-1 antigen has also been reported to be down-regulated along with that of TNFR1 when cells are treated with either TNF-α or anti-Apo-1 mouse monoclonal antibody [Krammer et al., supra; Nagata et al., supra]. Accordingly, some investigators have hypothesized that cell lines that co-express both Apo-1 and TNFR1 receptors may mediate cell killing through common signaling pathways [Id.].

The TNF family ligands identified to date, with the exception of lymphotoxin-α, are type II transmembrane proteins, whose C-terminus is extracellular. In contrast, the receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-α, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Recently, other members of the mammalian TNFR family have been identified. In Marsters et al., Curr. Biol., 6:750 (1996), investigators describe a full length native sequence human polypeptide, called Apo-3, which exhibits similarity to the TNFR family in its extracellular cysteine-rich repeats and resembles TNFR1 and CD95 in that it contains a cytoplasmic death domain sequence [see also Marsters et al., Curr. Biol., 6:1669 (1996)]. Apo-3 has also been referred to by other investigators as DR3, wsl-1 and TRAMP [Chinnaiyan et al., Science, 274:990 (1996); Kitson et al., Nature, 384:372 (1996); Bodmer et al., Immunity, 6:79 (1997)].

Pan et al. have disclosed another TNF receptor family member referred to as "DR4" [Pan et al., Science, 276:111-113 (1997)]. The DR4 was reported to contain a cytoplasmic death domain capable of engaging the cell suicide apparatus. Pan et al. disclose that DR4 is believed to be a receptor for the ligand known as Apo-2 ligand or TRAIL.

The Apoptosis-Inducing Signaling Complex

As presently understood, the cell death program contains at least three important elements—activators, inhibitors, and effectors; in C. elegans, these elements are encoded respectively by three genes, Ced-4, Ced-9 and Ced-3 [Steller, Science, 267:1445 (1995); Chinnaiyan et al., Science, 275:1122-1126 (1997)]. Two of the TNFR family members, TNFR1 and Fas/Apo1 (CD95), can activate apoptotic cell death [Chinnaiyan and Dixit, Current Biology, 6:555-562 (1996); Fraser and Evan, Cell; 85:781-784 (1996)]. TNFR1 is also known to mediate activation of the transcription factor, NF-κB [Tartaglia et al., Cell, 74:845-853 (1993); Hsu et al., Cell, 84:299-308 (1996)]. In addition to some ECD homology, these two receptors share homology in their intracellular domain (ICD) in an oligomerization interface known as the death domain [Tartaglia et al., supra; Nagata, Cell, 88:355 (1997)]. Death domains are also found in several metazoan proteins that regulate apoptosis, namely, the Drosophila protein, Reaper, and the mammalian proteins referred to as FADD/MORT1, TRADD, and RIP [Cleaveland and Ihle, Cell, 81:479-482 (1995)]. Using the yeast-two hybrid system, Raven et al. report the identification of protein, wsl-1, which binds to the TNFR1 death domain [Raven et al., Programmed Cell Death Meeting, Sep. 20-24, 1995, Abstract at page 127; Raven et al., European Cytokine Network, 7:Abstr. 82 at page 210 (April-June 1996)]. The wsl-1 protein is described as being homologous to TNFR1 (48% identity) and having a restricted tissue distribution. According to Raven et al., the tissue distribution of wsl-1 is significantly different from the TNFR1 binding protein, TRADD.

Upon ligand binding and receptor clustering, TNFR1 and CD95 are believed to recruit FADD into a death-inducing signalling complex. CD95 purportedly binds FADD directly, while TNFR1 binds FADD indirectly via TRADD [Chinnaiyan et al., Cell, 81:505-512 (1995); Boldin et al., J. Biol. Chem., 270:387-391 (1995); Hsu et al., supra; Chinnaiyan et al., J. Biol. Chem., 271:4961-4965 (1996)]. It has been reported that FADD serves as an adaptor protein which recruits the Ced-3-related protease, MACHα/FLICE (caspase 8), into the death signalling complex [Boldin et al., Cell, 85:803-815 (1996); Muzio et al., Cell, 85:817-827 (1996)]. MACHα/FLICE appears to be the trigger that sets off a cascade of apoptotic proteases, including the interleukin-1β converting enzyme (ICE) and CPP32/Yama, which may execute some critical aspects of the cell death programme [Fraser and Evan, supra].

It was recently disclosed that programmed cell death involves the activity of members of a family of cysteine proteases related to the C. elegans cell death gene, ced-3, and to the mammalian IL-1-converting enzyme, ICE. The activity of the ICE and CPP32/Yama proteases can be inhibited by the product of the cowpox virus gene, crmA [Ray et al., *Cell*, 69:597-604 (1992); Tewari et al., *Cell*, 81:801-809 (1995)]. Recent studies show that CrmA can inhibit TNFR1- and CD95-induced cell death [Enari et al., *Nature*, 375:78-81 (1995); Tewari et al., *J. Biol. Chem.*, 270:3255-3260 (1995)].

As reviewed recently by Tewari et al., TNFR1, TNFR2 and CD40 modulate the expression of proinflammatory and costimulatory cytokines, cytokine receptors, and cell adhesion molecules through activation of the transcription factor, NF-κB [Tewari et al., *Curr. Op. Genet. Develop.*, 6:39-44 (1996)]. NF-κB is the prototype of a family of dimeric transcription factors whose subunits contain conserved Rel regions [Verma et al., *Genes Develop.*, 9:2723-2735 (1996); Baldwin, *Ann. Rev. Immunol.*, 14:649-681 (1996)]. In its latent form, NF-κB is complexed with members of the IκB inhibitor family; upon inactivation of the IκB in response to certain stimuli, released NF-κB translocates to the nucleus where it binds to specific DNA sequences and activates gene transcription.

For a review of the TNF family of cytokines and their receptors, see Gruss and Dower, supra.

SUMMARY OF THE INVENTION

Applicants have identified cDNA clones that encode novel polypeptides, designated in the present application as "Apo-2." It is believed that Apo-2 is a member of the TNFR family; full-length native sequence human Apo-2 polypeptide exhibits some similarities to some known TNFRs, including a cytoplasmic death domain region. Full-length native sequence human Apo-2 also exhibits similarity to the TNFR family in its extracellular cysteine-rich repeats. Apo-2 polypeptide has been found to be capable of triggering caspase-dependent apoptosis and activating NF-κB. Applicants surprisingly found that a soluble extracellular domain of Apo-2 binds Apo-2 ligand ("Apo-2L") and can inhibit Apo-2 ligand function. It is presently believed that Apo-2 ligand can signal via at least two different receptors, DR4 and the newly described Apo-2 herein.

In one embodiment, the invention provides isolated Apo-2 polypeptide. In particular, the invention provides isolated native sequence Apo-2 polypeptide, which in one embodiment, includes an amino acid sequence comprising residues 1 to 411 of FIG. 1 (SEQ ID NO:1). In other embodiments, the isolated Apo-2 polypeptide comprises at least about 80% amino acid sequence identity with native sequence Apo-2 polypeptide comprising residues 1 to 411 of FIG. 1 (SEQ ID NO:1). Optionally, the Apo-2 polypeptide is obtained or obtainable by expressing the polypeptide encoded by the cDNA insert of the vector deposited as ATCC 209021.

In another embodiment, the invention provides an isolated extracellular domain (ECD) sequence of Apo-2. Optionally, the isolated extracellular domain sequence comprises amino acid residues 54 to 182 of FIG. 1 (SEQ ID NO:1).

In another embodiment, the invention provides an isolated death domain sequence of Apo-2. Optionally, the isolated death domain sequence comprises amino acid residues 324 to 391 of FIG. 1 (SEQ ID NO:1).

In another embodiment, the invention provides chimeric molecules comprising Apo-2 polypeptide fused to a heterologous polypeptide or amino acid sequence. An example of such a chimeric molecule comprises an Apo-2 fused to an immunoglobulin sequence. Another example comprises an extracellular domain sequence of Apo-2 fused to a heterologous polypeptide or amino acid sequence, such as an immunoglobulin sequence.

In another embodiment, the invention provides an isolated nucleic acid molecule encoding Apo-2 polypeptide. In one aspect, the nucleic acid molecule is RNA or DNA that encodes an Apo-2 polypeptide or a particular domain of Apo-2, or is complementary to such encoding nucleic acid sequence, and remains stably bound to it under at least moderate, and optionally, under high stringency conditions. Such complementary nucleic acid may be fully complementary to the entire length of the RNA or DNA. It is contemplated that the complementary nucleic acid may also be complementary to only a fragment of the RNA or DNA nucleotide sequence. In one embodiment, the nucleic acid sequence is selected from:

(a) the coding region of the nucleic acid sequence of FIG. 1 (SEQ ID NO:2) that codes for residue 1 to residue 411 (i.e., nucleotides 140-142 through 1370-1372), inclusive;

(b) the coding region of the nucleic acid sequence of FIG. 1 (SEQ ID NO:2) that codes for residue 1 to residue 182 (i.e., nucleotides 140-142 through 683-685), inclusive;

(c) the coding region of the nucleic acid sequence of FIG. 1 (SEQ ID NO:2) that codes for residue 54 to residue 182 (i.e., nucleotides 299-301 through 683-685), inclusive;

(d) the coding region of the nucleic acid sequence of FIG. 1 (SEQ ID NO:2) that codes for residue 324 to residue 391 (i.e., nucleotides 1109-1111 through 1310-1312), inclusive; or (e) a sequence corresponding to the sequence of (a), (b), (c) or (d) within the scope of degeneracy of the genetic code. The isolated nucleic acid may comprise the Apo-2 polypeptide cDNA insert of the vector deposited as ATCC 209021 which includes the nucleotide sequence encoding Apo-2 polypeptide.

In a further embodiment, the invention provides a vector comprising the nucleic acid molecule encoding the Apo-2 polypeptide or particular domain of Apo-2. A host cell comprising the vector or the nucleic acid molecule is also provided. A method of producing Apo-2 is further provided.

In another embodiment, the invention provides an antibody which specifically binds to Apo-2. The antibody may be an agonistic, antagonistic or neutralizing antibody. Single-chain antibodies and dimeric molecules, in particular homodimeric molecules, comprising Apo-2 antibody are also provided.

In another embodiment, the invention provides non-human, transgenic or knock-out animals.

A further embodiment of the invention provides articles of manufacture and kits that include Apo-2 or Apo-2 antibodies.

BRIEF DESCRIPTION OF THE DRAWINGS

FIGS. 1A-1C show the nucleotide sequence of a native sequence human Apo-2 cDNA (SEQ ID NO:2) and its derived amino acid sequence (SEQ ID NO:1).

FIG. 2A shows the derived amino acid sequence of a native sequence human Apo-2 (SEQ ID NO:1)—the putative signal sequence is underlined, the putative transmembrane domain is boxed, and the putative death domain sequence is dash underlined. The cysteines of the two cysteine-rich domains are individually underlined.

FIG. 2B shows an alignment and comparison of the death domain sequences of native sequence human Apo-2 (SEQ ID NO:15), DR4 (SEQ ID NO:16), Apo-3/DR3 (SEQ ID NO:17), TNFR1 (SEQ ID NO:18), and Fas/Apo-1 (CD95) (SEQ ID NO:19). Asterisks indicate residues that are essential for death signaling by TNFR1.

FIG. 3 shows the interaction of the Apo-2 ECD with Apo-2L. Supernatants from mock-transfected 293 cells or from 293 cells transfected with Flag epitope-tagged Apo-2 ECD were incubated with poly-His-tagged Apo-2L and subjected to immunoprecipitation with anti-Flag conjugated or Nickel conjugated agarose beads. The precipitated proteins were resolved by electrophoresis on polyacrylamide gels, and detected by immunoblot with anti-Apo-2L or anti-Flag antibody.

FIG. 4 shows the induction of apoptosis by Apo-2 and inhibition of Apo-2L activity by soluble Apo-2 ECD. Human 293 cells (A, B) or HeLa cells (C) were transfected by pRK5 vector or by pRK5-based plasmids encoding Apo-2 and/or CrmA. Apoptosis was assessed by morphology (A), DNA fragmentation (B), or by FACS (C-E). Soluble Apo-2L was pre-incubated with buffer or affinity-purified Apo-2 ECD together with anti-Flag antibody or Apo-2 ECD immunoadhesin or DR4 or TNFR1 immunoadhesins and added to HeLa cells. The cells were later analyzed for apoptosis (D). Dose-response analysis using Apo-2L with Apo-2 ECD immunoadhesin was also determined (E).

FIG. 5 shows activation of NF-κB by Apo-2, DR4, and Apo-2L. (A) HeLa cells were transfected with expression plasmids encoding the indicated proteins. Nuclear extracts were prepared and analyzed by an electrophoretic mobility shift assay. (B) HeLa cells or MCF7 cells were treated with buffer, Apo-2L or TNF-alpha and assayed for NF-κB activity. (C) HeLa cells were preincubated with buffer, ALLN or cyclohexamide before addition of Apo-2L. Apoptosis was later analyzed by FACS.

FIG. 6A shows expression of Apo-2 mRNA in human tissues as analyzed by Northern hybridization of human tissue poly A RNA blots.

FIG. 6B shows expression of Apo-2 mRNA in human cancer cell lines as analyzed by Northern hybridization of human cancer cell line poly A RNA blots.

FIG. 7 shows the FACS analysis of an Apo-2 antibody, 3F11.39.7 (illustrated by the bold lines) as compared to IgG controls (dotted lines). The 3F11.39.7 antibody recognized the Apo-2 receptor expressed in human 9D cells.

FIG. 8 is a graph showing percent (%) apoptosis induced in 9D cells by Apo-2 antibody 3F11.39.7, in the absence of goat anti-mouse IgG Fc.

FIG. 9 is a bar diagram showing percent (%) apoptosis, as compared to Apo-2L, in 9D cells by Apo-2 antibody 3F11.39.7 in the presence or absence of goat anti-mouse IgG Fc.

FIG. 10 is a bar diagram illustrating the ability of Apo-2 antibody 3F11.39.7 to block the apoptosis induced by Apo-2L in 9D cells.

FIG. 11 is a graph showing results of an ELISA testing binding of Apo-2 antibody 3F11.39.7 to Apo-2 and to other known Apo-2L receptors referred to as DR4, DcR1, and DcR2.

FIG. 12A is a graph showing the results of an ELISA assay evaluating binding of the 16E2 antibody to Apo-2, DR4, DcR1, DcR2 and CD4-Ig.

FIG. 12B is a graph showing the results of an ELISA assay evaluating binding of the 20E6 antibody to Apo-2, DR4, DcR1, DcR2 and CD4-Ig.

FIG. 12C is a graph showing the results of an ELISA assay evaluating binding of the 24C4 antibody to Apo-2, DR4, DcR1, DcR2 and CD4-Ig.

FIG. 13B is a bar diagram showing agonistic activity of the 16E2 antibody, as compared to 7D5 scFv antibody (an anti-tissue factor antibody), in an apoptosis assay (crystal violet stain) using SK-MES-1 cells.

FIG. 13C is a bar diagram showing agonistic activity of the 16E2 antibody, as compared to 7D5 scFv antibody, in an apoptosis assay (annexin V-biotin/streptavidin-[$S^{35}$]) using SK-MES-1 cells.

FIG. 14A is a graph showing agonistic activity of the 20E6 antibody, as compared to Apo-2L, in an apoptosis assay (crystal violet stain) using SK-MES-1 cells.

FIG. 14B is a graph showing agonistic activity of the 20E6 antibody by a comparison between results obtained in the crystal violet and annexin V-biotin/streptavidin-[$S^{35}$] apoptosis assays.

FIG. 14C is a graph showing agonistic activity of gD-tagged 16E2 antibody, as compared to Apo-2L, in an apoptosis assay (crystal violet stain) using SK-MES-1 cells FIG. 15A shows the nucleotide sequence of the single chain antibody (scFv) fragment referred to as 16E2 (SEQ ID NO:6).

FIG. 15B shows the nucleotide sequence of the single chain antibody (scFv) fragment referred to as 20E6 (SEQ ID NO:7).

FIG. 15C shows the nucleotide sequence of the single chain antibody (scFv) fragment referred to as 24C4 (SEQ ID NO:8).

FIG. 16 shows the single chain antibody (scFv) fragments referred to as 16E2 (SEQ ID NO:9), 20E6 (SEQ ID NO:10), and 24C4 (SEQ ID NO:11), with the respective amino acid sequences for the signal sequence and the heavy and light chain CDR regions identified (CDR1, CDR2, and CDR3 regions are underlined).

DETAILED DESCRIPTION OF THE PREFERRED EMBODIMENTS

I. Definitions

Figure 13A:
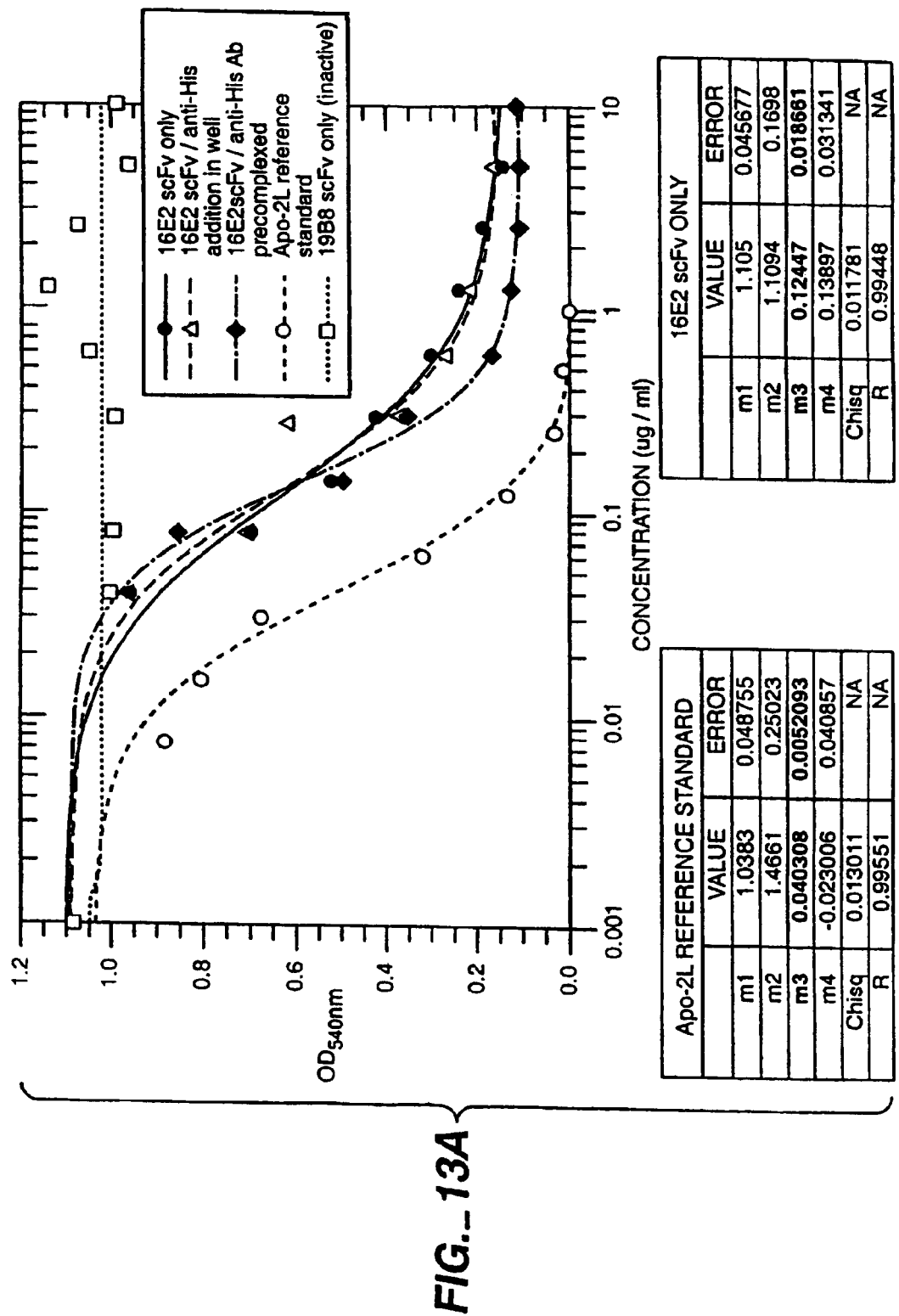
FIG. 13A is a graph showing agonistic activity of the 16E2 antibody, as compared to Apo-2L, in an apoptosis assay (crystal violet stain) using SK-MES-1 cells.

The terms "Apo-2 polypeptide" and "Apo-2" when used herein encompass native sequence Apo-2 and Apo-2 variants (which are further defined herein). These terms encompass Apo-2 from a variety of mammals, including humans. The Apo-2 may be isolated from a variety of sources, such as from human tissue types or from another source, or prepared by recombinant or synthetic methods.

A "native sequence Apo-2" comprises a polypeptide having the same amino acid sequence as an Apo-2 derived from nature. Thus, a native sequence Apo-2 can have the amino acid sequence of naturally-occurring Apo-2 from any mammal. Such native sequence Apo-2 can be isolated from nature or can be produced by recombinant or synthetic means. The term "native sequence Apo-2" specifically encompasses naturally-occurring truncated or secreted forms of the Apo-2 (e.g., an extracellular domain sequence), naturally-occurring variant forms (e.g., alternatively spliced forms) and naturally-occurring allelic variants of the Apo-2. A naturally-occurring variant form of the Apo-2 includes an Apo-2 having an amino acid substitution at residue 410 in the amino acid sequence shown in FIG. 1 (SEQ ID NO:1). In one embodiment of such naturally-occurring variant form, the leucine residue at position 410 is substituted by a methionine residue. In FIG. 1 (SEQ ID NO:1), the amino acid residue at position 410 is identified as "Xaa" to indicate that the amino acid may, optionally, be either leucine or methionine. In FIG. 1 (SEQ ID NO:2), the nucleotide at position 1367 is identified as "W" to indicate that the nucleotide may be either adenine (A) or thymine (T) or uracil (U). In one embodiment of the invention, the native sequence Apo-2 is a mature or full-length native sequence Apo-2 comprising amino acids 1 to 411 of FIG. 1 (SEQ ID NO:1). Optionally, the Apo-2 is obtained or obtainable by expressing the polypeptide encoded by the cDNA insert of the vector deposited as ATCC 209021.

The "Apo-2 extracellular domain" or "Apo-2 ECD" refers to a form of Apo-2 which is essentially free of the transmembrane and cytoplasmic domains of Apo-2. Ordinarily, Apo-2 ECD will have less than 1% of such transmembrane and/or cytoplasmic domains and preferably, will have less than 0.5% of such domains. Optionally, Apo-2 ECD will comprise amino acid residues 54 to 182 of FIG. 1 (SEQ ID NO:1) or amino acid residues 1 to 182 of FIG. 1 (SEQ ID NO:1). Optionally, Apo-2 ECD will comprise one or more cysteine-rich domains, and preferably, one or both of the cysteine-rich domains identified herein (see FIG. 2A). It will be understood by the skilled artisan that the transmembrane domain identified for the Apo-2 polypeptide herein is identified pursuant to criteria routinely employed in the art for identifying that type of hydrophobic domain. The exact boundaries of a transmembrane domain may vary but most likely by no more than about 5 amino acids at either end of the domain specifically mentioned herein.

"Apo-2 variant" means a biologically active Apo-2 as defined below having at least about 80% amino acid sequence identity with the Apo-2 having the deduced amino acid sequence shown in FIG. 1 (SEQ ID NO:1) for a full-length native sequence human Apo-2 or the sequences identified herein for Apo-2 ECD or death domain. Such Apo-2 variants include, for instance, Apo-2 polypeptides wherein one or more amino acid residues are added, or deleted, at the N- or C-terminus of the sequence of FIG. 1 (SEQ ID NO:1) or the sequences identified herein for Apo-2 ECD or death domain. Ordinarily, an Apo-2 variant will have at least about 80% amino acid sequence identity, more preferably at least about 90% amino acid sequence identity, and even more preferably at least about 95% amino acid sequence identity with the amino acid sequence of FIG. 1 (SEQ ID NO:1) or the sequences identified herein for Apo-2 ECD or death domain.

"Percent (%) amino acid sequence identity" with respect to the Apo-2 sequences identified herein is defined as the percentage of amino acid residues in a candidate sequence that are identical with the amino acid residues in the Apo-2 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN™ or Megalign (DNASTAR) software. Those skilled in the art can determine appropriate parameters for measuring alignment, including any algorithms needed to achieve maximal alignment over the full length of the sequences being compared.

The term "epitope tagged" when used herein refers to a chimeric polypeptide comprising Apo-2 or Apo-2 antibody, or a domain sequence thereof, fused to a "tag polypeptide". The tag polypeptide has enough residues to provide an epitope against which an antibody can be made, yet is short enough such that it does not interfere with activity of the Apo-2 or Apo-2 antibody. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the Apo-2 natural environment will not be present. Ordinarily, however, isolated polypeptide will be prepared by at least one purification step.

An "isolated" Apo-2 nucleic acid molecule is a nucleic acid molecule that is identified and separated from at least one contaminant nucleic acid molecule with which it is ordinarily associated in the natural source of the Apo-2 nucleic acid. An isolated Apo-2 nucleic acid molecule is other than in the form or setting in which it is found in nature. Isolated Apo-2 nucleic acid molecules therefore are distinguished from the Apo-2 nucleic acid molecule as it exists in natural cells. However, an isolated Apo-2 nucleic acid molecule includes Apo-2 nucleic acid molecules contained in cells that ordinarily express Apo-2 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers anti-Apo-2 monoclonal antibodies (including agonist, antagonist, and blocking or neutralizing antibodies) and anti-Apo-2 antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-Apo-2 antibody with a constant domain, or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. See, e.g. U.S. Pat. No. 4,816,567 and Mage et al., in *Monoclonal Antibody Production Techniques and Applications*, pp. 79-97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552-554 (1990), for example.

"Single-chain Fv" or "scFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see, e.g., Pluckthun, *The Pharmacology of Monoclonal Antibodies*, vol. 113, Rosenburg and Moore eds. Springer-Verlag, New York, pp. 269-315 (1994). The scFv antibody fragments of the present invention include but are not limited to the 16E2, 20E6 and 24C4 antibodies described in detail below. Within the scope of the scFv antibodies of the invention are scFv antibodies comprising VH and VL domains that include one or more of the CDR regions identified for the 16E2, 20E6 and 24C4 antibodies.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

"Biologically active" and "desired biological activity" for the purposes herein means (1) having the ability to modulate apoptosis (either in an agonistic or stimulating manner or in an antagonistic or blocking manner) in at least one type of mammalian cell in vivo or ex vivo; (2) having the ability to bind Apo-2 ligand; or (3) having the ability to modulate Apo-2 ligand signaling and Apo-2 ligand activity.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis, all of which are known in the art.

The terms "treating," "treatment," and "therapy" as used herein refer to curative therapy, prophylactic therapy, and preventative therapy.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, blastoma, gastrointestinal cancer, renal cancer, pancreatic cancer, glioblastoma, neuroblastoma, cervical cancer, ovarian cancer, liver cancer, stomach cancer, bladder cancer, hepatoma, breast cancer, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer.

The term "mammal" as used herein refers to any mammal classified as a mammal, including humans, cows, horses, dogs and cats. In a preferred embodiment of the invention, the mammal is a human.

II. Compositions and Methods of the Invention

The present invention provides newly identified and isolated Apo-2 polypeptides and Apo-2 antibodies. In particular, Applicants have identified and isolated various human Apo-2 polypeptides. The properties and characteristics of some of these Apo-2 polypeptides and anti-Apo-2 antibodies are described in further detail in the Examples below. Based upon the properties and characteristics of the Apo-2 polypeptides disclosed herein, it is Applicants' present belief that Apo-2 is a member of the TNFR family.

A description follows as to how Apo-2, as well as Apo-2 chimeric molecules and anti-Apo-2 antibodies, may be prepared.

A. Preparation of Apo-2

The description below relates primarily to production of Apo-2 by culturing cells transformed or transfected with a vector containing Apo-2 nucleic acid. It is of course, contemplated that alternative methods, which are well known in the art, may be employed to prepare Apo-2.

1. Isolation of DNA Encoding Apo-2

The DNA encoding Apo-2 may be obtained from any cDNA library prepared from tissue believed to possess the Apo-2 mRNA and to express it at a detectable level. Accordingly, human Apo-2 DNA can be conveniently obtained from a cDNA library prepared from human tissues, such as the bacteriophage libraries of human pancreas and kidney cDNA described in Example 1. The Apo-2-encoding gene may also be obtained from a genomic library or by oligonucleotide synthesis.

Libraries can be screened with probes (such as antibodies to the Apo-2 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding Apo-2 is to use PCR methodology [Sambrook et al., supra; Dieffenbach et al., *PCR Primer: A Laboratory Manual* (Cold Spring Harbor Laboratory Press, 1995)].

A preferred method of screening employs selected oligonucleotide sequences to screen cDNA libraries from various human tissues. Example 1 below describes techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Nucleic acid having all the protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

Apo-2 variants can be prepared by introducing appropriate nucleotide changes into the Apo-2 DNA, or by synthesis of the desired Apo-2 polypeptide. Those skilled in the art will appreciate that amino acid changes may alter post-translational processes of the Apo-2, such as changing the number or position of glycosylation sites or altering the membrane anchoring characteristics.

Variations in the native full-length sequence Apo-2 or in various domains of the Apo-2 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the Apo-2 that results in a change in the amino acid sequence of the Apo-2 as compared with the native sequence Apo-2. Optionally the variation is by substitution of at least one amino acid with any other amino acid in one or more of the domains of the Apo-2 molecule. The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the Apo-2 variant DNA.

Scanning amino acid analysis can also be employed to identify one or more amino acids along a contiguous sequence which are involved in the interaction with a particular ligand or receptor. Among the preferred scanning amino acids are relatively small, neutral amino acids. Such amino acids include alanine, glycine, serine, and cysteine. Alanine is the preferred scanning amino acid among this group because it eliminates the side-chain beyond the beta-carbon and is less likely to alter the main-chain conformation of the variant. Alanine is also preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Once selected Apo-2 variants are produced, they can be contacted with, for instance, Apo-2L, and the interaction, if any, can be determined. The interaction between the Apo-2 variant and Apo-2L can be measured by an in vitro assay, such as described in the Examples below. While any number of analytical measurements can be used to compare activities and properties between a native sequence Apo-2 and an Apo-2 variant, a convenient one for binding is the dissociation constant $K_d$ of the complex formed between the Apo-2 variant and Apo-2L as compared to the $K_d$ for the native sequence Apo-2. Generally, a $\geq$3-fold increase or decrease in $K_d$ per substituted residue indicates that the substituted residue(s) is active in the interaction of the native sequence Apo-2 with the Apo-2L.

Optionally, representative sites in the Apo-2 sequence suitable for mutagenesis would include sites within the extracellular domain, and particularly, within one or both of the cysteine-rich domains. Such variations can be accomplished using the methods described above.

2. Insertion of Nucleic Acid into a Replicable Vector

The nucleic acid (e.g., cDNA or genomic DNA) encoding Apo-2 may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below.

(i) Signal Sequence Component

The Apo-2 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the Apo-2 DNA that is inserted into the vector. The heterologous signal sequence selected preferably is one that is recognized and processed (i.e., cleaved by a signal peptidase) by the host cell. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression the native Apo-2 presequence that normally directs insertion of Apo-2 in the cell membrane of human cells in vivo is satisfactory, although other mammalian signal sequences may be used to direct secretion of the protein, such as signal sequences from secreted polypeptides of the same or related species, as well as viral secretory leaders, for example, the herpes simplex glycoprotein D signal.

The DNA for such precursor region is preferably ligated in reading frame to DNA encoding Apo-2.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of Apo-2 DNA. However, the recovery of genomic DNA encoding Apo-2 is more complex than that of an exogenously replicated vector because restriction enzyme digestion is required to excise the Apo-2 DNA.

(iii) Selection Gene Component

Expression and cloning vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin [Southern et al., *J. Molec. Appl. Genet.*, 1:327 (1982)], mycophenolic acid (Mulligan et al., *Science*, 209:1422 (1980)] or hygromycin [Sugden et al., Mol. Cell. Biol., 5:410-413 (1985)]. The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the Apo-2 nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes Apo-2. Amplification is the process by which genes in greater demand for the production of a protein critical for growth are reiterated in tandem within the chromosomes of successive generations of recombinant cells. Increased quantities of Apo-2 are synthesized from the amplified DNA. Other examples of amplifiable genes include metallothionein-I and -II, adenosine deaminase, and ornithine decarboxylase.

Cells transformed with the DHFR selection gene may first be identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding Apo-2. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding Apo-2, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)]. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts [Bianchi et al., *Curr. Genet.*, 12:185 (1987)]. More recently, an expression system for large-scale production of recombinant calf chymosin was reported for *K. lactis* [Van den Berg, *Bio/Technology*, 8:135 (1990)]. Stable multi-copy expression vectors for secretion of mature recombinant human serum albumin by industrial strains of *Kluyveromyces* have also been disclosed [Fleer et al., *Bio/Technology*, 9:968-975 (1991)].

(iv) Promoter Component

Expression and cloning vectors usually contain a promoter that is recognized by the host organism and is operably linked to the Apo-2 nucleic acid sequence. Promoters are untranslated sequences located upstream (5') to the start codon of a structural gene (generally within about 100 to 1000 bp) that control the transcription and translation of particular nucleic acid sequence, such as the Apo-2 nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Apo-2 encoding DNA by removing the promoter from the source DNA by restriction enzyme digestion and inserting the isolated promoter sequence into the vector. Both the native Apo-2 promoter sequence and many heterologous promoters may be used to direct amplification and/or expression of the Apo-2 DNA.

Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776]), and hybrid promoters such as the tac promoter [deBoer et al., Proc. Natl. Acad. Sci. USA, 80:21-25 (1983)]. However, other known bacterial promoters are suitable. Their nucleotide sequences have been published, thereby enabling a skilled worker operably to ligate them to DNA encoding Apo-2 [Siebenlist et al., Cell, 20:269 (1980)] using linkers or adaptors to supply any required restriction sites. Promoters for use in bacterial systems also will contain a Shine-Dalgarno (S.D.) sequence operably linked to the DNA encoding Apo-2.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Apo-2 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the Apo-2 sequence, provided such promoters are compatible with the host cell systems.

The early and late promoters of the SV40 virus are conveniently obtained as an SV40 restriction fragment that also contains the SV40 viral origin of replication [Fiers et al., Nature, 273:113 (1978); Mulligan and Berg, Science, 209: 1422-1427 (1980); Pavlakis et al., Proc. Natl. Acad. Sci. USA, 78:7398-7402 (1981)]. The immediate early promoter of the human cytomegalovirus is conveniently obtained as a HindIII E restriction fragment [Greenaway et al., Gene, 18:355-360 (1982)]. A system for expressing DNA in mammalian hosts using the bovine papilloma virus as a vector is disclosed in U.S. Pat. No. 4,419,446. A modification of this system is described in U.S. Pat. No. 4,601,978 [See also Gray et al., Nature, 295:503-508 (1982) on expressing cDNA encoding immune interferon in monkey cells; Reyes et al., Nature, 297:598-601 (1982) on expression of human β-interferon cDNA in mouse cells under the control of a thymidine kinase promoter from herpes simplex virus; Canaani and Berg, Proc. Natl. Acad. Sci. USA 79:5166-5170 (1982) on expression of the human interferon gene in cultured mouse and rabbit cells; and Gorman et al., Proc. Natl. Acad. Sci. USA, 79:6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter).

(v) Enhancer Element Component

Transcription of a DNA encoding the Apo-2 of this invention by higher eukaryotes may be increased by inserting an enhancer sequence into the vector. Enhancers are cis-acting elements of DNA, usually about from 10 to 300 bp, that act on a promoter to increase its transcription. Enhancers are relatively orientation and position independent, having been found 5' [Laimins et al., Proc. Natl. Acad. Sci. USA, 78:993 (1981]) and 3' [Lusky et al., Mol. Cell Bio., 3:1108 (1983]) to the transcription unit, within an intron [Banerji et al., Cell, 33:729 (1983)], as well as within the coding sequence itself [Osborne et al., Mol. Cell Bio., 4:1293 (1984)]. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the Apo-2 coding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Apo-2.

(vii) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9:309 (1981) or by the method of Maxim et al., *Methods in Enzymology*, 65:499 (1980).

(viii) Transient Expression Vectors

Expression vectors that provide for the transient expression in mammalian cells of DNA encoding Apo-2 may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector [Sambrook et al., supra]. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying Apo-2 variants.

(ix) Suitable Exemplary Vertebrate Cell Vectors

Other methods, vectors, and host cells suitable for adaptation to the synthesis of Apo-2 in recombinant vertebrate cell culture are described in Gething et al., *Nature*, 293:620-625 (1981); Mantei et al., *Nature*, 281:40-46 (1979); EP 117,060; and EP 117,058.

3. Selection and Transformation of Host Cells

Suitable host cells for cloning or expressing the DNA in the vectors herein are the prokaryote, yeast, or higher eukaryote cells described above. Suitable prokaryotes for this purpose include but are not limited to eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Preferably, the host cell should secrete minimal amounts of proteolytic enzymes.

In addition to prokaryotes, eukaryotic microbes such as filamentous fungi or yeast are suitable cloning or expression hosts for Apo-2-encoding vectors. *Saccharomyces cerevisiae*, or common baker's yeast, is the most commonly used among lower eukaryotic host microorganisms. However, a number of other genera, species, and strains are commonly available and useful herein.

Suitable host cells for the expression of glycosylated Apo-2 are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified [See, e.g., Luckow et al., *Bio/Technology*, 6:47-55 (1988); Miller et al., in *Genetic Engineering*, Setlow et al., eds., Vol. 8 (Plenum Publishing, 1986), pp. 277-279; and Maeda et al., *Nature*, 315:592-594 (1985)]. A variety of viral strains for transfection are publicly available, e.g., the L-1 variant of *Autographa californica* NPV and the Bm-5 strain of *Bombyx mori* NPV.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*. During incubation of the plant cell culture with *A. tumefaciens*, the DNA encoding the Apo-2 can be transferred to the plant cell host such that it is transfected, and will, under appropriate conditions, express the Apo-2-encoding DNA. In addition, regulatory and signal sequences compatible with plant cells are available, such as the nopaline synthase promoter and polyadenylation signal sequences [Depicker et al., *J. Mol. Appl. Gen.*, 1:561 (1982)]. In addition, DNA segments isolated from the upstream region of the T-DNA 780 gene are capable of activating or increasing transcription levels of plant-expressible genes in recombinant DNA-containing plant tissue [EP 321,196 published 21 Jun. 1989].

Propagation of vertebrate cells in culture (tissue culture) is also well known in the art [See, e.g., *Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen. Virol.*, 36:59 (1977)); baby hamster kidney cells (BHK, ATCC CCL 10); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68 (1982)); MRC 5 cells; and FS4 cells.

Host cells are transfected and preferably transformed with the above-described expression or cloning vectors for Apo-2 production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology*, 52:456-457 (1978) is preferred. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336: 348-352 (1988).

4. Culturing the Host Cells

Prokaryotic cells used to produce Apo-2 may be cultured in suitable media as described generally in Sambrook et al., supra.

The mammalian host cells used to produce Apo-2 may be cultured in a variety of media. Examples of commercially available media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Various labels may be employed, most commonly radioisotopes, and particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, or luminescent labels.

Antibodies useful for immunohistochemical staining and/or assay of sample fluids may be either monoclonal or polyclonal, and may be prepared in any mammal. Conveniently, the antibodies may be prepared against a native sequence Apo-2 polypeptide or against a synthetic peptide based on the DNA sequences provided herein or against exogenous sequence fused to Apo-2 DNA and encoding a specific antibody epitope.

6. Purification of Apo-2 Polypeptide

Forms of Apo-2 may be recovered from culture medium or from host cell lysates. If the Apo-2 is membrane-bound, it can be released from the membrane using a suitable detergent solution (e.g. Triton-X 100) or its extracellular domain may be released by enzymatic cleavage.

When Apo-2 is produced in a recombinant cell other than one of human origin, the Apo-2 is free of proteins or polypeptides of human origin. However, it may be desired to purify Apo-2 from recombinant cell proteins or polypeptides to obtain preparations that are substantially homogeneous as to Apo-2. As a first step, the culture medium or lysate may be centrifuged to remove particulate cell debris. Apo-2 thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

Apo-2 variants in which residues have been deleted, inserted, or substituted can be recovered in the same fashion as native sequence Apo-2, taking account of changes in properties occasioned by the variation. For example, preparation of an Apo-2 fusion with another protein or polypeptide, e.g., a bacterial or viral antigen, immunoglobulin sequence, or receptor sequence, may facilitate purification; an immunoaffinity column containing antibody to the sequence can be used to adsorb the fusion polypeptide. Other types of affinity matrices also can be used.

A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native sequence Apo-2 may require modification to account for changes in the character of Apo-2 or its variants upon expression in recombinant cell culture.

7. Covalent Modifications of Apo-2 Polypeptides

Covalent modifications of Apo-2 are included within the scope of this invention. One type of covalent modification of the Apo-2 is introduced into the molecule by reacting targeted amino acid residues of the Apo-2 with an organic derivatizing agent that is capable of reacting with selected side chains or the N- or C-terminal residues of the Apo-2.

Derivatization with bifunctional agents is useful for crosslinking Apo-2 to a water-insoluble support matrix or surface for use in the method for purifying anti-Apo-2 antibodies, and vice-versa. Derivatization with one or more bifunctional agents will also be useful for crosslinking Apo-2 molecules to generate Apo-2 dimers. Such dimers may increase binding avidity and extend half-life of the molecule in vivo. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)-dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group. The modified forms of the residues fall within the scope of the present invention.

Another type of covalent modification of the Apo-2 polypeptide included within the scope of this invention comprises altering the native glycosylation pattern of the polypeptide. "Altering the native glycosylation pattern" is intended for purposes herein to mean deleting one or more carbohydrate moieties found in native sequence Apo-2, and/or adding one or more glycosylation sites that are not present in the native sequence Apo-2.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the Apo-2 polypeptide may be accomplished by altering the amino acid sequence such that it contains one or more of the above-described tripeptide sequences (for N-linked glycosylation sites). The alteration may also be made by the addition of, or substitution by, one or more serine or threonine residues to the native sequence Apo-2 (for O-linked glycosylation sites). The Apo-2 amino acid sequence may optionally be altered through changes at the DNA level, particularly by mutating the DNA encoding the Apo-2 polypeptide at preselected bases such that codons are generated that will translate into the desired amino acids. The DNA mutation(s) may be made using methods described above and in U.S. Pat. No. 5,364,934, supra.

Another means of increasing the number of carbohydrate moieties on the Apo-2 polypeptide is by chemical or enzymatic coupling of glycosides to the polypeptide. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259-306 (1981).

Removal of carbohydrate moieties present on the Apo-2 polypeptide may be accomplished chemically or enzymatically or by mutational substitution of codons encoding for amino acid residues that serve as targets for glycosylation. For instance, chemical deglycosylation by exposing the polypeptide to the compound trifluoromethanesulfonic acid, or an equivalent compound can result in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Glycosylation at potential glycosylation sites may be prevented by the use of the compound tunicamycin as described by Duksin et al., *J. Biol. Chem.*, 257:3105 (1982). Tunicamycin blocks the formation of protein-N-glycoside linkages.

Another type of covalent modification of Apo-2 comprises linking the Apo-2 polypeptide to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

8. Apo-2 Chimeras

The present invention also provides chimeric molecules comprising Apo-2 fused to another, heterologous polypeptide or amino acid sequence.

In one embodiment, the chimeric molecule comprises a fusion of the Apo-2 with a tag polypeptide which provides an epitope to which an anti-tag antibody can selectively bind. The epitope tag is generally placed at the amino- or carboxyl-terminus of the Apo-2. The presence of such epitope-tagged forms of the Apo-2 can be detected using an antibody against the tag polypeptide. Also, provision of the epitope tag enables the Apo-2 to be readily purified by affinity purification using an anti-tag antibody or another type of affinity matrix that binds to the epitope tag.

Various tag polypeptides and their respective antibodies are well known in the art. Examples include the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)]. Once the tag polypeptide has been selected, an antibody thereto can be generated using the techniques disclosed herein.

Generally, epitope-tagged Apo-2 may be constructed and produced according to the methods described above. Epitope-tagged Apo-2 is also described in the Examples below. Apo-2-tag polypeptide fusions are preferably constructed by fusing the cDNA sequence encoding the Apo-2 portion in-frame to the tag polypeptide DNA sequence and expressing the resultant DNA fusion construct in appropriate host cells. Ordinarily, when preparing the Apo-2-tag polypeptide chimeras of the present invention, nucleic acid encoding the Apo-2 will be fused at its 3' end to nucleic acid encoding the N-terminus of the tag polypeptide, however 5' fusions are also possible. For example, a polyhistidine sequence of about 5 to about 10 histidine residues may be fused at the N-terminus or the C-terminus and used as a purification handle in affinity chromatography.

Epitope-tagged Apo-2 can be purified by affinity chromatography using the anti-tag antibody. The matrix to which the affinity antibody is attached may include, for instance, agarose, controlled pore glass or poly(styrenedivinyl)benzene. The epitope-tagged Apo-2 can then be eluted from the affinity column using techniques known in the art.

In another embodiment, the chimeric molecule comprises an Apo-2 polypeptide fused to an immunoglobulin sequence. The chimeric molecule may also comprise a particular domain sequence of Apo-2, such as an extracellular domain sequence of Apo-2 fused to an immunoglobulin sequence. This includes chimeras in monomeric, homo- or heteromultimeric, and particularly homo- or heterodimeric, or -tetrameric forms; optionally, the chimeras may be in dimeric forms or homodimeric heavy chain forms. Generally, these assembled immunoglobulins will have known unit structures as represented by the following diagrams.

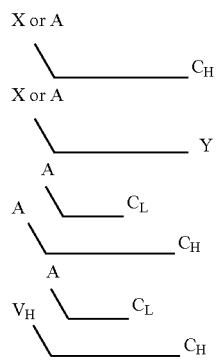

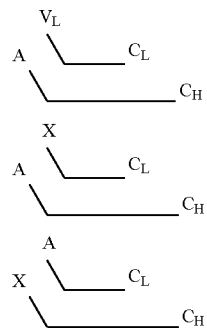

A basic four chain structural unit is the form in which IgG, IgD, and IgE exist. A four chain unit is repeated in the higher molecular weight immunoglobulins; IgM generally exists as a pentamer of basic four-chain units held together by disulfide bonds. IgA globulin, and occasionally IgG globulin, may also exist in a multimeric form in serum. In the case of multimers, each four chain unit may be the same or different.

The following diagrams depict some exemplary monomer, homo- and heterodimer and homo- and heteromultimer structures. These diagrams are merely illustrative, and the chains of the multimers are believed to be disulfide bonded in the same fashion as native immunoglobulins.

monomer:

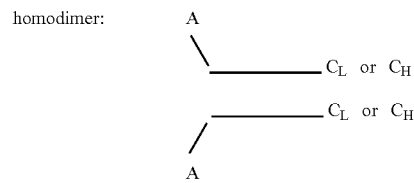

homodimer:

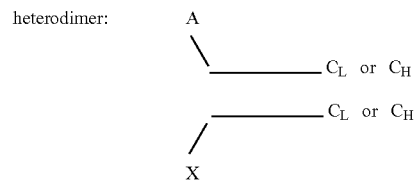

heterodimer:

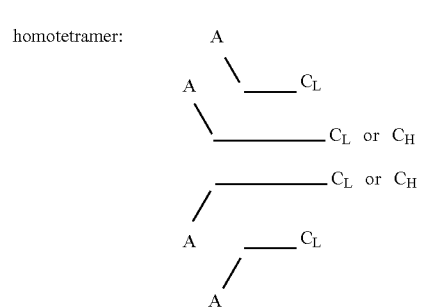

homotetramer:

heterotetramer:
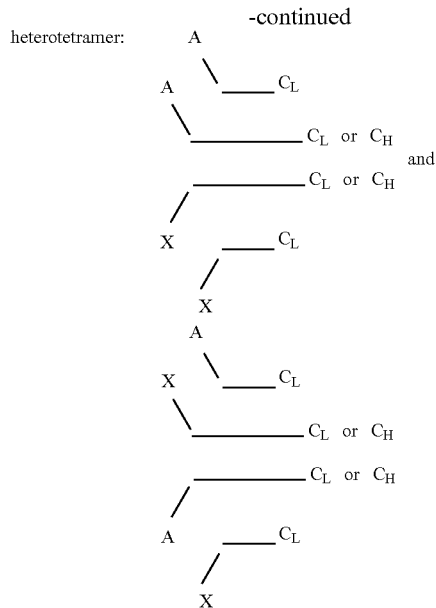

In the foregoing diagrams, "A" means an Apo-2 sequence or an Apo-2 sequence fused to a heterologous sequence; X is an additional agent, which may be the same as A or different, a portion of an immunoglobulin superfamily member such as a variable region or a variable region-like domain, including a native or chimeric immunoglobulin variable region, a toxin such a pseudomonas exotoxin or ricin, or a sequence functionally binding to another protein, such as other cytokines (i.e., IL-1, interferon-γ) or cell surface molecules (i.e., NGFR, CD40, OX40, Fas antigen, T2 proteins of Shope and myxoma poxviruses), or a polypeptide therapeutic agent not otherwise normally associated with a constant domain; Y is a linker or another receptor sequence; and $V_L$, $V_H$, $C_L$ and $C_H$ represent light or heavy chain variable or constant domains of an immunoglobulin. Structures comprising at least one CRD of an Apo-2 sequence as "A" and another cell-surface protein having a repetitive pattern of CRDs (such as TNFR) as "X" are specifically included.

It will be understood that the above diagrams are merely exemplary of the possible structures of the chimeras of the present invention, and do not encompass all possibilities. For example, there might desirably be several different "A"s, "X"s, or "Y"s in any of these constructs. Also, the heavy or light chain constant domains may be originated from the same or different immunoglobulins. All possible permutations of the illustrated and similar structures are all within the scope of the invention herein.

In general, the chimeric molecules can be constructed in a fashion similar to chimeric antibodies in which a variable domain from an antibody of one species is substituted for the variable domain of another species. See, for example, EP 0 125 023; EP 173,494; Munro, Nature, 312:597 (13 Dec. 1984); Neuberger et al., Nature, 312:604-608 (13 Dec. 1984); Sharon et al., Nature, 309:364-367 (24 May 1984); Morrison et al., Proc. Nat'l. Acad. Sci. USA, 81:6851-6855 (1984); Morrison et al., Science, 229:1202-1207 (1985); Boulianne et al., Nature, 312:643-646 (13 Dec. 1984); Capon et al., Nature, 337:525-531 (1989); Traunecker et al., Nature, 339:68-70 (1989).

Alternatively, the chimeric molecules may be constructed as follows. The DNA including a region encoding the desired sequence, such as an Apo-2 and/or TNFR sequence, is cleaved by a restriction enzyme at or proximal to the 3' end of the DNA encoding the immunoglobulin-like domain(s) and at a point at or near the DNA encoding the N-terminal end of the Apo-2 or TNFR polypeptide (where use of a different leader is contemplated) or at or proximal to the N-terminal coding region for TNFR (where the native signal is employed). This DNA fragment then is readily inserted proximal to DNA encoding an immunoglobulin light or heavy chain constant region and, if necessary, the resulting construct tailored by deletional mutagenesis. Preferably, the Ig is a human immunoglobulin when the chimeric molecule is intended for in vivo therapy for humans. DNA encoding immunoglobulin light or heavy chain constant regions is known or readily available from cDNA libraries or is synthesized. See for example, Adams et al., Biochemistry, 19:2711-2719 (1980); Gough et al., Biochemistry, 19:2702-2710 (1980); Dolby et al., Proc. Natl. Acad. Sci. USA, 77:6027-6031 (1980); Rice et al., Proc. Natl. Acad. Sci., 79:7862-7865 (1982); Falkner et al., Nature, 298:286-288 (1982); and Morrison et al., Ann. Rev. Immunol., 2:239-256 (1984).

Further details of how to prepare such fusions are found in publications concerning the preparation of immunoadhesins. Immunoadhesins in general, and CD4-Ig fusion molecules specifically are disclosed in WO 89/02922, published 6 Apr. 1989. Molecules comprising the extracellular portion of CD4, the receptor for human immunodeficiency virus (HIV), linked to IgG heavy chain constant region are known in the art and have been found to have a markedly longer half-life and lower clearance than the soluble extracellular portion of CD4 [Capon et al., supra; Byrn et al., Nature, 344:667 (1990)]. The construction of specific chimeric TNFR-IgG molecules is also described in Ashkenazi et al. Proc. Natl. Acad. Sci., 88:10535-10539 (1991); Lesslauer et al. [J. Cell. Biochem. Supplement 15F, 1991, p. 115 (P 432)]; and Peppel and Beutler, J. Cell. Biochem. Supplement 15F, 1991, p. 118 (P 439)].

B. Therapeutic and Non-Therapeutic Uses for Apo-2

Apo-2, as disclosed in the present specification, can be employed therapeutically to induce apoptosis in mammalian cells. This therapy can be accomplished for instance, using in vivo or ex vivo gene therapy techniques and includes the use of the death domain sequences disclosed herein. The Apo-2 chimeric molecules (including the chimeric molecules containing an extracellular domain sequence of Apo-2) comprising immunoglobulin sequences can also be employed therapeutically to inhibit apoptosis or NF-KB induction by Apo-2L or by another ligand that Apo-2 binds to.

The Apo-2 of the invention also has utility in non-therapeutic applications. Nucleic acid sequences encoding the Apo-2 may be used as a diagnostic for tissue-specific typing. For example, procedures like in situ hybridization, Northern and Southern blotting, and PCR analysis may be used to determine whether DNA and/or RNA encoding Apo-2 is present in the cell type(s) being evaluated. Apo-2 nucleic acid will also be useful for the preparation of Apo-2 by the recombinant techniques described herein.

The isolated Apo-2 may be used in quantitative diagnostic assays as a control against which samples containing unknown quantities of Apo-2 may be prepared. Apo-2 preparations are also useful in generating antibodies, as standards in assays for Apo-2 (e.g., by labeling Apo-2 for use as a standard in a radioimmunoassay, radioreceptor assay, or enzyme-linked immunoassay), in affinity purification techniques, and in competitive-type receptor binding assays when labeled with, for instance, radioiodine, enzymes, or fluorophores.

Modified forms of the Apo-2, such as the Apo-2-IgG chimeric molecules (immunoadhesins) described above, can be used as immunogens in producing anti-Apo-2 antibodies.

Nucleic acids which encode Apo-2 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding Apo-2 or an appropriate sequence thereof (such as Apo-2-IgG) can be used to clone genomic DNA encoding Apo-2 in accordance with established techniques and the genomic sequences used to generate transgenic animals that contain cells which express DNA encoding Apo-2. Methods for generating transgenic animals, particularly animals such as mice or rats, have become conventional in the art and are described, for example, in U.S. Pat. Nos. 4,736,866 and 4,870,009. Typically, particular cells would be targeted for Apo-2 transgene incorporation with tissue-specific enhancers. Transgenic animals that include a copy of a transgene encoding Apo-2 introduced into the germ line of the animal at an embryonic stage can be used to examine the effect of increased expression of DNA encoding Apo-2. Such animals can be used as tester animals for reagents thought to confer protection from, for example, pathological conditions associated with excessive apoptosis. In accordance with this facet of the invention, an animal is treated with the reagent and a reduced incidence of the pathological condition, compared to untreated animals bearing the transgene, would indicate a potential therapeutic intervention for the pathological condition. In another embodiment, transgenic animals that carry a soluble form of Apo-2 such as an Apo-2 ECD or an immunoglobulin chimera of such form could be constructed to test the effect of chronic neutralization of Apo-2L, a ligand of Apo-2.

Alternatively, non-human homologues of Apo-2 can be used to construct an Apo-2 "knock out" animal which has a defective or altered gene encoding Apo-2 as a result of homologous recombination between the endogenous gene encoding Apo-2 and altered genomic DNA encoding Apo-2 introduced into an embryonic cell of the animal. For example, cDNA encoding Apo-2 can be used to clone genomic DNA encoding Apo-2 in accordance with established techniques. A portion of the genomic DNA encoding Apo-2 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the Apo-2 polypeptide, including for example, development of tumors.

C. Anti-Apo-2 Antibody Preparation

The present invention further provides anti-Apo-2 antibodies. Antibodies against Apo-2 may be prepared as follows. Exemplary antibodies include polyclonal, monoclonal, humanized, bispecific, and heteroconjugate antibodies.

1. Polyclonal Antibodies

The Apo-2 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Apo-2 polypeptide or a fusion protein thereof. An example of a suitable immunizing agent is an Apo-2-IgG fusion protein, such as an Apo-2 ECD-IgG fusion protein. Cells expressing Apo-2 at their surface may also be employed. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean trypsin inhibitor. An aggregating agent such as alum may also be employed to enhance the mammal's immune response. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for antibody titer. If desired, the mammal can be boosted until the antibody titer increases or plateaus.

2. Monoclonal Antibodies

The Apo-2 antibodies may, alternatively, be monoclonal antibodies. Monoclonal antibodies may be prepared using hybridoma methods, such as those described by Kohler and Milstein, supra. In a hybridoma method, a mouse, hamster, or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

The immunizing agent will typically include the Apo-2 polypeptide or a fusion protein thereof. An example of a suitable immunizing agent is an Apo-2-IgG fusion protein or chimeric molecule. A specific example of an Apo-2 ECD-IgG immunogen is described in Example 9 below. Cells expressing Apo-2 at their surface may also be employed. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental transformed cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against Apo-2. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

As described in the Examples below, anti-Apo-2 monoclonal antibodies have been prepared. One of these antibodies, 3F11.39.7, has been deposited with ATCC and has been assigned deposit accession no. HB-12456. In one embodiment, the monoclonal antibodies of the invention will have the same biological characteristics as the monoclonal antibodies secreted by the hybridoma cell line(s) deposited under Accession No. HB-12456. The term "biological characteristics" is used to refer to the in vitro and/or in vivo activities or properties of the monoclonal antibody, such as the ability to specifically bind to Apo-2 or to substantially block, induce or enhance Apo-2 activation. As disclosed in the present specification, the 3F11.39.7 monoclonal antibody (HB-12456) is characterized as having agonistic activity for inducing apoptosis, binding to the Apo-2 receptor, having blocking activity as described in the Examples below, and having some cross-reactivity to DR4 but not to DcR1 or DcR2. Optionally, the monoclonal antibody will bind to the same epitope as the 3F11.39.7 antibody disclosed herein. This can be determined by conducting various assays, such as described herein and in the Examples. For instance, to determine whether a monoclonal antibody has the same specificity as the 3F11.39.7 antibody specifically disclosed, one can compare activity in Apo-2 blocking and apoptosis induction assays, such as those described in the Examples below.

The antibodies of the invention may also comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published 12/22/94 and U.S. Pat. No. 4,342,566. Papain digestion of antibodies typically produces two identical antigen binding fragments, called Fab fragments, each with a single antigen binding site, and a residual Fc fragment. Pepsin treatment yields an $F(ab')_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

3. Humanized Antibodies

The Apo-2 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody [Sims et al., J. Immunol., 151:2296 (1993); Chothia and Lesk, J. Mol. Biol., 196:901 (1987)]. Another method uses a particular framework derived from the consensus sequence of all human antibodies of a particular subgroup of light or heavy chains. The same framework may be used for several different humanized antibodies [Carter et al., Proc. Natl. Acad. Sci. USA, 89:4285 (1992); Presta et al., J. Immunol., 151:2623 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding [see, WO 94/04679 published 3 Mar. 1994].

Transgenic animals (e.g., mice) that are capable, upon immunization, of producing a full repertoire of human antibodies in the absence of endogenous immunoglobulin production can be employed. Transfer of the human germ-line immunoglobulin gene array in such germ-line mutant mice will result in the production of human antibodies upon antigen challenge [see, e.g., Jakobovits et al., Proc. Natl. Acad. Sci. USA, 90:2551-255 (1993); Jakobovits et al., Nature, 362: 255-258 (1993); Bruggemann et al., Year in Immuno., 7:33 (1993)].

Human antibodies can also be produced in phage display libraries [Hoogenboom and Winter, J. Mol. Biol., 227:381 (1992); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1) :86-95 (1991)]. Suitable methods for preparing phage libraries have been reviewed and are described in Winter et al., Annu. Rev. Immunol., 12:433-55 (1994); Soderlind et al., Immunological Reviews, 130:109-123 (1992); Hoogenboom, Tibtech February 1997, Vol. 15; Neri et al., Cell Biophysics, 27:47-61 (1995). Libraries of single chain antibodies may also be prepared by the methods described in WO 92/01047, WO 92/20791, WO 93/06213, WO 93/11236, WO 93/19172, WO 95/01438 and WO 95/15388. Antibody libraries are also commercially available, for example, from Cambridge Antibody Technologies (C.A.T.), Cambridge, UK. Binding selection against an antigen, in this case Apo-2, can be carried out as described in greater detail in the Examples below.

As described in the Examples below, anti-Apo-2 single-chain Fv (scFv) antibodies have been identified using a phage display library. Three of these antibodies, referred to herein as 16E2, 24C4 and 20E6, have been sequenced and characterized. The respective DNA and amino acid sequences and complementarity determining regions of these antibodies are shown in FIGS. 15A-15C and 16. In one embodiment of the invention, scFv Apo-2 antibodies will have the same biological characteristics as the 16E2, 24C4 or 20E6 antibodies identified herein. The term "biological characteristics" is used to refer to the in vitro and/or in vivo activities or properties of the scFv antibody, such as the ability to specifically bind to Apo-2 or to substantially induce or enhance Apo-2 activation. As disclosed in the present specification, the 16E2, 24C4 and 20E6 antibodies are characterized as binding to Apo-2, having agonistic activity for inducing apoptosis, and having no cross-reactivity to DR4 or several of the other known molecules recognized by the Apo-2 ligand. Optionally, the scFv Apo-2 antibody will bind to the same epitope or epitopes recognized by the 16E2, 24C4 or 20E6 antibodies disclosed herein. This can be determined by conducting various assays, such as described herein and in the Examples. For instance, to determine whether a scFv antibody has the same specificity as the 16E2, 24C4 or 20E6 antibodies specifically disclosed, one can compare activity in apoptosis induction assays, such as those described in the Examples below.

Optionally the scFv antibodies to Apo-2 may include antibodies which contain a VH and VL chain that include one or more complementarity determining region (CDR) amino acid sequences identified in FIG. 16 for the 16E2, 20E6, or 24C4 antibodies.

4. Bispecific Antibodies

Bispecific antibodies are monoclonal, preferably human or humanized, antibodies that have binding specificities for at least two different antigens. In the present case, one of the binding specificities is for the Apo-2, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy-chain/light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published 3 Mar. 1994. For further details of generating bispecific antibodies see, for example, Suresh et al., *Methods in Enzymology,* 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Triabodies

Triabodies are also within the scope of the invention. Such antibodies are described for instance in Iliades et al., *FEBS Letters,* 409:437-441 (1997) and Korrt et al., Protein Engineering, 10:423-433 (1997).

7. Other Modifications

Other modifications of the Apo-2 antibodies are contemplated. For example, it may be desirable to modify the antibodies of the invention with respect to effector function, so as to enhance the therapeutic effectiveness of the antibodies. For instance, cysteine residue(s) may be introduced into the Fc region, thereby allowing interchain disulfide bond formation in this region. The homodimeric antibody thus generated may have improved internalization capability and/or increased complement-mediated cell killing [see, e.g., Caron et al., *J. Exp. Med.,* 176:1191-1195 (1992); Shopes, *J. Immunol.,* 148: 2918-2922 (1992). Homodimeric antibodies may also be prepared using heterobifunctional cross-linkers as described in Wolff et al., *Cancer Research,* 53:2560-2565 (1993). Ghetie et al., *Proc. Natl. Acad. Sci.,* 94:7509-7514 (1997), further describe preparation of IgG-IgG homodimers and disclose that such homodimers can enhance apoptotic activity as compared to the monomers. Alternatively, the antibodies can be engineered to have dual Fc regions [see, Stevenson et al., *Anti-Cancer Drug Design,* 3:219-230 (1989)].

It may be desirable to modify the amino acid sequences of the antibodies disclosed herein. Sequences within the scFv complementary determining or linker regions (as shown in FIG. 16) may be modified for instance to modulate the biological activities of these antibodies. Variations in the full-length scFv sequence or in various domains of the scFv molecules described herein, can be made, for example, using any of the techniques and guidelines for conservative and non-conservative mutations set forth, for instance, in U.S. Pat. No. 5,364,934. Variations may be a substitution, deletion or insertion of one or more codons encoding a scFv that results in a change in the amino acid sequence of the scFv as compared with the native sequence scFv. Optionally, the variation is by substitution of at least one amino acid with any other amino acid in one or more of the domains of the scFv molecule. The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the scFv variant DNA.

The antibodies may optionally be covalently attached or conjugated to one or more chemical groups. A polyol, for example, can be conjugated to an antibody molecule at one or more amino acid residues, including lysine residues as disclosed in WO 93/00109. Optionally, the polyol is a poly (alkelene glycol), such as poly(ethylene glycol) (PEG), however, those skilled in the art recognize that other polyols, such as, for example, poly(propylene glycol) and polyethylene-polypropylene glycol copolymers, can be employed using techniques for conjugating PEG to polypeptides. A variety of methods for pegylating polypeptides have been described.

See, e.g. U.S. Pat. No. 4,179,337 which discloses the conjugation of a number of hormones and enzymes to PEG and polypropylene glycol to produce physiologically active compositions having reduced immunogenicities.

The antibodies may also be fused or linked to another heterologous polypeptide or amino acid sequence such as an epitope tag. Epitope tag polypeptides and methods of their use are described above in Section A, paragraph 8. Any of the tags described herein may be linked to the antibodies. The Examples below, for instance, describe His-tagged and gD-tagged single-chain antibodies.

D. Therapeutic Uses for Apo-2 Antibodies

The Apo-2 antibodies of the invention have therapeutic utility. Agonistic Apo-2 antibodies, for instance, may be employed to activate or stimulate apoptosis in cancer cells. Accordingly, the invention provides methods for treating cancer using such Apo-2 antibodies. It is of course contemplated that the methods of the invention can be employed in combination with still other therapeutic techniques such as surgery.

The agonist is preferably administered to the mammal in a carrier. Suitable carriers and their formulations are described in *Remington's Pharmaceutical Sciences,* 16th ed., 1980, Mack Publishing Co., edited by Oslo et al. Typically, an appropriate amount of a pharmaceutically-acceptable salt is used in the formulation to render the formulation isotonic. Examples of a pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the agonist, which matrices are in the form of shaped articles, e.g., films, liposomes or microparticles. It will be apparent to those persons skilled in the art that certain carriers may be more preferable depending upon, for instance, the route of administration and concentration of agonist being administered.

The agonist antibody can be administered to the mammal by injection (e.g., intravenous, intraperitoneal, subcutaneous, intramuscular), or by other methods such as infusion that ensure its delivery to the bloodstream in an effective form. The agonist may also be administered by intratumoral, peritumoral, intralesional, or perilesional routes, to exert local as well as systemic therapeutic effects. Local or intravenous injection is preferred.

Effective dosages and schedules for administering the agonist antibody may be determined empirically, and making such determinations is within the skill in the art. Those skilled in the art will understand that the dosage of agonist that must be administered will vary depending on, for example, the mammal which will receive the agonist, the route of administration, the particular type of agonist used and other drugs being administered to the mammal. Guidance in selecting appropriate doses for antibody agonists is found in the literature on therapeutic uses of antibodies, e.g., *Handbook of Monoclonal Antibodies,* Ferrone et al., eds., Noges Publications, Park Ridge, N.J., (1985) ch. 22 and pp. 303-357; Smith et al., *Antibodies in Human Diagnosis and Therapy,* Haber et al., eds., Raven Press, New York (1977) pp. 365-389. A typical daily dosage of the agonist used alone might range from about 1 µg/kg to up to 100 mg/kg of body weight or more per day, depending on the factors mentioned above.

The agonist antibody may also be administered to the mammal in combination with effective amounts of one or more other therapeutic agents or in conjunction with radiation treatment. Therapeutic agents contemplated include chemotherapeutics as well as immunoadjuvants and cytokines. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. The agonist may be administered sequentially or concurrently with the one or more other therapeutic agents. The amounts of agonist and therapeutic agent depend, for example, on what type of drugs are used, the cancer being treated, and the scheduling and routes of administration but would generally be less than if each were used individually.

Following administration of agonist to the mammal, the mammal's cancer and physiological condition can be monitored in various ways well known to the skilled practitioner. For instance, tumor mass may be observed physically or by standard x-ray imaging techniques.

The Apo-2 antibodies of the invention may also be useful in enhancing immune-mediated cell death in cells expressing Apo-2, for instance, through complement fixation or ADCC. Alternatively, antagonistic antibodies may be used to block excessive apoptosis (for instance in neurodegenerative disease) or to block potential autoimmune/inflammatory effects of Apo-2 resulting from NF-κB activation. Such antagonistic antibodies can be utilized according to the therapeutic methods and techniques described above.

E. Non-therapeutic Uses for Apo-2 Antibodies

Apo-2 antibodies may further be used in diagnostic assays for Apo-2, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques,* CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Apo-2 antibodies also are useful for the affinity purification of Apo-2 from recombinant cell culture or natural sources. In this process, the antibodies against Apo-2 are immobilized on a suitable support, such as Sephadex resin or filter paper, using methods well known in the art. The immobilized antibody then is contacted with a sample containing the Apo-2 to be purified, and thereafter the support is washed with a suitable solvent that will remove substantially all the material in the sample except the Apo-2, which is bound to the immobilized antibody. Finally, the support is washed with another suitable solvent that will release the Apo-2 from the antibody.

F. Kits Containing Apo-2 or Apo-2 Antibodies

In a further embodiment of the invention, there are provided articles of manufacture and kits containing Apo-2 or Apo-2 antibodies which can be used, for instance, for the therapeutic or non-therapeutic applications described above. The article of manufacture comprises a container with a label. Suitable containers include, for example, bottles, vials, and test tubes. The containers may be formed from a variety of materials such as glass or plastic. The container holds a composition which includes an active agent that is effective for therapeutic or non-therapeutic applications, such as described above. The active agent in the composition is Apo-2 or an Apo-2 antibody. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLES

All restriction enzymes referred to in the examples were purchased from New England Biolabs and used according to manufacturer's instructions. All other commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding Human Apo-2

Expressed sequence tag (EST) DNA databases (LIFESEQ™, Incyte Pharmaceuticals, Palo Alto, Calif.) were searched and an EST was identified which showed homology to the death domain of the Apo-3 receptor [Marsters et al., *Curr. Biol.*, 6:750 (1996)]. Human pancreas and kidney lgt10 bacteriophage cDNA libraries (both purchased from Clontech) were ligated into pRK5 vectors as follows. Reagents were added together and incubated at 16° C. for 16 hours: 5×T4 ligase buffer (3 ml); pRK5, XhoI, NotI digested vector, 0.5 mg, 1 ml); cDNA (5 ml) and distilled water (6 ml). Subsequently, additional distilled water (70 ml) and 10 mg/ml tRNA (0.1 ml) were added and the entire reaction was extracted through phenol:chloroform:isoamyl alcohol (25:24:1). The aqueous phase was removed, collected and diluted into 5M NaCl (10 ml) and absolute ethanol (−20° C., 250 ml). This was then centrifuged for 20 minutes at 14,000×g, decanted, and the pellet resuspended into 70% ethanol (0.5 ml) and centrifuged again for 2 minutes at 14,000×g. The DNA pellet was then dried in a speedvac and eluted into distilled water (3 ml) for use in the subsequent procedure.

The ligated cDNA/pRK5 vector DNA prepared previously was chilled on ice to which was added electrocompetent DH10B bacteria (Life Tech., 20 ml). The bacteria vector mixture was then electroporated as per the manufacturers recommendation. Subsequently SOC media (1 ml) was added and the mixture was incubated at 37° C. for 30 minutes. The transformants were then plated onto 20 standard 150 mm LB plates containing ampicillin and incubated for 16 hours (37° C.) to allow the colonies to grow. Positive colonies were then scraped off and the DNA isolated from the bacterial pellet using standard CsCl-gradient protocols.

An enriched 5'-cDNA library was then constructed to obtain a bias of cDNA fragments which preferentially represents the 5' ends of cDNA's contained within the library. 10 mg of the pooled isolated full-length library plasmid DNA (41 ml) was combined with Not 1 restriction buffer (New England Biolabs, 5 ml) and Not 1 (New England Biolabs, 4 ml) and incubated at 37° C. for one hour. The reaction was extracted through phenol:chloroform:isoamyl alcohol (25:24:1, 50 ml), the aqueous phase removed, collected and resuspended into 5M NaCl (5 ml) and absolute ethanol (−20° C., 150 ml). This was then centrifuged for 20 minutes at 14,000× g, decanted, resuspended into 70% ethanol (0.5 ml) and centrifuged again for 2 minutes at 14,000×g. The supernatant was then removed, the pellet dried in a speedvac and resuspended in distilled water (10 ml).

The following reagents were brought together and incubated at 37° C. for 2 hours: distilled water (3 ml); linearized DNA library (1 mg, 1 ml); Ribonucleotide mix (Invitrogen, 10 ml); transcription buffer (Invitrogen, 2 ml) and Sp6 enzyme mix. The reaction was then extracted through phenol:chloroform:isoamyl alcohol (25:24:1, 50 ml) and the aqueous phase was removed, collected and resuspended into 5M NaCl (5 ml) and absolute ethanol (−20° C., 150 ml) and centrifuged for 20 minutes at 14,000×g. The pellet was then decanted and resuspended in 70% ethanol (0.5 ml), centrifuged again for 2 minutes at 14,000×g, decanted, dried in a speedvac and resuspended into distilled water (10 ml).

The following reagents were added together and incubated at 16° C. for 16 hours: 5×T4 ligase buffer (Life Tech., 3 ml); pRK5 Cla-Sal digested vector, 0.5 mg, 1 ml); cDNA (5 ml); distilled water (6 ml). Subsequently, additional distilled water (70 ml) and 10 mg/ml tRNA (0.1 ml) was added and the entire reaction was extracted through phenol:chloroform:isoamyl alcohol (25:24:1, 100 ml). The aqueous phase was removed, collected and diluted by 5M NaCl (10 ml) and absolute ethanol (−20° C., 250 ml) and centrifuged for 20 minutes at 14,000×g. The DNA pellet was decanted, resuspended into 70% ethanol (0.5 ml) and centrifuged again for 2 minutes at 14,000×g. The supernatant was removed and the residue pellet was dried in a speedvac and resuspended in distilled water (3 ml). The ligated cDNA/pSST-amy.1 vector DNA was chilled on ice to which was added electrocompetent DH10B bacteria (Life Tech., 20 ml). The bacteria vector mixture was then electroporated as recommended by the manufacturer. Subsequently, SOC media (Life Tech., 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient.

The cDNA libraries were screened by hybridization with a synthetic oligonucleotide probe:

GGGAGCCGCTCATGAGGAAGTTGGGCCT-CATGGACAATGAGATAAAGGTG-GCTAAAGCTGAGGCAGCGGG (SEQ ID NO:3) based on the EST.

Three cDNA clones were sequenced in entirety. The overlapping coding regions of the cDNAs were identical except for codon 410 (using the numbering system for FIG. 1); this position encoded a leucine residue (TTG) in both pancreatic cDNAs, and a methionine residue (ATG) in the kidney cDNA, possibly due to polymorphism.

The entire nucleotide sequence of Apo-2 is shown in FIG. 1 (SEQ ID NO:2). Clone 27868 (also referred to as pRK5-Apo-2 deposited as ATCC 209021, as indicated below) contains a single open reading frame with an apparent translational initiation site at nucleotide positions 140-142 [Kozak et al., supra]) and ending at the stop codon found at nucleotide positions 1373-1375 (FIG. 1; SEQ ID NO:2). The predicted polypeptide precursor is 411 amino acids long, a type I transmembrane protein, and has a calculated molecular weight of approximately 45 kDa. Hydropathy analysis (not shown) suggested the presence of a signal sequence (residues 1-53), followed by an extracellular domain (residues 54-182), a transmembrane domain (residues 183-208), and an intracellular domain (residues 209-411) (FIG. 2A; SEQ ID NO:1). N-terminal amino acid sequence analysis of Apo-2-IgG expressed in 293 cells showed that the mature polypeptide starts at amino acid residue 54, indicating that the actual signal sequence comprises residues 1-53. Apo-2 polypeptide is obtained or obtainable by expressing the molecule encoded by the cDNA insert of the deposited ATCC 209021 vector.

TNF receptor family proteins are typically characterized by the presence of multiple (usually four) cysteine-rich domains in their extracellular regions—each cysteine-rich domain being approximately 45 amino acids long and containing approximately 6, regularly spaced, cysteine residues. Based on the crystal structure of the type 1 TNF receptor, the cysteines in each domain typically form three disulfide bonds in which usually cysteines 1 and 2, 3 and 5, and 4 and 6 are paired together. Like DR4, Apo-2 contains two extracellular cysteine-rich pseudorepeats (FIG. 2A), whereas other identified mammalian TNFR family members contain three or more such domains [Smith et al., *Cell*, 76:959 (1994)].

The cytoplasmic region of Apo-2 contains a death domain (amino acid residues 324-391 shown in FIG. 1; see also FIG. 2A) which shows significantly more amino acid sequence identity to the death domain of DR4 (64%) than to the death domain of TNFR1 (30%); CD95 (19%); or Apo-3/DR3 (29%) (FIG. 2B). Four out of six death domain amino acids that are required for signaling by TNFR1 [Tartaglia et al., supra] are conserved in Apo-2 while the other two residues are semi-conserved (see FIG. 2B).

Based on an alignment analysis (using the ALIGN™ computer program) of the full-length sequence, Apo-2 shows more sequence identity to DR4 (55%) than to other apoptosis-linked receptors, such as TNFR1 (19%); CD95 (17%); or Apo-3 (also referred to as DR3, WSL-1 or TRAMP) (29%).

Example 2

A. Expression of Apo-2 ECD

A soluble extracellular domain (ECD) fusion construct was prepared. An Apo-2 ECD (amino acid residues 1-184 shown in FIG. 1) was obtained by PCR and fused to a C-terminal Flag epitope tag (Sigma). (The Apo-2 ECD construct included residues 183 and 184 shown in FIG. 1 to provide flexibility at the junction, even though residues 183 and 184 are predicted to be in the transmembrane region). The Flag epitope-tagged molecule was then inserted into pRK5, and expressed by transient transfection into human 293 cells (ATCC CRL 1573).

After a 48 hour incubation, the cell supernatants were collected and either used directly for co-precipitation studies (see Example 3) or subjected to purification of the Apo-2 ECD-Flag by affinity chromatography on anti-Flag agarose beads, according to manufacturer's instructions (Sigma).

B. Expression of Apo-2 ECD as an Immunoadhesin

A soluble Apo-2 ECD immunoadhesin construct was prepared. The Apo-2 ECD (amino acids 1-184 shown in FIG. 1) was fused to the hinge and Fc region of human immunoglobulin G$_1$ heavy chain in pRK5 as described previously [Ashkenazi et al., *Proc. Natl. Acad. Sci.*, 88:10535-10539 (1991)]. The immunoadhesin was expressed by transient transfection into human 293 cells and purified from cell supernatants by protein A affinity chromatography, as described by Ashkenazi et al., supra.

Example 3

Immunoprecipitation Assay Showing Binding Interaction Between Apo-2 and Apo-2 Ligand To determine whether Apo-2 and Apo-2L interact or associate with each other, supernatants from mock-transfected 293 cells or from 293 cells transfected with Apo-2 ECD-Flag (described in Example 2 above) (5 ml) were incubated with 5 µg poly-histidine-tagged soluble Apo-2L [Pitti et al., supra] for 30 minutes at room temperature and then analyzed for complex formation by a co-precipitation assay.

The samples were subjected to immunoprecipitation using 25 µl anti-Flag conjugated agarose beads (Sigma) or Nickel-conjugated agarose beads (Qiagen). After a 1.5 hour incubation at 4° C., the beads were spun down and washed four times in phosphate buffered saline (PBS). By using anti-Flag agarose, the Apo-2L was precipitated through the Flag-tagged Apo-2 ECD; by using Nickel-agarose, the Apo-2 ECD was precipitated through the His-tagged Apo-2L. The precipitated proteins were released by boiling the beads for 5 minutes in SDS-PAGE buffer, resolved by electrophoresis on 12% polyacrylamide gels, and then detected by immunoblot with anti-Apo-2L or anti-Flag antibody (2 µg/ml) as described in Marsters et al., *J. Biol. Chem.*, (1997).

The results, shown in FIG. 3, indicate that the Apo-2 ECD and Apo-2L can associate with each other.

The binding interaction was further analyzed by purifying Apo-2 ECD from the transfected 293 cell supernatants with anti-Flag beads (see Example 2) and then analyzing the samples on a BIACORE™ instrument. The BIACORE™ analysis indicated a dissociation constant ($K_d$) of about 1 nM. BIACORE™ analysis also showed that the Apo-2 ECD is not capable of binding other apoptosis-inducing TNF family members, namely, TNF-alpha (Genentech, Inc., Pennica et al., *Nature*, 312:712 (1984), lymphotoxin-alpha (Genentech, Inc.), or Fas/Apo-1 ligand (Alexis Biochemicals). The data thus shows that Apo-2 is a specific receptor for Apo-2L.

Example 4

Induction of Apoptosis by Apo-2

Because death domains can function as oligomerization interfaces, over-expression of receptors that contain death domains may lead to activation of signaling in the absence of ligand [Frazer et al., supra, Nagata et al., supra]. To determine whether Apo-2 was capable of inducing cell death, human 293 cells or HeLa cells (ATCC CCL 2.2) were transiently transfected by calcium phosphate precipitation (293 cells) or electroporation (HeLa cells) with a pRK5 vector or pRK5-based plasmids encoding Apo-2 and/or CrmA. When applicable, the total amount of plasmid DNA was adjusted by adding vector DNA. Apoptosis was assessed 24 hours after transfection by morphology (FIG. 4A); DNA fragmentation (FIG. 4B); or by FACS analysis of phosphatydilserine exposure (FIG. 4C) as described in Marsters et al., *Curr. Biol.*, 6:1669 (1996). As shown in FIGS. 4A and 4B, the Apo-2 transfected 293 cells underwent marked apoptosis.

For samples assayed by FACS, the HeLa cells were co-transfected with pRK5-CD4 as a marker for transfection and apoptosis was determined in CD4-expressing cells; FADD was co-transfected with the Apo-2 plasmid; the data are means±SEM of at least three experiments, as described in Marsters et al., *Curr. Biol.*, 6:1669 (1996). The caspase inhibitors, DEVD-fmk (Enzyme Systems) or z-VAD-fmk (Research Biochemicals Intl.) were added at 200 μM at the time of transfection. As shown in FIG. 4C, the caspase inhibitors CrmA, DEVD-fmk, and z-VAD-fmk blocked apoptosis induction by Apo-2, indicating the involvement of Ced-3-like proteases in this response.

FADD is an adaptor protein that mediates apoptosis activation by CD95, TNFR1, and Apo-3/DR3 [Nagata et al., supra], but does not appear necessary for apoptosis induction by Apo-2L [Marsters et al., supra] or by DR4 [Pan et al., supra]. A dominant-negative mutant form of FADD, which blocks apoptosis induction by CD95, TNFR1, or Apo-3/DR3 [Frazer et al., supra; Nagata et al., supra; Chinnayian et al., supra] did not inhibit apoptosis induction by Apo-2 when co-transfected into HeLa cells with Apo-2 (FIG. 4C). These results suggest that Apo-2 signals apoptosis independently of FADD. Consistent with this conclusion, a glutathione-S-transferase fusion protein containing the Apo-2 cytoplasmic region did not bind to in vitro transcribed and translated FADD (data not shown).

Example 5

Inhibition of Apo-2L Activity by Soluble Apo-2 ECD

Soluble Apo-2L (0.5 μg/ml, prepared as described in Pitti et al., supra) was pre-incubated for 1 hour at room temperature with PBS buffer or affinity-purified Apo-2 ECD (5 μg/ml) together with anti-Flag antibody (Sigma) (1 μg/ml) and added to HeLa cells. After a 5 hour incubation, the cells were analyzed for apoptosis by FACS (as above) (FIG. 4D).

Apo-2L induced marked apoptosis in HeLa cells, and the soluble Apo-2 ECD was capable of blocking Apo-2L action (FIG. 4D), confirming a specific interaction between Apo-2L and Apo-2. Similar results were obtained with the Apo-2 ECD immunoadhesin (FIG. 4D). Dose-response analysis showed half-maximal inhibition at approximately 0.3 nM Apo-2 immunoadhesin (FIG. 4E).

Example 6

Activation of NF-κB by Apo-2

An assay was conducted to determine whether Apo-2 activates NF-κB.

HeLa cells were transfected with pRK5 expression plasmids encoding full-length native sequence Apo-2, DR4 or Apo-3 and harvested 24 hours after transfection. Nuclear extracts were prepared and 1 μg of nuclear protein was reacted with a $^{32}$P-labelled NF-κB-specific synthetic oligonucleotide probe ATCAGGGACTTTCCGCTGGG-GACTTTCCG (SEQ ID NO:4) [see, also, MacKay et al., *J. Immunol.*, 153:5274-5284 (1994)], alone or together with a 50-fold excess of unlabelled probe, or with an irrelevant $^{32}$P-labelled synthetic oligonucleotide AGGATGGGAAGTGT-GTGATATATCCTTGAT (SEQ ID NO:5). In some samples, antibody to p65/RelA subunits of NF-κB (1 μg/ml; Santa Cruz Biotechnology) was added. DNA binding was analyzed by an electrophoretic mobility shift assay as described by Hsu et al., supra; Marsters et al., supra, and MacKay et al., supra.

The results are shown in FIG. 5. As shown in FIG. 5A, upon transfection into HeLa cells, both Apo-2 and DR4 induced significant NF-κB activation as measured by the electrophoretic mobility shift assay; the level of activation was comparable to activation observed for Apo-3/DR3. Antibody to the p65/RelA subunit of NF-κB inhibited the mobility of the NF-κB probe, implicating p65 in the response to all 3 receptors.

An assay was also conducted to determine if Apo-2L itself can regulate NF-κB activity. HeLa cells or MCF7 cells (human breast adenocarcinoma cell line, ATCC HTB 22) were treated with PBS buffer, soluble Apo-2L (Pitti et al., supra) or TNF-alpha (Genentech, Inc., see Pennica et al., *Nature*, 312: 721 (1984)) (1 μg/ml) and assayed for NF-κB activity as above. The results are shown in FIG. 5B. The Apo-2L induced a significant NF-κB activation in the treated HeLa cells but not in the treated MCF7 cells; the TNF-alpha induced a more pronounced activation in both cell lines. Several studies have disclosed that NF-κB activation by TNF can protect cells against TNF-induced apoptosis [Nagata, supra].

The effects of a NF-κB inhibitor, ALLN (N-acetyl-Leu-Leu-norleucinal) and a transcription inhibitor, cyclohexamide, were also tested. The HeLa cells (plated in 6-well dishes) were preincubated with PBS buffer, ALLN (Calbiochem) (40 μg/ml) or cyclohexamide (Sigma) (50 μg/ml) for 1 hour before addition of Apo-2L (1 μg/ml). After a 5 hour incubation, apoptosis was analyzed by FACS (see FIG. 5C).

The results are shown in FIG. 5C. Both ALLN and cyclohexamide increased the level of Apo-2L-induced apoptosis in the HeLa cells. The data indicates that Apo-2L can induce protective NF-κB-dependent genes. The data also indicates that Apo-2L is capable of activating NF-κB in certain cell lines and that both Apo-2 and DR4 may mediate that function.

Example 7

Expression of Apo-2 in Mammalian Tissues

A. Northern Blot Analysis

Expression of Apo-2 mRNA in human tissues was examined by Northern blot analysis. Human RNA blots were hybridized to a 4.6 kilobase $^{32}$P-labelled DNA probe based on the full length Apo-2 cDNA; the probe was generated by digesting the pRK5-Apo-2 plasmid with EcoRI. Human fetal RNA blot MTN (Clontech), human adult RNA blot MTN-II (Clontech), and human cancer cell line RNA blot (Clontech) were incubated with the DNA probes. Blots were incubated with the probes in hybridization buffer (5×SSPE; 2×Denhardt's solution; 100 mg/mL denatured sheared salmon sperm DNA; 50% formamide; 2% SDS) for 60 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure.

As shown in FIG. 6A, a predominant mRNA transcript of approximately 4.6 kb was detected in multiple tissues. Expression was relatively high in fetal and adult liver and lung, and in adult ovary and peripheral blood leukocytes (PBL), while no mRNA expression was detected in fetal and adult brain. Intermediate levels of expression were seen in adult colon, small intestine, testis, prostate, thymus, pancreas, kidney, skeletal muscle, placenta, and heart. Several adult tissues that express Apo-2, e.g., PBL, ovary, and spleen, have been shown previously to express DR4 [Pan et al., supra], however, the relative levels of expression of each receptor mRNA appear to be different.

As shown in FIG. 6B, Apo-2 mRNA was expressed relatively high in 6 of 8 human cancer cell lines examined, namely, HL60 promyelocytic leukemia, HeLa S3 cervical carcinoma, K562 chronic myelogenous leukemia, SW 480 colorectal adenocarcinoma, A549 lung carcinoma, and G361 melanoma. There was also detectable expression in Burkitt's lymphoma (Raji) cells. Thus, Apo-2 may be useful as a target for inducing apoptosis in cancer cells from lymphoid as well as non-lymphoid tumors.

B. In Situ Hybridization

Expression of Apo-2 in normal and in cancerous human tissues was examined by in situ hybridization. In addition, several different chimp and rhesus monkey tissues were examined for Apo-2 expression. These tissues included: human fetal tissues (E12-E16 weeks)—placenta, umbilical cord, liver, kidney, adrenal gland, thyroid, lung, heart, great vessels, esophagus, stomach, small intestine, spleen, thymus, pancreas, brain, eye, spinal cord, body wall, pelvis and lower limb; adult human tissues—kidney, bladder, adrenal gland, spleen, lymph node, pancreas, lung, skin, retina, liver; chimp tissues—salivary gland, stomach, thyroid, parathyroid, tongue, thymus, ovary, lymph node, and peripheral nerve; rhesus monkey tissues—cerebral cortex, hippocampus, cerebellum and penis; human tumor tissue—lung adenocarcinoma, testis, lung carcinoma, breast carcinoma, fibroadenoma, soft tissue sarcoma.

Tissue samples were paraffin-embedded and sectioned. Later, the sectioned tissues were deparaffinized and the slides placed in water. The slides were rinsed twice for five minutes at room temperature in 2×SSC. After rinsing, the slides were placed in 20 µg/ml proteinase K (in Rnase-free buffer) for 15 minutes at 37° C. (for fetal tissues) or 8× proteinase K for 30 minutes at 37° C. (for formalin tissues). The slides were then rinsed again in 0.5×SSC and dehydrated. Prior to hybridization, the slides were placed in a plastic box lined with buffer (4×SSC, 50% formamide)-saturated filter paper. The tissues were covered with 50 µl hybridization buffer (3.75 g Dextran sulfate plus 6 ml water; vortexed and heated for 2 minutes; cooled on ice and 18.75 ml formamide, 3.75 ml 20×SSC and 9 ml water added) and incubated at 42° C. for 1 to 4 hours.

Hybridization was conducted using a $^{33}$P-labelled probe consisting of nucleotides 706-1259 of SEQ ID NO:2. The probe was added to the slides in hybridization buffer and incubated overnight at 55° C. Multiple washing steps were then performed sequentially as follows: twice for 10 minutes at room temperature in 2×SSC, EDTA buffer (400 ml 20×SSC, 16 ml 0.25M EDTA); once for 30 minutes at 37° C. in 20 µg/ml RNase A; twice for 10 minutes at room temperature in 2×SSC, EDTA buffer; once for 2 hours at 55° C. in 0.1×SSC, EDTA buffer; twice for 10 minutes at room temperature in 0.5×SSC. Dehydration was performed for 2 minutes each in 50%, 70%, 90% EtOH containing 0.3 M NH$_4$AC. Finally, the slides were air-dried for 2 hours and exposed to film.

Expression of Apo-2 in the fetal tissues appeared strongest over hepatocytes in liver, developing glomeruli in kidney, adrenal cortex, and epithelium of gastrointestinal tract. Moderate expression was observed over epithelial cells in lung and at sites of vascularization of a bone growth plate. A relatively low level expression was observed over thyroid epithelial cells and cells in cardiac ventricles. Expression was observed over lymphoid cells in the thymic medulla, developing lymph glands and placenta cytotrophoblast cells.

Expression of Apo-2 in adult tissues was observed over resting oocytes in primordial follicles and low levels over granulosa cells of developing follicles in chimp ovary. Expression was observed in cirrhotic livers over hepatocytes at the edge of nodules (i.e., area of damage, normal adult liver was negative). Other tissues were negative for expression.

In the cancer tissues examined, Apo-2 expression was found in two lung adenocarcinomas and two germ cell tumors of the testis. Two additional lung carcinomas (one squamous) were negative. One of five breast carcinomas was positive (there was expression in normal breast tissue). In a fibroadenoma, there appeared to be expression over both epithelial and stromal elements. A soft tissue sarcoma was also positive. Other tissues examined were negative.

Example 8

Chromosomal Localization of the Apo-2 Gene

Chromosomal localization of the human Apo-2 gene was examined by radiation hybrid (RH) panel analysis. RH mapping was performed by PCR using a human-mouse cell radiation hybrid panel (Research Genetics) and primers based on the coding region of the Apo-2 cDNA [Gelb et al., *Hum. Genet.*, 98:141 (1996)]. Analysis of the PCR data using the Stanford Human Genome Center Database indicates that Apo-2 is linked to the marker D8S481, with an LOD of 11.05; D8S481 is linked in turn to D8S2055, which maps to human chromosome 8p21. A similar analysis of DR4 showed that DR4 is linked to the marker D8S2127 (with an LOD of 13.00), which maps also to human chromosome 8p21.

To Applicants' present knowledge, to date, no other member of the TNFR gene family has been located to chromosome 8.

Example 9

Preparation of Monoclonal Antibodies Specific for Apo-2

Balb/c mice (obtained from Charles River Laboratories) were immunized by injecting 0.5 µg/50 µl of an Apo-2 ECD immunoadhesin protein (diluted in MPL-TDM adjuvant purchased from Ribi Immunochemical Research Inc., Hamilton, Mont.) 11 times into each hind foot pad at 3-4 day intervals. The Apo-2 ECD immunoadhesin protein was generated by fusing an extracellular domain sequence of Apo-2 (amino acids 1-184 shown in FIG. 1) to the hinge and Fc region of human immunoglobulin $G_1$ heavy chain in pRK5 as described previously [Ashkenazi et al., *Proc. Natl. Acad. Sci.*, 88:10535-10539 (1991)]. The immunoadhesin protein was expressed by transient transfection into human 293 cells and purified from cell supernatants by protein A affinity chromatography, as described by Ashkenazi et al., supra (See also Example 2B above).

Three days after the final boost, popliteal lymph nodes were removed from the mice and a single cell suspension was prepared in DMEM media (obtained from Biowhitakker Corp.) supplemented with 1% penicillin-streptomycin. The lymph node cells were then fused with murine myeloma cells P3X63AgU.1 (ATCC CRL 1597) using 35% polyethylene glycol and cultured in 96-well culture plates. Hybridomas resulting from the fusion were selected in HAT medium. Ten days after the fusion, hybridoma culture supernatants were screened in an ELISA to test for the presence of monoclonal antibodies binding to the Apo-2 ECD immunoadhesin protein.

In the ELISA, 96-well microtiter plates (Maxisorb; Nunc, Kamstrup, Denmark) were coated by adding 50 µl of 2 µg/ml goat anti-human IgG Fc (purchased from Cappel Laboratories) in PBS to each well and incubating at 4° C. overnight. The plates were then washed three times with wash buffer (PBS containing 0.05% Tween 20). The wells in the microtiter plates were then blocked with 50 µl of 2.0% bovine serum albumin in PBS and incubated at room temperature for 1 hour. The plates were then washed again three times with wash buffer.

After the washing step, 50 µl of 0.4 µg/ml Apo-2 ECD immunoadhesin protein (as described above) in assay buffer was added to each well. The plates were incubated for 1 hour at room temperature on a shaker apparatus, followed by washing three times with wash buffer.

Following the wash steps, 100 µl of the hybridoma supernatants or purified antibody (using Protein A-sepharose columns) (1 µg/ml) was added to designated wells in the presence of CD4-IgG. 100 µl of P3X63AgU.1 myeloma cell conditioned medium was added to other designated wells as controls. The plates were incubated at room temperature for 1 hour on a shaker apparatus and then washed three times with wash buffer.

Next, 50 µl HRP-conjugated goat anti-mouse IgG Fc (purchased from Cappel Laboratories), diluted 1:1000 in assay buffer (0.5% bovine serum albumin, 0.05% Tween-20, 0.01% Thimersol in PBS), was added to each well and the plates incubated for 1 hour at room temperature on a shaker apparatus. The plates were washed three times with wash buffer, followed by addition of 50 µl of substrate (TMB microwell peroxidase substrate, Kirkegaard & Perry, Gaithersburg, Md.) to each well and incubation at room temperature for 10 minutes. The reaction was stopped by adding 50 µl of TMB 1-component stop solution (diethyl glycol, Kirkegaard & Perry) to each well, and absorbance at 450 nm was read in an automated microtiter plate reader.

Of the hybridoma supernatants screened in the ELISA, 22 supernatants tested positive (calculated as approximately 4 times above background). The supernatants testing positive in the ELISA were further analyzed by FACS analysis using 9D cells (a human B lymphoid cell line expressing Apo-2; Genentech, Inc.) and FITC-conjugated goat anti-mouse IgG. For this analysis, 25 µl of cells suspended (at $4 \times 10^6$ cells/ml) in cell sorter buffer (PBS containing 1% FCS and 0.02% $NaN_3$) were added to U-bottom microtiter wells, mixed with 100 µl of culture supernatant or purified antibody (purified on Protein A-sepharose columns) (10 µg/ml) in cell sorter buffer, and incubated for 30 minutes on ice. The cells were then washed and incubated with 100 µl FITC-conjugated goat anti-mouse IgG for 30 minutes at 4° C. Cells were then washed twice, resuspended in 150 µl of cell sorter buffer and then analyzed by FACScan (Becton Dickinson, Mountain View, Calif.). FACS analysis showed 8/22 supernatants were positive for anti-Apo-2 antibodies.

FIG. 7 shows the FACS staining of 9D cells incubated with one of the Apo-2 antibodies, referred to as 3F11.39.7. As shown in FIG. 7, the 3F11.39.7 antibody recognizes the Apo-2 receptor expressed in 9D cells.

Example 10

Assay for Ability of Apo-2 Abs to Agonistically Induce Apoptosis

Hybridoma supernatants and purified antibodies (as described in Example 9 above) were tested for activity to induce Apo-2 mediated 9D cell apoptosis. The 9D cells ($5 \times 10^5$ cells/0.1 ml) were incubated with varying concentrations of antibodies in 100 µl complete RPMI media at 4° C. for 15 minutes. The cells were then incubated for 5 minutes at 37° C. and 10 µg of goat anti-mouse IgG Fc antibody (Cappel Laboratories) in 300 µl of complete RPMI was added to some of the cell samples. At this point, the cells were incubated overnight at 37° C. and in the presence of 7% $CO_2$. The cells were then harvested and washed once with PBS. The viability of the cells was determined by staining of FITC-annexin V binding to phosphatidylserine according to manufacturer recommendations (Clontech). The cells were washed in PBS and resuspended in 200 µl binding buffer. Ten µl of annexin-V-FITC (1 µg/ml) and 10 µl of propidium iodide were added to the cells. After incubation for 15 minutes in the dark, the 9D cells were analyzed by FACS.

As shown in FIG. 8, the 3F11.39.7 antibody (in the absence of the goat anti-mouse IgG Fc) induced apoptosis in the 9D cells as compared to the control antibodies. Agonistic activity, however, was enhanced by Apo-2 receptor cross-linking in the presence of the goat anti-mouse IgG Fc (see FIG. 9). This enhanced apoptosis (FIG. 9) by the combination of antibodies is comparable to the apoptotic activity of Apo-2L in 9D cells (data not shown).

Example 11

Assay for Antibody Ability to Block Apo-2 Ligand-Induced Apoptosis

Hybridoma supernatants and purified antibodies (as described in Example 9 above) were tested for activity to block Apo-2 ligand induced 9D cell apoptosis. The 9D cells ($5 \times 10^5$ cells/0.1 ml) were suspended in complete RPMI media (RPMI plus 10% FCS, glutamine, nonessential amino acids, penicillin, streptomycin, sodium pyruvate) and placed into individual Falcon 2052 tubes. Cells were then incubated with 10 µg of antibodies in 200 µl media for 15 minutes on ice. 0.2 ml of Apo-2 ligand (2.5 µg/ml) (soluble His-tagged Apo-2L prepared as described in WO 97/25428; see also Pitti et al., supra) was suspended into complete RPMI media, and then added into the tubes containing the 9D cells. The 9D cells were incubated overnight at 37° C. and in the presence of 7% $CO_2$. The incubated cells were then harvested and washed once with PBS. The viability of the cells was determined by staining of FITC-annexin V binding to phosphatidylserine according to manufacturer recommendations (Clontech). Specifically, the cells were washed in PBS and resuspended in 200 µl binding buffer. Ten µl of annexin-V-FITC (1 µg/ml) and 10 µl of propidium iodide were added to the cells. After incubation for 15 minutes in the dark, the 9D cells were analyzed by FACS.

The results are shown in FIG. 10. Since 9D cells express more than one receptor for Apo-2L, Apo-2L can induce apoptosis in the 9D cells by interacting with either Apo-2 or the DR4 receptor. Thus, to detect any blocking activity of the Apo-2 antibodies, the interaction between DR4 and Apo-2L needed to be blocked. In combination with the anti-DR4 antibody, 4H6.17.8 (ATCC HB-12455), the Apo-2 antibody 3F11.39.7 was able to block approximately 50% of apoptosis induced by Apo-2L. The remaining approximately 50% apoptotic activity is believed to be due to the agonistic activities of these two antibodies by themselves, as shown in FIG. 10. Accordingly, it is believed that the 3F11.39.7 antibody is a blocking Apo-2 antibody or an antibody which binds Apo-2 in a mode which competes with binding of Apo-2 ligand to Apo-2.

Example 12

ELISA Assay to Test Binding of Apo-2 Antibodies to Other Apo-2 Ligand Receptors

An ELISA was conducted to determine if the monoclonal antibody described in Example 9 was able to bind other known Apo-2L receptors beside Apo-2. Specifically, the 3F11.39.7 antibody was tested for binding to DR4 [Pan et al., supra], DcR1 [Sheridan et al., supra], and DcR2 [Marsters et al., *Curr. Biol.*, 7:1003-1006 (1997)]. The ELISA was performed essentially as described in Example 9 above.

The results are shown in FIG. 11. The Apo-2 antibody 3F11.39.7 bound to Apo-2. The 3F11.39.7 antibody also showed some cross-reactivity to DR4, but not to DcR1 or DcR2.

Example 13

Antibody Isotyping

The isotype of the 3F11.39.7 antibody (as described above) was determined by coating microtiter plates with isotype specific goat anti-mouse Ig (Fisher Biotech, Pittsburgh, Pa.) overnight at 4° C. The plates were then washed with wash buffer (as described in Example 9 above). The wells in the microtiter plates were then blocked with 200 μl of 2% bovine serum albumin (BSA) and incubated at room temperature for one hour. The plates were washed again three times with wash buffer. Next, 100 μl of 5 μg/ml of purified 3F11.39.7 antibody was added to designated wells. The plates were incubated at room temperature for 30 minutes and then 50 μl HRP-conjugated goat anti-mouse IgG (as described above) was added to each well. The plates were incubated for 30 minutes at room temperature. The level of HRP bound to the plate was detected using HRP substrate as described above.

The isotyping analysis showed that the 3F11.39.7 antibody is an IgG1 antibody.

Example 14

Single-Chain Apo-2 Antibodies

A. Antibody Phage Selection Using Streptavidin-Coated Paramagnetic Beads

A phage library was selected using soluble biotinylated antigen and streptavidin-coated paramagnetic beads. The antigen, an Apo-2 ECD immunoadhesin prepared as described in Example 2B above, was biotinylated using IMMUNOPURE NHS-biotin (biotiny-N-hydroxy-succinimide, Pierce) according to manufacturer's instructions.

Two panning experiments were performed. The first experiment was designed to isolate phage clones specific for Apo-2 and which did not cross react with DR4 or DcR1. Three rounds of panning were carried out. For the first round, 10 μl of the Cambridge Antibody Technologies phage library were blocked with 1 ml of MPBST (3% dry milk powder, 1×PBS, 0.2% TWEEN) containing 800 μg of CD4-Ig, 300 μg DR4-Ig, and 200 μg of DcR1-Ig for 1 hour on a rotating wheel at room temperature (CD4-Ig, DR4, and DcR1 are described in Capon et al., *Nature,* 337:525 (1989); Pan et al., supra; and Sheridan et al., supra). Biotinylated Apo-2 ECD immunoadhesin was then added to a final concentration of 100 nM, and phage were allowed to bind antigen for 1 hour at 37° C. Meanwhile, 300 μl of DYNABEADS M-280, coated with streptavidin (DYNAL) were washed 3 times with 1 ml MPBST (using a DYNAL Magnetic Particle Concentrator) and then blocked for 2 hours at 37° C. with 1 ml fresh MPBST on a rotator. The beads were collected with the MPC, resuspended in 50 μl of MPBST, and added to the phage-plus-antigen solution. Mixing continued on a wheel at room temperature for 15 minutes. The DYNABEADS and attached phage were then washed a total of 7 times: 3 times with 1 ml PBS-TWEEN, once with MPBS, followed by 3 times with PBS.

Phage were eluted from the beads by incubating 5 minutes at room temperature with 300 μl of 100 mM triethylamine. The phage-containing supernatant was removed and neutralized with 150 μl of 1 M Tris-HCl (pH 7.4). Neutralized phage were used to infect mid-log TG1 host cells and plated on 2YT agar supplemented with 2% glucose and 100 μg/ml carbenicillin. After overnight growth at 30° C., colonies were scraped into 10 ml 2YT. 50 μl of this solution was used to inoculate 25 ml of 2YT with carbenicillin and glucose and incubated, shaking, for 2 hours at 37° C. Helper phage M13KO7 (Pharmacia) were added at a m.o.i. of 10. After adsorption, the cells were pelleted and resuspended in 25 ml of 2YT with carbenicillin (100 μg/ml) and kanamycin (50 μg/ml) and growth continued at 30° C. for 4 hours. *E. coli* were removed from the phage by centrifugation, and 1 ml of these phage (approximately $10^{12}$ c.f.u.) were used in subsequent rounds of selection.

For the second round of selection, the 1 ml of harvested phage was adjusted to 3% dry milk, 1×PBS, 0.2% TWEEN and then 100 μg DR4-Ig, 65 μg DcR1-Ig, and 500 μg of CD4-Ig were added for blocking. For selection, biotinylated Apo-2 was added at 10 nM. Washing stringency was increased to two cycles of 7 washes.

For the third round of selection, phage were blocked with only MPBST. Biotinylated Apo-2 was added to 1 nM, and washing stringency was increased to three cycles of 7 washes. Relatively few clones were obtained in this round; therefore Pan 2B, Round 3 was performed using 5 nM of biotinylated Apo-2 with all other conditions repeated as before.

A second panning experiment was performed similarly as above except that in Rounds 1 and 2, blocking of phage solutions was conducted with MPBST containing 1.0 mg/ml CD4-Ig (no other immunoadhesins) and Round 3 was blocked with MPBST only. Biotinylated Apo-2 was added at 200 nM in Round 1, 60 nM in Round 2, and 12 nM in Round 3. At each round, phage were eluted from the magnetic beads with 300 μl of 100 nM triethylamine, then with 300 μl 0.1 M Tris-HCl (pH 7.5), and then with 300 μl glycine-0.1 M HCl (pH 2.2) containing 1 mg/ml BSA. The phage obtained from the three sequential elutions were pooled and used to infect host strain TG1 as above.

B. ELISA Screening of Selected Clones

After each round of selection, individual carbenicillin-resistant colonies were screened by ELISA to identify those producing Apo-2-binding phage. Only those clones which were positive in two or more assay formats were further studied.

Individual clones were inoculated into 2TY with 2% glucose and 100 μg/ml carbenicillin in 96-well tissue culture plates and grown until turbid. Cultures were then infected at a m.o.i. of 10 with M12KO7 helper phage, and infected cells were transferred to 2YT media containing carbenicillin (100 μg/ml) and kanamycin (50 μg/ml) for growth overnight at 30° C. with gentle shaking.

NUNC MAXISORP microtiter plates were coated with 50 μl per well of Apo-2 ECD immunoadhesin, or CD4-IgG, at 2 μg/ml in 50 mM carbonate buffer (pH 9.6), at 4° C. overnight. After removing antigen, plates were blocked with 3% dry milk in PBS (MPBS) for 2 hours at room temperature.

Phage cultures were centrifuged and 100 μl of phage-containing supernatants were blocked with 20 μl of 6×PBS/18% dry milk for 1 hour at room temperature. Block was removed from titer plates and blocked phage added and allowed to bind for 1 hour at room temperature. After washing, phage were detected with a 1:5000 dilution of horseradish peroxidase-conjugated anti-M13 antibody (Pharmacia) in MPBS followed by 3',3',5',5'-tetramethylbenzidine (TMB). Reactions were stopped by the addition of H$_2$SO$_4$ and readings taken by subtracting the A$_{450nm}$ from the A$_{450nm}$.

C. DNA Fingerprinting of Clones

The diversity of Apo-2-binding clones was determined by PCR amplifying the scFv insert using primers pUC19R (5'AGC GGA TAA CAA TTT CAC ACA GG 3') (SEQ. ID. NO:12) which anneals upstream of the leader sequence and fdtetseq (5'GTC GTC TTT CCA GAC GGT AGT 3') (SEQ. ID. NO:13) which anneals in the 5' end of gene III, followed by digestion with the frequent-cutting restriction enzyme BstNI.

DNA Fingerprinting: Protocol

| Mix A: | dH20 | 67 µl |
| --- | --- | --- |
|  | 10 × ampliTaq buffer | 10 |
|  | 25 mM MgCl$_2$ | 10 |
|  | DMSO, 50% | 2 |
|  | forward primer | 1 |
| Mix B: | 2.5 mM dNTPs | 8 µl |
|  | AMPLITAQ | 0.5 |
|  | reverse primer | 1.0 |

90 µl of Mix A was placed in a reaction tube and then inoculated with a very small portion of *E. coli* colony using a yellow tip. The reaction mix was then heated in a PCR block to 98° C., for 3 minutes, removed, and placed on ice. 10 µl Mix B was then added and the reaction mix was thermocycled at 95° C., 30 sec, 55° C. 30 sec, 72° C. 1 minute 20 sec, for 25 cycles in a Perkin Elmer 2400 thermocycler. 10 µl of the resultant reaction product was then removed and run on a 1% agarose gel to test for a 1 kB band. The remaining mix was brought to 1×BstNI reaction buffer, 5 units BstNI was added and the DNA was allowed to digest for 2 hours at 60° C. The resultant samples were then electrophoresed on a GeneGel Excel 12.5% acrylamide gel (Pharmacia Biotech).

D. Sequencing of Clones

The nucleotide sequence of representative clones of each fingerprint pattern were obtained. Colonies were inoculated into 50 ml of LB medium supplemented with 2% glucose and 100 µg/ml carbenicillin, and grown overnight at 30° C. DNA was isolated using Qiagen Tip-100s and the manufacturer's protocol and cycle sequenced with fluorescent dideoxy chain terminators (Applied Biosystems). Samples were run on an Applied Biosystems 373A Automated DNA Sequencer and sequences analyzed using the program "Sequencher" (Gene Codes Corporation). The nucleotides sequences of selected antibodies 16E2, 20E6 and 24C4 are shown in SEQ ID NO:6, SEQ ID NO:7, and SEQ ID NO:8, respectively, (in FIGS. 15A, 15B and 15C respectively). The corresponding amino acid sequences of antibodies 16E2, 20E6 and 24C4 are shown in SEQ ID NO:9, SEQ ID NO:10, and SEQ ID NO:11, respectively (and in FIG. 16). In addition, FIG. 16 identifies the signal region, and heavy and light chain complementarity determining regions (underlined) of these scFv molecules. The CDR regions shown in FIG. 16 were assigned according to the methods of Kabat et al., "Sequences of Proteins of Immunological Interest," NIH Publ. No. 91-3242, 5$^{th}$ Edition.

E. Purification of scFvs with (His)$_6$

For protein purification of soluble antibody, *E. coli* strain 33D3 was transformed with phagemid DNA. Five ml of 2YT with carbenicillin and glucose was used to grow overnight cultures at 30° C. 2.5 ml of these cultures were diluted into 250 ml of the same media and grown to an OD$_{600}$ of approximately 1.2. The cells were pelleted and resuspended in 500 ml of 2YT containing IPTG (1 mM) and carbenicillin (100 µg/ml) to induce expression and grown for a further 16 hours at 22° C. Cell pellets were harvested and frozen at −20° C.

The antibodies were purified by immobilized metal chelate affinity chromatography (IMAC). Frozen pellets were resuspended in 10 ml of ice-cold shockate buffer (25 mM TRIS-HCl, 1 mM EDTA, 500 mM NaCl, 20% sucrose, 1 mM PMSF) by shaking on ice for 1 hour. Imidazole was added to 20 mM, and cell debris removed by centrifugation. The supernatants were adjusted to 1 mM MgCl$_2$ and 50 mM phosphate buffer pH 7.5. Ni-NTA agarose resin from Qiagen was used according to the manufacturer's instructions. The resin was equilibrated with 50 mM sodium phosphate buffer pH 7.5, 500 mM NaCl, 20 mM imidazole, and the shockate added. Binding occurred in either a batch mode or on a gravity flow column. The resin was then washed twice with 10 bed volumes of equilibration buffer, and twice with buffer containing imidazole increased to 50 mM. Elution of proteins was with 50 mM phosphate buffer pH 7.5, 500 mM NaCl and 250 mM imidazole. Excess salt and imidazole was removed on a PD-10 column (Pharmacia), and proteins were concentrated using a Centricom 10 to a volume of about 1 ml.

Concentration was estimated spectrophotometrically assuming an A280 nm of 1.0=0.6 mg/ml.

F. Assays to Determine Binding Specificity of Anti-Apo-2 scFvs

To evaluate the specificity of each of the scFv clones, ELISA assays were performed to evaluate binding of 16E2, 20E6 and 24C4 to Apo-2 ECD-Ig, DR4-Ig, DcR1-Ig, DcR2-Ig and CD4-Ig (described above and in Example 12).

In brief, NUNC ELISA plates were coated with 50 µl of a 1 µg/ml receptor-Ig immunoadhesin molecule in 0.05 M sodium carbonate buffer, pH 9.5, and allowed to incubate overnight at 4° C. Plates were then blocked with 285 µl ELISA diluent (PBS supplemented with 0.5% BSA, 0.05% Tween 20, pH 7.4) for at least one hour at room temperature. 50 µl of the scFvs were added to the plates in a 1:5 serial dilution and allowed to incubate for 1 hour at room temperature. After this 1 hour dilution, the plates were washed 6 times with PBS/0.05% Tween. After binding to antigen coated plates, soluble scFv was detected by adding 50 µl of 1 µg/ml Mab 9E10 (an anti-c-myc antibody; ATCC CRL 1729) per well and allowing the plates to incubate for 1 hour at room temperature. After washing the plates 6 times with PBS/0.05% Tween, 50 µl of a 1:5000 dilution of horseradish peroxidase-conjugated anti-Murine IgG antibody (Cappel catalogue: 55569) in MPBS was added to the plates and allowed to incubate for 1 hour. An observable signal was generated by adding 50 µl of 3',3',5',5'-tetramethylbenzidine (TMB) peroxidase substrate (KPL catalogue #: 50-76-00). Reactions were stopped by the addition of H$_2$SO$_4$ and readings taken by subtracting the A$_{405nm}$ from the A$_{450nm}$.

As illustrated in FIGS. 12A, 12B and 12C, the ELISA assays showed that each of these antibodies exhibited a relatively high degree of specificity for Apo-2.

Additional assays utilizing transfected cells also showed the specificity of 16E2 antibody for Apo-2. Specifically, immunohistochemistry experiments were performed to evaluate the binding specificity of the 16E2 antibody to Apo-2 and DR4-transfected CHO cells. CHO cells were transfected with vector alone or vector containing the gene for Apo-2 or DR4. The transfected cells were removed from culture plates, pelleted, and washed twice with PBS. The pellets were then resuspended in O.C.T. (Fisher), flash frozen in isopentanol and LN$_2$, and later sectioned using standard protocols. Staining of the sectioned cells was performed using a Vectastain Elite ABC kit. The sections were incubated with either anti-Apo-2 antibody 16E2 or a negative control single chain antibody.

The secondary antibody employed was either a biotinylated anti-c-myc 9E10 antibody or anti-Penta His antibody (Qiagen) followed by biotinylated anti-mouse IgG.

This immunohistochemistry assay showed specific staining of the Apo-2-transfected cells but not the DR4-transfected cells. The cellular staining was predominantly cytoplasmic.

Example 15

Assay for Ability of His-Tagged scFvs to Agonistically Induce Apoptosis

A. Annexin V-biotin/Streptavidin-[S-35] 96 Well Assays

Purified scFv antibodies (as described in Example 14 above) were tested for ability to induce Apo-2 mediated apoptosis.

In brief, SK-MES-1 cells (human lung carcinoma cell line; ATCC HTB 58) or HCT 116 cells (human colon carcinoma cell line; ATCC CCL 247) ($4 \times 10^4$ cells/well) were aliquoted into 96 well plates in assay medium (1:1 mixture of phenol-red free Dulbecco modified Eagle medium and phenol-red free Ham's F-12 nutrient mixture supplemented with 10% fetal bovine serum, 2 mM L-glutamine, 100 U/ml penicillin and 100 ug/ml streptomycin) and allowed to attach overnight at 37° C. The media was then removed and 0.1 ml of assay medium containing scFv at a final concentration of 50 ug/ml (16E2 or 20E6) was added to the wells (serial dilutions of 1:2 performed in the plates) and allowed to incubate for 1 hour at room temperature. Other single chain antibodies were used as negative controls: an anti-tissue factor scFv clone, 7D5, or a scFv referred to as 19B8. After the 1 hour incubation with scFv antibody, 0.1 ml of 10 ug/ml anti-His (Qiagen, cat. No. 1007671) or anti-c-myc antibodies were added to the appropriate wells. Wells not receiving a crosslinking antibody received media alone. The plates were then allowed to incubate for 30 minutes at room temperature. After the 30 minutes incubation, 0.1 ml of 10 ug/ml goat anti-mouse IgG (ICN cst. No. 67-029) was added to the appropriate wells. Wells not receiving anti-IgG antibody received media alone. The plates were then placed in an incubator for 15 minutes to allow the pH to return to 7.0. For positive controls, a 2 ug/ml solution of Apo-2 ligand (Apo-2L) (prepared as described in Example 11) in potassium phosphate buffer at pH 7.0 was added to the appropriate wells, with serial 2 fold dilutions carried out in the plate. The negative control wells received media alone. The cells were then incubated overnight at 37° C. in the presence of 5% $CO_2$. 0.05 ml of annexin V-biotin (1 ug/ml) in $2 \times Ca^{2+}$ binding buffer (NeXins B.V.) was then added to the wells and then allowed to mix on a shaker for 30 minutes. 0.05 ml of strepavidin-[S-35] (final concentration of $2.5 \times 10^4$ cpm/well) (Amersham) in $2 \times Ca^{2+}$ binding buffer was then added to the wells and then allowed to mix on a shaker for 30 minutes. The plates were then sealed and centrifuged for 4 minutes at 1500 rpm. To assess the extent of apoptosis, the plates were then counted on a Trialux Microbeta Counter (Wallace) to obtain cpm values corresponding to Annexin-V binding.

As shown in FIGS. 13C and 14B, the 16E2 and 20E6 antibodies agonistically induced apoptosis in SK-MES-1 cells.

B. Crystal Violet Assays

In addition to the annexin V-biotin/streptavidin-[S-35] assay described above, scFv antibodies (as described in Example 14 above) were tested for activity to induce Apo-2 mediated apoptosis via assays utilizing crystal violet.

In brief, the SK-MES-1 cells were plated at $4 \times 10^4$ cells/well in assay medium (described in Section A above) and allowed to attach overnight at 37° C. The medium was removed and 0.1 ml of assay medium containing scFv (as described in Section A above) at a final concentration of 50 µg/ml was added to the appropriate wells (wells without scFv added receive a media change). Selected wells received "pre-complexed" samples in which 10 ug/ml scFv 16E2 was combined with 100 ug/ml anti-His antibody for 5 hours at 40° C. with continuous mixing before addition to the plate. The plates were allowed to incubate for 1 hour at room temperature.

The scFv medium was removed and 0.1 ml of 10 µg/ml anti-His (Qiagen, cat. no. 1007671) or anti-c-myc antibodies diluted in assay medium was added to the wells (wells without crosslinker receive a media change.) The plates were then allowed to incubate for 30 minutes at room temperature.

The medium was then removed and 0.1 ml of 10 µg/ml Goat anti-Mouse IgG (Fc Fragment specific-ICN cst. no. 67-029) diluted in assay medium was added to the appropriate wells (wells without anti-Fc receive a media change). The plates were then placed in the incubator for 15 minutes to allow the pH to return to 7.0.

Apo-2L (stock at 100 µg/ml in potassium phosphate buffer pH 7.0) was diluted to 2 µg/ml and 0.1 ml was added to the appropriate wells. Serial two-fold dilutions were carried down the plate. The plates were then incubated overnight at 37° C.

All medium was removed from the wells and the plates were then flooded with crystal violet solution. The plates were allowed to stain for 15 minutes. The crystal violet was removed by flooding the plates with running tap water. The plates were then allowed to dry overnight.

The plates were read on an SLT plate reader at 540 nm and the data analyzed using an Excel macro and 4p-fit.

As shown in FIGS. 13A, 13B, 14A and 14B, the 16E2 and 20E6 antibodies agonistically induced apoptosis in SK-MES-1 cells.

Example 16

Assay for Ability of gD-Tagged scFvs to Agonistically Induce Apoptosis

A purified gD-tagged form of 16E2 scFv was tested for ability to induce Apo-2 mediated apoptosis in a crystal violet assay as described in Example 15 above.

A. Construction of scFv with gD Tag

The Sfi I to Not I fragment of the scFv form of 16E2 was subcloned into a derivative of pAK19 (Carter et al., *Methods: A Companion to Methods in Enzymology*, 3:183-192 (1991)) containing the phoA promoter and stII signal sequence rather than the lacZ promoter and hybrid signal sequence of the original library. For ease of purification, a DNA fragment coding for 12 amino acids (met-ala-asp-pro-asn-arg-phe-arg-gly-lys-asp-leu SEQ ID NO:14) derived from herpes simplex virus type 1 glycoprotein D (Lasky et al., *DNA*, 3:23-29 (1984)) was synthesized and inserted at the 3' end of the VL domain in place of the $(his)_6$ and c-myc epitope originally present in the Cambridge Antibody Technologies library clones.

B. Expression in *E. coli*

The plasmid containing the gene for scFv 16E2-gD was transformed into *E. coli* strain 33D3 for expression in shake flask cultures. 5 ml of 2YT with carbenicillin and glucose was used to grow overnight cultures at 30° C. 2.5 ml of these cultures were diluted into 250 ml of the same medium and grown to an $OD_{600}$ of approximately 1.0. The cells were pelleted and resuspended in 500 ml of Modified AP-5 Minimal Media containing carbenicillin (100 μg/ml) and grown for an additional 16 hours at 30° C. The cells were then pelleted and frozen.

C. Purification of scFv with gD Tag

Frozen cell paste was resuspended at 1 gm/10 ml of shockate buffer (25 mM Tris-HCl, 1 mM EDTA, 500 mM NaCl, 20% sucrose, 1 mM. PMSF, pH 7.2) and gently agitated 4 hours on ice. The cell suspension was then processed through a Polytron microfluidizer (Brinkman). Cell debris was removed by centrifugation at 10,000×g for 30 minutes. After filtration through a 0.22 micron filter, the supernatant was loaded onto an affinity column (2.5×9.0 cm) consisting of an anti-gD antibody. 5B6 (Paborsky et al., *Protein Engineering*, 3:547-553 (1990)) coupled to CNBr Sepharose which had been equilibrated with PBS. The column was washed 18 hours with PBS until the absorbance of the column effluent was equivalent to baseline. All steps were done at 4° C. at a linear flow rate of 25 cm/hour. Elution was performed with 0.1 M acetic acid, 0.5 M NaCl, pH 2.9. Column fractions were monitored by absorbance at 280 nm and peak fractions pooled, neutralized with 1.0 M Tris, pH 8.0, dialyzed against PBS and sterile filtered. The resultant protein preparations were analyzed by non-reducing SDS-PAGE.

D. Crystal Violet Assay

The apoptosis assay was performed essentially as described in Example 15(B) above except that samples were serially diluted 1:3 in the plates and the 16E2-gD tagged antibody was tested in addition to two other preparations of 16E2 scFv (referred to as Prep. A and Prep. B in FIG. 14C). The results of the assay showing apoptosis induction in SK-MES-1 cells by 16E2-gD antibody are illustrated in FIG. 14C.

DEPOSIT OF MATERIAL

The following materials have been deposited with the American Type Culture Collection, 10801 University Boulevard, Manassas, Va., USA (ATCC):

| Material | ATCC Dep. No. | Deposit Date |
|---|---|---|
| pRK5-Apo-2 | 209021 | May 8, 1997 |
| 3F11.39.7 | HB-12456 | Jan. 13, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated polypeptide that binds Apo-2 ligand and induces apoptosis, wherein said polypeptide has at least 95% amino acid sequence identity with the polypeptide having the sequence shown as amino acid residues 1 to 411 of SEQ ID NO:1.

2. An isolated polypeptide consisting of SEQ ID NO:1, wherein said polypeptide binds Apo-2 ligand and induces apoptosis.

3. An isolated polypeptide that is encoded by the cDNA clone in ATCC deposit number 209021, wherein said polypeptide binds Apo-2 ligand and induces apoptosis.

4. A pharmaceutical composition comprising the polypeptide of claim 1 and a pharmaceutically acceptable carrier.

5. An isolated soluble polypeptide comprising amino acid residues 1 to 182 of SEQ ID NO:1, wherein said polypeptide binds Apo-2 ligand.

6. An isolated polypeptide that binds Apo-2 ligand, wherein said polypeptide has at least 95% amino acid sequence identity with the polypeptide having the sequence shown as amino acid residues 1 to 411 of SEQ ID NO:1.

7. An isolated polypeptide that induces apoptosis, wherein said polypeptide has at least 95% amino acid sequence identity with the polypeptide having the sequence shown as amino acid residues 1 to 411 of SEQ ID NO:1.

8. An isolated polypeptide consisting of SEQ ID NO:1, wherein said polypeptide binds Apo-2 ligand.

9. An isolated polypeptide consisting of SEQ ID NO:1, wherein said polypeptide induces apoptosis.

10. The polypeptide of claim 2, 8, or 9 wherein the amino acid residue at position 410 of SEQ ID NO:1 is a methionine residue.

11. The polypeptide of claim 2, 8, or 9, wherein the amino acid residue at position 410 of SEQ ID NO:1 is a leucine residue.

12. An isolated polypeptide that is encoded by the cDNA clone in ATCC deposit number 209021, wherein said polypeptide induces apoptosis.

13. An isolated polypeptide that is encoded by the cDNA clone in ATCC deposit number 209021, wherein said polypeptide binds Apo-2 ligand.

14. A pharmaceutical composition comprising the polypeptide of claim 2, 3, 5, 6, 7, 8, 9, 12 or 13 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,750,118 B2 | |
| APPLICATION NO. | : 11/245053 | |
| DATED | : July 6, 2010 | |
| INVENTOR(S) | : Ashkenazi | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 445 days.

Signed and Sealed this
Eleventh Day of January, 2011

David J. Kappos
*Director of the United States Patent and Trademark Office*

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 411 amino acids
      (B) TYPE: Amino Acid
      (D) TOPOLOGY: Linear (xi) SEQUENCE DESCRIPTION: SEQ ID NO: 1:

Met Glu Gln Arg Gly Gln Asn Ala Pro Ala Ala Ser Gly Ala Arg
 1             5                 10               15

Lys Arg His Gly Pro Gly Pro Arg Glu Ala Arg Gly Ala Arg Pro

```
                    20                  25                  30
Gly Leu Arg Val Pro Lys Thr Leu Val Leu Val Val Ala Ala Val
                35                  40                  45
Leu Leu Leu Val Ser Ala Glu Ser Ala Leu Ile Thr Gln Gln Asp
                50                  55                  60
Leu Ala Pro Gln Gln Arg Ala Ala Pro Gln Gln Lys Arg Ser Ser
                65                  70                  75
Pro Ser Glu Gly Leu Cys Pro Pro Gly His His Ile Ser Glu Asp
                80                  85                  90
Gly Arg Asp Cys Ile Ser Cys Lys Tyr Gly Gln Asp Tyr Ser Thr
                95                 100                 105
His Trp Asn Asp Leu Leu Phe Cys Leu Arg Cys Thr Arg Cys Asp
               110                 115                 120
Ser Gly Glu Val Glu Leu Ser Pro Cys Thr Thr Thr Arg Asn Thr
               125                 130                 135
Val Cys Gln Cys Glu Glu Gly Thr Phe Arg Glu Glu Asp Ser Pro
               140                 145                 150
Glu Met Cys Arg Lys Cys Arg Thr Gly Cys Pro Arg Gly Met Val
               155                 160                 165
Lys Val Gly Asp Cys Thr Pro Trp Ser Asp Ile Glu Cys Val His
               170                 175                 180
Lys Glu Ser Gly Ile Ile Ile Gly Val Thr Val Ala Ala Val Val
               185                 190                 195
Leu Ile Val Ala Val Phe Val Cys Lys Ser Leu Leu Trp Lys Lys
               200                 205                 210
Val Leu Pro Tyr Leu Lys Gly Ile Cys Ser Gly Gly Gly Gly Asp
               215                 220                 225
Pro Glu Arg Val Asp Arg Ser Ser Gln Arg Pro Gly Ala Glu Asp
               230                 235                 240
Asn Val Leu Asn Glu Ile Val Ser Ile Leu Gln Pro Thr Gln Val
               245                 250                 255
Pro Glu Gln Glu Met Glu Val Gln Glu Pro Ala Glu Pro Thr Gly
               260                 265                 270
Val Asn Met Leu Ser Pro Gly Glu Ser Glu His Leu Leu Glu Pro
               275                 280                 285
Ala Glu Ala Glu Arg Ser Gln Arg Arg Arg Leu Leu Val Pro Ala
               290                 295                 300
Asn Glu Gly Asp Pro Thr Glu Thr Leu Arg Gln Cys Phe Asp Asp
               305                 310                 315
Phe Ala Asp Leu Val Pro Phe Asp Ser Trp Glu Pro Leu Met Arg
               320                 325                 330
Lys Leu Gly Leu Met Asp Asn Glu Ile Lys Val Ala Lys Ala Glu
               335                 340                 345
Ala Ala Gly His Arg Asp Thr Leu Tyr Thr Met Leu Ile Lys Trp
               350                 355                 360
Val Asn Lys Thr Gly Arg Asp Ala Ser Val His Thr Leu Leu Asp
               365                 370                 375
Ala Leu Glu Thr Leu Gly Glu Arg Leu Ala Lys Gln Lys Ile Glu
               380                 385                 390
Asp His Leu Leu Ser Ser Gly Lys Phe Met Tyr Leu Glu Gly Asn
               395                 400                 405
Ala Asp Ser Ala Xaa Ser
               410
```

(2) INFORMATION FOR SEQ ID NO: 2:

(i) SEQUENCE CHARACTERISTICS:
        (A) LENGTH: 1799 base pairs
        (B) TYPE: Nucleic Acid
        (C) STRANDEDNESS: Single
        (D) TOPOLOGY: Linear (xi) SEQUENCE DESCRIPTION: SEQ ID NO: 2:

```
CCCACGCGTC CGCATAAATC AGCACGCGGC CGGAGAACCC CGCAATCTCT            50

GCGCCCACAA AATACACCGA CGATGCCCGA TCTACTTTAA GGGCTGAAAC           100

CCACGGGCCT GAGAGACTAT AAGAGCGTTC CCTACCGCC  ATG GAA              145
                                            Met Glu
                                             1

CAA CGG GGA CAG AAC GCC CCG GCC GCT TCG GGG GCC CGG              184
Gln Arg Gly Gln Asn Ala Pro Ala Ala Ser Gly Ala Arg
      5                  10                  15

AAA AGG CAC GGC CCA GGA CCC AGG GAG GCG CGG GGA GCC              223
Lys Arg His Gly Pro Gly Pro Arg Glu Ala Arg Gly Ala
             20                  25

AGG CCT GGG CTC CGG GTC CCC AAG ACC CTT GTG CTC GTT              262
Arg Pro Gly Leu Arg Val Pro Lys Thr Leu Val Leu Val
 30                  35                  40

GTC GCC GCG GTC CTG CTG TTG GTC TCA GCT GAG TCT GCT              301
Val Ala Ala Val Leu Leu Leu Val Ser Ala Glu Ser Ala
             45                  50

CTG ATC ACC CAA CAA GAC CTA GCT CCC CAG CAG AGA GCG              340
Leu Ile Thr Gln Gln Asp Leu Ala Pro Gln Gln Arg Ala
 55                  60                  65

GCC CCA CAA CAA AAG AGG TCC AGC CCC TCA GAG GGA TTG              379
Ala Pro Gln Gln Lys Arg Ser Ser Pro Ser Glu Gly Leu
             70                  75                  80

TGT CCA CCT GGA CAC CAT ATC TCA GAA GAC GGT AGA GAT              418
Cys Pro Pro Gly His His Ile Ser Glu Asp Gly Arg Asp
             85                  90

TGC ATC TCC TGC AAA TAT GGA CAG GAC TAT AGC ACT CAC              457
Cys Ile Ser Cys Lys Tyr Gly Gln Asp Tyr Ser Thr His
 95                 100                 105

TGG AAT GAC CTC CTT TTC TGC TTG CGC TGC ACC AGG TGT              496
Trp Asn Asp Leu Leu Phe Cys Leu Arg Cys Thr Arg Cys
             110                 115

GAT TCA GGT GAA GTG GAG CTA AGT CCC TGC ACC ACG ACC              535
Asp Ser Gly Glu Val Glu Leu Ser Pro Cys Thr Thr Thr
120                 125                 130

AGA AAC ACA GTG TGT CAG TGC GAA GAA GGC ACC TTC CGG              574
Arg Asn Thr Val Cys Gln Cys Glu Glu Gly Thr Phe Arg
             135                 140                 145

GAA GAA GAT TCT CCT GAG ATG TGC CGG AAG TGC CGC ACA              613
Glu Glu Asp Ser Pro Glu Met Cys Arg Lys Cys Arg Thr
             150                 155

GGG TGT CCC AGA GGG ATG GTC AAG GTC GGT GAT TGT ACA              652
Gly Cys Pro Arg Gly Met Val Lys Val Gly Asp Cys Thr
 160                 165                 170

CCC TGG AGT GAC ATC GAA TGT GTC CAC AAA GAA TCA GGC              691
Pro Trp Ser Asp Ile Glu Cys Val His Lys Glu Ser Gly
             175                 180

ATC ATC ATA GGA GTC ACA GTT GCA GCC GTA GTC TTG ATT              730
Ile Ile Ile Gly Val Thr Val Ala Ala Val Val Leu Ile
185                 190                 195
```

```
GTG GCT GTG TTT GTT TGC AAG TCT TTA CTG TGG AAG AAA          769
Val Ala Val Phe Val Cys Lys Ser Leu Leu Trp Lys Lys
        200                 205                 210

GTC CTT CCT TAC CTG AAA GGC ATC TGC TCA GGT GGT GGT          808
Val Leu Pro Tyr Leu Lys Gly Ile Cys Ser Gly Gly Gly
                215                 220

GGG GAC CCT GAG CGT GTG GAC AGA AGC TCA CAA CGA CCT          847
Gly Asp Pro Glu Arg Val Asp Arg Ser Ser Gln Arg Pro
        225                 230                 235

GGG GCT GAG GAC AAT GTC CTC AAT GAG ATC GTG AGT ATC          886
Gly Ala Glu Asp Asn Val Leu Asn Glu Ile Val Ser Ile
                240                 245

TTG CAG CCC ACC CAG GTC CCT GAG CAG GAA ATG GAA GTC          925
Leu Gln Pro Thr Gln Val Pro Glu Gln Glu Met Glu Val
250                 255                 260

CAG GAG CCA GCA GAG CCA ACA GGT GTC AAC ATG TTG TCC          964
Gln Glu Pro Ala Glu Pro Thr Gly Val Asn Met Leu Ser
        265                 270                 275

CCC GGG GAG TCA GAG CAT CTG CTG GAA CCG GCA GAA GCT         1003
Pro Gly Glu Ser Glu His Leu Leu Glu Pro Ala Glu Ala
                280                 285

GAA AGG TCT CAG AGG AGG AGG CTG CTG GTT CCA GCA AAT         1042
Glu Arg Ser Gln Arg Arg Arg Leu Leu Val Pro Ala Asn
        290                 295                 300

GAA GGT GAT CCC ACT GAG ACT CTG AGA CAG TGC TTC GAT         1081
Glu Gly Asp Pro Thr Glu Thr Leu Arg Gln Cys Phe Asp
                305                 310

GAC TTT GCA GAC TTG GTG CCC TTT GAC TCC TGG GAG CCG         1120
Asp Phe Ala Asp Leu Val Pro Phe Asp Ser Trp Glu Pro
315                 320                 325

CTC ATG AGG AAG TTG GGC CTC ATG GAC AAT GAG ATA AAG         1159
Leu Met Arg Lys Leu Gly Leu Met Asp Asn Glu Ile Lys
        330                 335                 340

GTG GCT AAA GCT GAG GCA GCG GGC CAC AGG GAC ACC TTG         1198
Val Ala Lys Ala Glu Ala Ala Gly His Arg Asp Thr Leu
                345                 350

TAC ACG ATG CTG ATA AAG TGG GTC AAC AAA ACC GGG CGA         1237
Tyr Thr Met Leu Ile Lys Trp Val Asn Lys Thr Gly Arg
        355                 360                 365

GAT GCC TCT GTC CAC ACC CTG CTG GAT GCC TTG GAG ACG         1276
Asp Ala Ser Val His Thr Leu Leu Asp Ala Leu Glu Thr
                370                 375

CTG GGA GAG AGA CTT GCC AAG CAG AAG ATT GAG GAC CAC         1315
Leu Gly Glu Arg Leu Ala Lys Gln Lys Ile Glu Asp His
380                 385                 390

TTG TTG AGC TCT GGA AAG TTC ATG TAT CTA GAA GGT AAT         1354
Leu Leu Ser Ser Gly Lys Phe Met Tyr Leu Glu Gly Asn
        395                 400                 405

GCA GAC TCT GCC WTG TCC TAAGTGTG ATTCTCTTCA GGAAGTGAGA      1400
Ala Asp Ser Ala Xaa Ser
                410 411

CCTTCCCTGG TTTACCTTTT TTCTGGAAAA AGCCCAACTG GACTCCAGTC      1450

AGTAGGAAAG TGCCACAATT GTCACATGAC CGGTACTGGA AGAAACTCTC      1500

CCATCCAACA TCACCCAGTG GATGGAACAT CCTGTAACTT TTCACTGCAC      1550

TTGGCATTAT TTTATAAGC TGAATGTGAT AATAAGGACA CTATGGAAAT       1600

GTCTGGATCA TTCCGTTTGT GCGTACTTTG AGATTTGGTT TGGGATGTCA      1650
```

-continued

```
TTGTTTTCAC AGCACTTTTT TATCCTAATG TAAATGCTTT ATTTATTTAT                    1700

TTGGGCTACA TTGTAAGATC CATCTACAAA AAAAAAAAAA AAAAAAAAAG                    1750

GGCGGCCGCG ACTCTAGAGT CGACCTGCAG AAGCTTGGCC GCCATGGCC                     1799

(2) INFORMATION FOR SEQ ID NO: 3:

(i) SEQUENCE CHARACTERISTICS:
        (A) LENGTH: 70 base pairs
        (B) TYPE: Nucleic Acid
        (C) STRANDEDNESS: Single
        (D) TOPOLOGY: Linear (xi) SEQUENCE DESCRIPTION: SEQ ID NO: 3:

GGGAGCCGCT CATGAGGAAG TTGGGCCTCA TGGACAATGA GATAAAGGTG                      50

GCTAAAGCTG AGGCAGCGGG                                                      70

(2) INFORMATION FOR SEQ ID NO: 4:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear (xi) SEQUENCE DESCRIPTION: SEQ ID NO: 4:

ATCAGGGACT TTCCGCTGGG GACTTTCCG                                            29

(2) INFORMATION FOR SEQ ID NO: 5:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

AGGATGGGAA GTGTGTGATA TATCCTTGAT                                           30

(2) INFORMATION FOR SEQ ID NO: 6:

(i) SEQUENCE CHARACTERISTICS:
        (A) LENGTH: 930 base pairs
        (B) TYPE: Nucleic Acid
        (C) STRANDEDNESS: Single
        (D) TOPOLOGY: Linear (xi) SEQUENCE DESCRIPTION: SEQ ID NO: 6:

ATG ACC ATG ATT ACG CCA AGC TTT GGA GCC TTT TTT                        36
    Met Thr Met Ile Thr Pro Ser Phe Gly Ala Phe Phe
     1               5                  10

TTG GAG ATT TTC AAC GTG AAA AAA TTA TTA TTC GCA ATT                        75
Leu Glu Ile Phe Asn Val Lys Lys Leu Leu Phe Ala Ile
        15                  20                  25

CCT TTA GTT GTT CCT TTC TAT GCG GCC CAG CCG GCC ATG                       114
Pro Leu Val Val Pro Phe Tyr Ala Ala Gln Pro Ala Met
                30                  35

GCC GAG GTG CAG CTG GTG CAG TCT GGG GGA GGT GTG GAA                       153
Ala Glu Val Gln Leu Val Gln Ser Gly Gly Gly Val Glu
        40                  45                  50

CGG CCG GGG GGG TCC CTG AGA CTC TCC TGT GCA GCC TCT                       192
Arg Pro Gly Gly Ser Leu Arg Leu Ser Cys Ala Ala Ser
                55                  60

GGA TTC ACC TTT GAT GAT TAT GGC ATG AGC TGG GTC CGC                       231
```

```
Gly Phe Thr Phe Asp Asp Tyr Gly Met Ser Trp Val Arg
 65                  70                  75

CAA GCT CCA GGG AAG GGG CTG GAG TGG GTC TCT GGT ATT          270
Gln Ala Pro Gly Lys Gly Leu Glu Trp Val Ser Gly Ile
             80                  85                  90

AAT TGG AAT GGT GGT AGC ACA GGA TAT GCA GAC TCT GTG          309
Asn Trp Asn Gly Gly Ser Thr Gly Tyr Ala Asp Ser Val
                 95                 100

AAG GGC CGA GTC ACC ATC TCC AGA GAC AAC GCC AAG AAC          348
Lys Gly Arg Val Thr Ile Ser Arg Asp Asn Ala Lys Asn
        105                 110                 115

TCC CTG TAT CTG CAA ATG AAC AGC CTG AGA GCC GAG GAC          387
Ser Leu Tyr Leu Gln Met Asn Ser Leu Arg Ala Glu Asp
                120                 125

ACG GCC GTA TAT TAC TGT GCG AAA ATC CTG GGT GCC GGA          426
Thr Ala Val Tyr Tyr Cys Ala Lys Ile Leu Gly Ala Gly
130                 135                 140

CGG GGC TGG TAC TTC GAT CTC TGG GGG AAG GGG ACC ACG          465
Arg Gly Trp Tyr Phe Asp Leu Trp Gly Lys Gly Thr Thr
            145                 150                 155

GTC ACC GTC TCG AGT GGT GGA GGC GGT TCA GGC GGA GGT          504
Val Thr Val Ser Ser Gly Gly Gly Gly Ser Gly Gly Gly
                160                 165

GGC AGC GGC GGT GGC GGA TCG TCT GAG CTG ACT CAG GAC          543
Gly Ser Gly Gly Gly Gly Ser Ser Glu Leu Thr Gln Asp
        170                 175                 180

CCT GCT GTG TCT GTG GCC TTG GGA CAG ACA GTC AGG ATC          582
Pro Ala Val Ser Val Ala Leu Gly Gln Thr Val Arg Ile
                185                 190

ACA TGC CAA GGA GAC AGC CTC AGA AGC TAT TAT GCA AGC          621
Thr Cys Gln Gly Asp Ser Leu Arg Ser Tyr Tyr Ala Ser
195                 200                 205

TGG TAC CAG CAG AAG CCA GGA CAG GCC CCT GTA CTT GTC          660
Trp Tyr Gln Gln Lys Pro Gly Gln Ala Pro Val Leu Val
            210                 215                 220

ATC TAT GGT AAA AAC AAC CGG CCC TCA GGG ATC CCA GAC          699
Ile Tyr Gly Lys Asn Asn Arg Pro Ser Gly Ile Pro Asp
                225                 230

CGA TTC TCT GGC TCC AGC TCA GGA AAC ACA GCT TCC TTG          738
Arg Phe Ser Gly Ser Ser Ser Gly Asn Thr Ala Ser Leu
        235                 240                 245

ACC ATC ACT GGG GCT CAG GCG GAA GAT GAG GCT GAC TAT          777
Thr Ile Thr Gly Ala Gln Ala Glu Asp Glu Ala Asp Tyr
                250                 255

TAC TGT AAC TCC CGG GAC AGC AGT GGT AAC CAT GTG GTA          816
Tyr Cys Asn Ser Arg Asp Ser Ser Gly Asn His Val Val
260                 265                 270

TTC GGC GGA GGG ACC AAG CTG ACC GTC CTA GGT GCG GCC          855
Phe Gly Gly Gly Thr Lys Leu Thr Val Leu Gly Ala Ala
            275                 280                 285

GCA CAT CAT CAT CAC CAT CAC GGG GCA GCA GAA CAA AAA          894
Ala His His His His His His Gly Ala Ala Glu Gln Lys
                290                 295

CTC ATC TCA GAA GAG GAT CTG AAT GGG GCC GCA TAG              930
Leu Ile Ser Glu Glu Asp Leu Asn Gly Ala Ala
300                 305                 309
```

(2) INFORMATION FOR SEQ ID NO: 7:

(i) SEQUENCE CHARACTERISTICS:

(A) LENGTH: 939 base pairs
(B) TYPE: Nucleic Acid
(C) STRANDEDNESS: Single
(D) TOPOLOGY: Linear (xi) SEQUENCE DESCRIPTION: SEQ ID NO: 7:

| | | | | | | | | | | | |
|---|---|---|---|---|---|---|---|---|---|---|---|
| ATG | ACC | ATG | ATT | ACG | CCA | AGC | TTT | GGA | GCC | TTT | TTT | 36 |
| Met | Thr | Met | Ile | Thr | Pro | Ser | Phe | Gly | Ala | Phe | Phe | |
| 1 | | | | 5 | | | | | 10 | | | |

```
TTG GAG ATT TTC AAC GTG AAA AAA TTA TTA TTC GCA ATT              75
Leu Glu Ile Phe Asn Val Lys Lys Leu Leu Phe Ala Ile
         15                  20                  25

CCT TTA GTT GTT CCT TTC TAT GCG GCC CAG CCG GCC ATG             114
Pro Leu Val Val Pro Phe Tyr Ala Ala Gln Pro Ala Met
                 30                  35

GCC GGG GTG CAG CTG GTG GAG TCT GGG GGA GGC TTG GTC             153
Ala Gly Val Gln Leu Val Glu Ser Gly Gly Gly Leu Val
 40                  45                  50

CAG CCT GGG GGG TCC CTG AGA CTC TCC TGT GCA GCC TCT             192
Gln Pro Gly Gly Ser Leu Arg Leu Ser Cys Ala Ala Ser
             55                  60

GGA TTC ACC TTT AGT AGC TAT TGG ATG AGC TGG GTC CGC             231
Gly Phe Thr Phe Ser Ser Tyr Trp Met Ser Trp Val Arg
 65                  70                  75

CAG GCT CCA GGG AAG GGG CTG GAG TGG GTG GCC AAC ATA             270
Gln Ala Pro Gly Lys Gly Leu Glu Trp Val Ala Asn Ile
             80                  85                  90

AAG CAA GAT GGA AGT GAG AAA TAC TAT GTG GAC TCT GTG             309
Lys Gln Asp Gly Ser Glu Lys Tyr Tyr Val Asp Ser Val
                 95                 100

AAG GGC CGA TTC ACC ATC TCC AGA GAC AAC GCC AAG AAC             348
Lys Gly Arg Phe Thr Ile Ser Arg Asp Asn Ala Lys Asn
            105                 110                 115

TCA CTG TAT CTG CAA ATG AAC AGC CTG AGA GCC GAG GAC             387
Ser Leu Tyr Leu Gln Met Asn Ser Leu Arg Ala Glu Asp
                120                 125

ACG GCT GTG TAT TAC TGT GCG AGA GAT CTT TTA AAG GTC             426
Thr Ala Val Tyr Tyr Cys Ala Arg Asp Leu Leu Lys Val
130                 135                 140

AAG GGC AGC TCG TCT GGG TGG TTC GAC CCC TGG GGG AGA             465
Lys Gly Ser Ser Ser Gly Trp Phe Asp Pro Trp Gly Arg
            145                 150                 155

GGG ACC ACG GTC ACC GTC TCG AGT GGT GGA GGC GGT TCA             504
Gly Thr Thr Val Thr Val Ser Ser Gly Gly Gly Gly Ser
                160                 165

GGC GGA GGT GGT AGC GGC GGT GGC GGA TCG TCT GAG CTG             543
Gly Gly Gly Gly Ser Gly Gly Gly Gly Ser Ser Glu Leu
170                 175                 180

ACT CAG GAC CCT GCT GTG TCT GTG GCC TTG GGA CAG ACA             582
Thr Gln Asp Pro Ala Val Ser Val Ala Leu Gly Gln Thr
            185                 190

GTC AGG ATC ACA TGC CAA GGA GAC AGC CTC AGA AGC TAT             621
Val Arg Ile Thr Cys Gln Gly Asp Ser Leu Arg Ser Tyr
195                 200                 205

TAT GCA AGC TGG TAC CAG CAG AAG CCA GGA CAG GCC CCT             660
Tyr Ala Ser Trp Tyr Gln Gln Lys Pro Gly Gln Ala Pro
            210                 215                 220

GTA CTT GTC ATC TAT GGT AAA AAC AAC CGG CCC TCA GGG             699
Val Leu Val Ile Tyr Gly Lys Asn Asn Arg Pro Ser Gly
                225                 230
```

```
ATC CCA GAC CGA TTC TCT GGC TCC AGC TCA GGA AAC ACA           738
Ile Pro Asp Arg Phe Ser Gly Ser Ser Ser Gly Asn Thr
235                 240                 245

GCT TCC TTG ACC ATC ACT GGG GCT CAG GCG GAA GAT GAG           777
Ala Ser Leu Thr Ile Thr Gly Ala Gln Ala Glu Asp Glu
        250                 255

GCT GAC TAT TAC TGT AAC TCC CGG GAC AGC AGT GGT AAC           816
Ala Asp Tyr Tyr Cys Asn Ser Arg Asp Ser Ser Gly Asn
260                 265                 270

CAT GTG GTA TTC GGC GGA GGG ACC AAG CTG ACC GTC CTA           855
His Val Val Phe Gly Gly Gly Thr Lys Leu Thr Val Leu
            275                 280                 285

GGT GCG GCC GCA CAT CAT CAT CAC CAC GGG GCC GCA               894
Gly Ala Ala Ala His His His His His Gly Ala Ala
                290                 295

GAA CAA AAA CTC ATC TCA GAA GAG GAT CTG AAT GGG GCC           933
Glu Gln Lys Leu Ile Ser Glu Glu Asp Leu Asn Gly Ala
300                 305                 310

GCA TAG                                                        939
Ala
312

(2) INFORMATION FOR SEQ ID NO: 8:

(i) SEQUENCE CHARACTERISTICS:
        (A) LENGTH: 933 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

ATG ACC ATG ATT ACG CCA AGC TTT GGA GCC TTT TTT            36
    Met Thr Met Ile Thr Pro Ser Phe Gly Ala Phe Phe
    1               5                   10

TTG GAG ATT TTC AAC GTG AAA AAA TTA TTA TTC GCA ATT            75
Leu Glu Ile Phe Asn Val Lys Lys Leu Leu Phe Ala Ile
        15                  20                  25

CCT TTA GTT GTT CCT TTC TAT GCG GCC CAG CCG GCC ATG            114
Pro Leu Val Val Pro Phe Tyr Ala Ala Gln Pro Ala Met
                30                  35

GCC CAG GTG CAG CTG GTG CAG TCT GGG GGA GGC GTG GTC            153
Ala Gln Val Gln Leu Val Gln Ser Gly Gly Gly Val Val
    40                  45                  50

CAG CCT GGG CGG TCC CTG AGA CTC TCC TGT GCA GCT TCT            192
Gln Pro Gly Arg Ser Leu Arg Leu Ser Cys Ala Ala Ser
            55                  60

GGG TTC ATT TTC AGT AGT TAT GGG ATG CAC TGG GTC CGC            231
Gly Phe Ile Phe Ser Ser Tyr Gly Met His Trp Val Arg
65                  70                  75

CAG GCT CCA GGC AAG GGG CTG GAG TGG GTG GCA GGT ATT            270
Gln Ala Pro Gly Lys Gly Leu Glu Trp Val Ala Gly Ile
        80                  85                  90

TTT TAT GAT GGA GGT AAT AAA TAC TAT GCA GAC TCC GTG            309
Phe Tyr Asp Gly Gly Asn Lys Tyr Tyr Ala Asp Ser Val
                95                  100

AAG GGC CGA TTC ACC ATC TCC AGA GAC AAT TCC AAG AAC            348
Lys Gly Arg Phe Thr Ile Ser Arg Asp Asn Ser Lys Asn
    105                 110                 115

ACG CTG TAT CTG CAA ATG AAC AGC CTG AGA GCT GAG GAC            387
Thr Leu Tyr Leu Gln Met Asn Ser Leu Arg Ala Glu Asp
            120                 125
```

```
ACG GCT GTG TAT TAC TGT GCG AGA GAT AGG GGC TAC TAC            426
Thr Ala Val Tyr Tyr Cys Ala Arg Asp Arg Gly Tyr Tyr
130                 135                 140

TAC ATG GAC GTC TGG GGC AAA GGG ACC ACG GTC ACC GTC            465
Tyr Met Asp Val Trp Gly Lys Gly Thr Thr Val Thr Val
        145                 150                 155

TCC TCA GGT GGA GGC GGT TCA GGC GGA GGT GGC TCT GGC            504
Ser Ser Gly Gly Gly Gly Ser Gly Gly Gly Gly Ser Gly
                160                 165

GGT GGC GGA TCG CAG TCT GTG TTG ACG CAG CCG CCC TCA            543
Gly Gly Gly Ser Gln Ser Val Leu Thr Gln Pro Pro Ser
170                 175                 180

GTG TCT GGG GCC CCA GGA CAG AGG GTC ACC ATC TCC TGC            582
Val Ser Gly Ala Pro Gly Gln Arg Val Thr Ile Ser Cys
            185                 190

ACT GGG AGA AGC TCC AAC ATC GGG GCA GGT CAT GAT GTA            621
Thr Gly Arg Ser Ser Asn Ile Gly Ala Gly His Asp Val
195                 200                 205

CAC TGG TAC CAG CAA CTT CCA GGA ACA GCC CCC AAA CTC            660
His Trp Tyr Gln Gln Leu Pro Gly Thr Ala Pro Lys Leu
            210                 215                 220

CTC ATC TAT GAT GAC AGC AAT CGG CCC TCA GGG GTC CCT            699
Leu Ile Tyr Asp Asp Ser Asn Arg Pro Ser Gly Val Pro
                225                 230

GAC CGA TTC TCT GGC TCC AGG TCT GGC ACC TCA GCC TCC            738
Asp Arg Phe Ser Gly Ser Arg Ser Gly Thr Ser Ala Ser
        235                 240                 245

CTG GCC ATC ACT GGG CTC CAG GCT GAA GAT GAG GCT GAT            777
Leu Ala Ile Thr Gly Leu Gln Ala Glu Asp Glu Ala Asp
            250                 255

TAT TAC TGC CAG TCC TAT GAC AGC AGC CTG AGG GGT TCG            816
Tyr Tyr Cys Gln Ser Tyr Asp Ser Ser Leu Arg Gly Ser
260                 265                 270

GTA TTC GGC GGA GGG ACC AAG GTC ACT GTC CTA GGT GCG            855
Val Phe Gly Gly Gly Thr Lys Val Thr Val Leu Gly Ala
            275                 280                 285

GCC GCA CAT CAT CAT CAC CAT CAC GGG GCC GCA GAA CAA            894
Ala Ala His His His His His His Gly Ala Ala Glu Gln
                290                 295

AAA CTC ATC TCA GAA GAG GAT CTG AAT GGG GCC GCA                930
Lys Leu Ile Ser Glu Glu Asp Leu Asn Gly Ala Ala
300                 305                 310

TAG                                                            933

(2) INFORMATION FOR SEQ ID NO: 9:

(i) SEQUENCE CHARACTERISTICS:
        (A) LENGTH: 309 amino acids
        (B) TYPE: Amino Acid
        (D) TOPOLOGY: Linear (xi) SEQUENCE DESCRIPTION: SEQ ID NO: 9:

Met Thr Met Ile Thr Pro Ser Phe Gly Ala Phe Phe Leu Glu Ile
  1               5                  10                  15

Phe Asn Val Lys Lys Leu Leu Phe Ala Ile Pro Leu Val Val Pro
                 20                  25                  30

Phe Tyr Ala Ala Gln Pro Ala Met Ala Glu Val Gln Leu Val Gln
                 35                  40                  45

Ser Gly Gly Gly Val Glu Arg Pro Gly Gly Ser Leu Arg Leu Ser
                 50                  55                  60
```

```
Cys Ala Ala Ser Gly Phe Thr Phe Asp Asp Tyr Gly Met Ser Trp
                65                  70                  75

Val Arg Gln Ala Pro Gly Lys Gly Leu Glu Trp Val Ser Gly Ile
                80                  85                  90

Asn Trp Asn Gly Gly Ser Thr Gly Tyr Ala Asp Ser Val Lys Gly
                95                 100                 105

Arg Val Thr Ile Ser Arg Asp Asn Ala Lys Asn Ser Leu Tyr Leu
               110                 115                 120

Gln Met Asn Ser Leu Arg Ala Glu Asp Thr Ala Val Tyr Tyr Cys
               125                 130                 135

Ala Lys Ile Leu Gly Ala Gly Arg Gly Trp Tyr Phe Asp Leu Trp
               140                 145                 150

Gly Lys Gly Thr Thr Val Thr Val Ser Ser Gly Gly Gly Gly Ser
               155                 160                 165

Gly Gly Gly Gly Ser Gly Gly Gly Ser Ser Glu Leu Thr Gln
               170                 175                 180

Asp Pro Ala Val Ser Val Ala Leu Gly Gln Thr Val Arg Ile Thr
               185                 190                 195

Cys Gln Gly Asp Ser Leu Arg Ser Tyr Tyr Ala Ser Trp Tyr Gln
               200                 205                 210

Gln Lys Pro Gly Gln Ala Pro Val Leu Val Ile Tyr Gly Lys Asn
               215                 220                 225

Asn Arg Pro Ser Gly Ile Pro Asp Arg Phe Ser Gly Ser Ser Ser
               230                 235                 240

Gly Asn Thr Ala Ser Leu Thr Ile Thr Gly Ala Gln Ala Glu Asp
               245                 250                 255

Glu Ala Asp Tyr Tyr Cys Asn Ser Arg Asp Ser Ser Gly Asn His
               260                 265                 270

Val Val Phe Gly Gly Gly Thr Lys Leu Thr Val Leu Gly Ala Ala
               275                 280                 285

Ala His His His His His His Gly Ala Ala Glu Gln Lys Leu Ile
               290                 295                 300

Ser Glu Glu Asp Leu Asn Gly Ala Ala
               305

(2) INFORMATION FOR SEQ ID NO: 10:

(i) SEQUENCE CHARACTERISTICS:
        (A) LENGTH: 312 amino acids
        (B) TYPE: Amino Acid
        (D) TOPOLOGY: Linear (xi) SEQUENCE DESCRIPTION: SEQ ID NO: 10:

Met Thr Met Ile Thr Pro Ser Phe Gly Ala Phe Phe Leu Glu Ile
  1               5                  10                  15

Phe Asn Val Lys Lys Leu Leu Phe Ala Ile Pro Leu Val Val Pro
                 20                  25                  30

Phe Tyr Ala Ala Gln Pro Ala Met Ala Gly Val Gln Leu Val Glu
                 35                  40                  45

Ser Gly Gly Gly Leu Val Gln Pro Gly Gly Ser Leu Arg Leu Ser
                 50                  55                  60

Cys Ala Ala Ser Gly Phe Thr Phe Ser Ser Tyr Trp Met Ser Trp
                 65                  70                  75

Val Arg Gln Ala Pro Gly Lys Gly Leu Glu Trp Val Ala Asn Ile
                 80                  85                  90
```

```
Lys Gln Asp Gly Ser Glu Lys Tyr Tyr Val Asp Ser Val Lys Gly
                 95                 100                 105

Arg Phe Thr Ile Ser Arg Asp Asn Ala Lys Asn Ser Leu Tyr Leu
            110                 115                 120

Gln Met Asn Ser Leu Arg Ala Glu Asp Thr Ala Val Tyr Tyr Cys
            125                 130                 135

Ala Arg Asp Leu Leu Lys Val Lys Gly Ser Ser Gly Trp Phe
            140                 145                 150

Asp Pro Trp Gly Arg Gly Thr Thr Val Thr Val Ser Ser Gly Gly
            155                 160                 165

Gly Gly Ser Gly Gly Gly Ser Gly Gly Gly Ser Ser Glu
            170                 175                 180

Leu Thr Gln Asp Pro Ala Val Ser Val Ala Leu Gly Gln Thr Val
            185                 190                 195

Arg Ile Thr Cys Gln Gly Asp Ser Leu Arg Ser Tyr Tyr Ala Ser
            200                 205                 210

Trp Tyr Gln Gln Lys Pro Gly Gln Ala Pro Val Leu Val Ile Tyr
            215                 220                 225

Gly Lys Asn Asn Arg Pro Ser Gly Ile Pro Asp Arg Phe Ser Gly
            230                 235                 240

Ser Ser Ser Gly Asn Thr Ala Ser Leu Thr Ile Thr Gly Ala Gln
            245                 250                 255

Ala Glu Asp Glu Ala Asp Tyr Tyr Cys Asn Ser Arg Asp Ser Ser
            260                 265                 270

Gly Asn His Val Val Phe Gly Gly Gly Thr Lys Leu Thr Val Leu
            275                 280                 285

Gly Ala Ala Ala His His His His His His Gly Ala Ala Glu Gln
            290                 295                 300

Lys Leu Ile Ser Glu Glu Asp Leu Asn Gly Ala Ala
            305                 310

(2) INFORMATION FOR SEQ ID NO: 11:

(i) SEQUENCE CHARACTERISTICS:
        (A) LENGTH: 310 amino acids
        (B) TYPE: Amino Acid
        (D) TOPOLOGY: Linear (xi) SEQUENCE DESCRIPTION: SEQ ID NO: 11:

Met Thr Met Ile Thr Pro Ser Phe Gly Ala Phe Phe Leu Glu Ile
  1               5                  10                  15

Phe Asn Val Lys Lys Leu Leu Phe Ala Ile Pro Leu Val Val Pro
             20                  25                  30

Phe Tyr Ala Ala Gln Pro Ala Met Ala Gln Val Gln Leu Val Gln
             35                  40                  45

Ser Gly Gly Gly Val Val Gln Pro Gly Arg Ser Leu Arg Leu Ser
             50                  55                  60

Cys Ala Ala Ser Gly Phe Ile Phe Ser Ser Tyr Gly Met His Trp
             65                  70                  75

Val Arg Gln Ala Pro Gly Lys Gly Leu Glu Trp Val Ala Gly Ile
             80                  85                  90

Phe Tyr Asp Gly Gly Asn Lys Tyr Tyr Ala Asp Ser Val Lys Gly
             95                 100                 105

Arg Phe Thr Ile Ser Arg Asp Asn Ser Lys Asn Thr Leu Tyr Leu
            110                 115                 120
```

```
Gln Met Asn Ser Leu Arg Ala Glu Asp Thr Ala Val Tyr Tyr Cys
            125                 130                 135

Ala Arg Asp Arg Gly Tyr Tyr Tyr Met Asp Val Trp Gly Lys Gly
        140                 145                 150

Thr Thr Val Thr Val Ser Ser Gly Gly Gly Ser Gly Gly Gly Gly
        155                 160                 165

Gly Ser Gly Gly Gly Gly Ser Gln Ser Val Leu Thr Gln Pro Pro
        170                 175                 180

Ser Val Ser Gly Ala Pro Gly Gln Arg Val Thr Ile Ser Cys Thr
        185                 190                 195

Gly Arg Ser Ser Asn Ile Gly Ala Gly His Asp Val His Trp Tyr
        200                 205                 210

Gln Gln Leu Pro Gly Thr Ala Pro Lys Leu Leu Ile Tyr Asp Asp
        215                 220                 225

Ser Asn Arg Pro Ser Gly Val Pro Asp Arg Phe Ser Gly Ser Arg
        230                 235                 240

Ser Gly Thr Ser Ala Ser Leu Ala Ile Thr Gly Leu Gln Ala Glu
        245                 250                 255

Asp Glu Ala Asp Tyr Tyr Cys Gln Ser Tyr Asp Ser Ser Leu Arg
        260                 265                 270

Gly Ser Val Phe Gly Gly Gly Thr Lys Val Thr Val Leu Gly Ala
        275                 280                 285

Ala Ala His His His His His His Gly Ala Ala Glu Gln Lys Leu
        290                 295                 300

Ile Ser Glu Glu Asp Leu Asn Gly Ala Ala
        305                 310

(2) INFORMATION FOR SEQ ID NO: 12:

(i) SEQUENCE CHARACTERISTICS:
        (A) LENGTH: 23 base pairs
        (B) TYPE: Nucleic Acid
        (C) STRANDEDNESS: Single
        (D) TOPOLOGY: Linear (xi) SEQUENCE DESCRIPTION: SEQ ID NO: 12:

AGCGGATAAC AATTTCACAC AGG                                              23

(2) INFORMATION FOR SEQ ID NO: 13:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 13:

GTCGTCTTTC CAGACGGTAG T                                                21

(2) INFORMATION FOR SEQ ID NO: 14:

(i) SEQUENCE CHARACTERISTICS:
        (A) LENGTH: 12 amino acids
        (B) TYPE: Amino Acid
        (D) TOPOLOGY: Linear (xi) SEQUENCE DESCRIPTION: SEQ ID NO: 14:

Met Ala Asp Pro Asn Arg Phe Arg Gly Lys Asp Leu
 1               5                  10
```

(2) INFORMATION FOR SEQ ID NO: 15:

(i) SEQUENCE CHARACTERISTICS:
        (A) LENGTH: 76 amino acids
        (B) TYPE: Amino Acid
        (D) TOPOLOGY: <Unknown>

(xi) SEQUENCE DESCRIPTION: SEQ ID NO: 15:

```
Phe Ala Asp Leu Val Pro Phe Asp Ser Trp Glu Pro Leu Met Arg
 1               5                  10                  15

Lys Leu Gly Leu Met Asp Asn Glu Ile Lys Val Ala Lys Ala Glu
                20                  25                  30

Ala Ala Gly His Arg Asp Thr Leu Tyr Thr Met Leu Ile Lys Trp
                35                  40                  45

Val Asn Lys Thr Gly Arg Asp Ala Ser Val His Thr Leu Leu Asp
                50                  55                  60

Ala Leu Glu Thr Leu Gly Glu Arg Leu Ala Lys Gln Lys Ile Glu
                65                  70                  75

Asp
```

(2) INFORMATION FOR SEQ ID NO: 16:

(i) SEQUENCE CHARACTERISTICS:
        (A) LENGTH: 76 amino acids
        (B) TYPE: Amino Acid
        (D) TOPOLOGY: <Unknown>

(xi) SEQUENCE DESCRIPTION: SEQ ID NO: 16:

```
Phe Ala Asn Ile Val Pro Phe Asp Ser Trp Asp Gln Leu Met Arg
 1               5                  10                  15

Gln Leu Asp Leu Thr Lys Asn Glu Ile Asp Val Val Arg Ala Gly
                20                  25                  30

Thr Ala Gly Pro Gly Asp Ala Leu Tyr Ala Met Leu Met Lys Trp
                35                  40                  45

Val Asn Lys Thr Gly Arg Asn Ala Ser Ile His Thr Leu Leu Asp
                50                  55                  60

Ala Leu Glu Arg Met Glu Glu Arg His Ala Lys Glu Lys Ile Gln
                65                  70                  75

Asp
```

(2) INFORMATION FOR SEQ ID NO: 17:

(i) SEQUENCE CHARACTERISTICS:
        (A) LENGTH: 74 amino acids
        (B) TYPE: Amino Acid
        (D) TOPOLOGY: <Unknown>

(xi) SEQUENCE DESCRIPTION: SEQ ID NO: 17:

```
Val Met Asp Ala Val Pro Ala Arg Arg Trp Lys Glu Phe Val Arg
 1               5                  10                  15

Thr Leu Gly Leu Arg Glu Ala Glu Ile Glu Ala Val Glu Val Glu
                20                  25                  30

Ile Gly Arg Phe Arg Asp Gln Gln Tyr Glu Met Leu Lys Arg Trp
                35                  40                  45

Arg Gln Gln Gln Pro Ala Gly Leu Gly Ala Val Tyr Ala Ala Leu
                50                  55                  60

Glu Arg Met Gly Leu Asp Gly Cys Val Glu Asp Leu Arg Ser
                65                  70
```

(2) INFORMATION FOR SEQ ID NO: 18:

(i) SEQUENCE CHARACTERISTICS:
        (A) LENGTH: 78 amino acids
        (B) TYPE: Amino Acid
        (D) TOPOLOGY: <Unknown>

(xi) SEQUENCE DESCRIPTION: SEQ ID NO: 18:

```
Val Val Glu Asn Val Pro Pro Leu Arg Trp Lys Glu Phe Val Arg
 1               5                  10                  15

Arg Leu Gly Leu Ser Asp His Glu Ile Asp Arg Leu Glu Leu Gln
                20                  25                  30

Asn Gly Arg Cys Leu Arg Glu Ala Gln Tyr Ser Met Leu Ala Thr
                35                  40                  45

Trp Arg Arg Arg Thr Pro Arg Arg Glu Ala Thr Leu Glu Leu Leu
                50                  55                  60

Gly Arg Val Leu Arg Asp Met Asp Leu Leu Gly Cys Leu Glu Asp
                65                  70                  75

Ile Glu Glu
```

(2) INFORMATION FOR SEQ ID NO: 19:

(i) SEQUENCE CHARACTERISTICS:
        (A) LENGTH: 77 amino acids
        (B) TYPE: Amino Acid
        (D) TOPOLOGY: <Unknown>

(xi) SEQUENCE DESCRIPTION: SEQ ID NO: 19:

```
Ile Ala Gly Val Met Thr Leu Ser Gln Val Lys Gly Phe Val Arg
 1               5                  10                  15

Lys Asn Gly Val Asn Glu Ala Lys Ile Asp Glu Ile Lys Asn Asp
                20                  25                  30

Asn Val Gln Asp Thr Ala Glu Gln Lys Val Gln Leu Leu Arg Asn
                35                  40                  45

Trp His Gln Leu His Gly Lys Lys Glu Ala Tyr Asp Thr Leu Ile
                50                  55                  60

Lys Asp Leu Lys Lys Ala Asn Leu Cys Thr Leu Ala Glu Lys Ile
                65                  70                  75

Gln Thr
```